US010934353B2

(12) United States Patent
Freeman et al.

(10) Patent No.: US 10,934,353 B2
(45) Date of Patent: Mar. 2, 2021

(54) SINGLE AGENT ANTI-PD-L1 AND PD-L2 DUAL BINDING ANTIBODIES AND METHODS OF USE

(71) Applicants: Dana-Farber Cancer Institute, Inc., Boston, MA (US); President and Fellows of Harvard College, Cambridge, MA (US)

(72) Inventors: Gordon J. Freeman, Brookline, MA (US); Arlene H. Sharpe, Brookline, MA (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/806,003

(22) Filed: Nov. 7, 2017

(65) Prior Publication Data
US 2018/0201680 A1 Jul. 19, 2018

Related U.S. Application Data

(62) Division of application No. 14/418,536, filed as application No. PCT/US2013/053392 on Aug. 2, 2013, now Pat. No. 9,845,356.

(60) Provisional application No. 61/679,190, filed on Aug. 3, 2012.

(51) Int. Cl.
C07K 16/28 (2006.01)
A01K 67/027 (2006.01)
G01N 33/574 (2006.01)
G01N 33/68 (2006.01)

(52) U.S. Cl.
CPC ...... *C07K 16/2803* (2013.01); *A01K 67/0278* (2013.01); *C07K 16/2827* (2013.01); *G01N 33/57492* (2013.01); *G01N 33/6872* (2013.01); *A01K 2227/105* (2013.01); *A01K 2267/01* (2013.01); *C07K 2317/31* (2013.01); *C07K 2317/33* (2013.01); *C07K 2317/34* (2013.01); *C07K 2317/56* (2013.01); *C07K 2317/565* (2013.01); *C07K 2317/76* (2013.01); *G01N 2333/70503* (2013.01); *G01N 2800/56* (2013.01)

(58) Field of Classification Search
None
See application file for complete search history.

(56) References Cited

U.S. PATENT DOCUMENTS

| 6,808,710 B1 | 10/2004 | Wood et al. |
| 7,722,868 B2 | 5/2010 | Freeman et al. |
| 8,652,465 B2 | 2/2014 | Freeman et al. |
| 2009/0055944 A1 | 2/2009 | Korman et al. |
| 2009/0280128 A1* | 11/2009 | Kamogawa ........ C07K 16/2803 424/141.1 |
| 2011/0033884 A1 | 2/2011 | Wood et al. |
| 2012/0135003 A1 | 5/2012 | Kamogawa et al. |
| 2018/0201680 A1 | 7/2018 | Freeman et al. |

FOREIGN PATENT DOCUMENTS

| WO | WO-2010/036959 A2 | 4/2010 |
| WO | WO-2010/089411 A2 | 8/2010 |
| WO | WO-2011/066342 A2 | 6/2011 |

OTHER PUBLICATIONS

Mulligan-Kehoe et al (JMB, 289:41-55, 1999).*
Almgaro et al., "Humanization of antibodies," Frontiers in Bioscience, 13: 1619-1633 (2008).
Ansari et al., "The Programmed Death-1 (PD-1) Pathway Regulates Autoimmune Diabetes in Nonobese Diabetic (NOD) Mice," J. Exp. Med., 198(1):63-69 (2003).
Brown et al., "Blockade of programmed death-1 ligands on dendritic cells enhances T cell activation and cytokine production," J Immunol, 170(3): 1257-1266 (2003).
Database Biosis, Biosci. Information Service (Philadelphia, PA, US), Brown et al., "Blockade of PD-1 ligands on dendritic cells enhances T cell activation and cytokine production," Database accession No. PREV200200369093 from FASEB J. 16:A710 (Mar. 20, 2002).
Database Geneseq, "Anti-amyloid fibril 5c9.a2 mAb light chain variable region, SEQ ID 82," EBI Accession No. GSP:BBX89341, Database Accession No. BBC89341 (Jun. 4, 2015).
De Genst et al., "Antibody repertoire development in camelids," Dev Comp Immunol, 30: 187-198 (2006).
International Search Report dated Dec. 24, 2013 from PCT/US2013/053392.
Supplementary European Search Report dated Mar. 31, 2016 from EP 13824810.9.
Ohigashi et al., "Clinical significance of programmed death-1 ligand-1 and programmed death-1 ligand-2 expression in human esophageal cancer," Clin Cancer Res, 11(8): 2947-2953 (2005).

* cited by examiner

*Primary Examiner* — Brad Duffy
(74) *Attorney, Agent, or Firm* — Foley Hoag LLP

(57) ABSTRACT

The present invention is based, in part, on the identification of novel antibodies that have binding affinity for both PD-L1 and PD-L2 and methods of using same.

20 Claims, No Drawings

Specification includes a Sequence Listing.

SINGLE AGENT ANTI-PD-L1 AND PD-L2 DUAL BINDING ANTIBODIES AND METHODS OF USE

CROSS-REFERENCE TO RELATED APPLICATIONS

This application claims the benefit of U.S. Provisional Application No. 61/679,190, filed on Aug. 3, 2012; the entire content of said application is incorporated herein in its entirety by this reference.

STATEMENT OF RIGHTS

This invention was made with government support under Grant P01 AI056299 awarded by the National Institutes of Health. The U.S. government has certain rights in the invention. This statement is included solely to comply with 37 C.F.R. § 401.14(a)(f)(4) and should not be taken as an assertion or admission that the application discloses and/or claims only one invention.

BACKGROUND OF THE INVENTION

In order for immune cells, such as T cells, to respond to foreign proteins, two signals must be provided by antigen-presenting cells (APCs) to resting T lymphocytes (Jenkins, M. and Schwartz, R. (1987) *Exp. Med.* 165:302-319; Mueller, D. L. et al. (1990) *J. Immunol.* 144:3701-3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. (1996) Annu. Rev. Immunol. 14:233). Costimulation is neither antigen-specific, nor MHC restricted and is thought to be provided by one or more distinct cell surface polypeptides expressed by APCs (Jenkins, M. K. et al. (1988) *J. Immunol.* 140: 3324-3330; Linsley, P. S. et al. (1991) *J. Exp. Med.* 173: 721-730; Gimmi, C. D., et al. 1991 *Proc. Natl. Acad. Sci. USA* 88:6575-6579; Young, J. W. et al. (1992) *J. Clin. Invest.* 90:229-237; Koulova, L. et al. (1991) *J. Exp. Med.* 173: 759-762; Reiser, H. et al. (1992) *Proc. Natl. Acad. Sci. USA* 89:271-275; van-Seventer, G. A. et al. (1990) *J. Immunol.* 144:4579-4586; LaSalle, J. M. et al. (1991) *J. Immunol.* 147:774-80; Dustin, M. I. et al. (1989) *J. Exp. Med.* 169:503; Armitage, R. J. et al. (1992) *Nature* 357:80-82; Liu, Y. et al. (1992) *J. Exp. Med.* 175:437-445).

In addition to the well-known co-stimulatory pathways, co-inhibitory pathways exist to downregulate T cell activation and immune responses and modulating such co-inhibitory pathways can be used to effectively modulate immune responses. For example, bockade of co-inhibitory pathways offers an approach to stimulate immune responses by blocking negative signals and so has therapeutic potential for treating such ailments as cancer and chronic infectious diseases, such as human immunodeficiency virus (HIV) infection, hepatitis C virus (HCV) infection, malaria, and tuberculosis (TB). However, a network composed of at least (a) PD-L1 and PD-L2 interacting with PD-1; (b) PD-L1 interacting with B7-1; and (c) other receptors interacting with PD-L1 and/or PD-L2 present a complex set of co-inhibitory pathways to target. Current agents only block a subset of these interaction. Indeed, efforts to generate agents that modulate these co-inhibitory pathways have focused on single agents that specifically modulate subsets of interactions. For example, an existing PD-1 monoclonal antibody (mAb) might block the interaction between PD-1 and the PD-1 ligands, PD-L1 and PD-L2, but may not block the interaction between PD-L1 and B7-1 or PD-1 ligands and other receptors (e.g., PD-L2 and RGMb). Thus, such an anti-PD-1 mAb would block only a subset of interactions. Moreover, methods of generating such agents, such as immunization of animal models with PD-L1 or PD-L2 polypeptides, do not yield PD-L1 and PD-L2 dual binding agents since host PD-L1 and PD-L2 leads to tolerization and deletion of the B cells that would produce such agents. Also, the use of large PD-L1 and PD-L2 polypeptides for immunization purposes functionally obscures common epitopes that would give rise to antibodies capable of binding both targets. For example a wild-type mouse will delete antibodies that react against mouse PD-L1 and PD-L2 and so remove a large number of antibodies that bind to structures conserved between human and mouse PD-L1 or PD-L2.

Accordingly, there exists a need in the art to developing compositions with an enhanced ability to simultaneously modulate co-inhibitory pathways and methods of using such compositions to effectively diagnose, prognose, and provide therapy for applications where such enhanced co-inhibitory pathway modulating abilities are beneficial.

SUMMARY OF THE INVENTION

The present invention is based, in part, on the identification of novel antibodies that have binding affinity for both PD-L1 and PD-L2 and methods of using same.

In one aspect, an isolated monoclonal antibody, or antigen-binding fragment thereof, which specifically binds both PD-L1 and PD-L2, is provided. In one embodiment, both PD-L1 and PD-L2 are human PD-L1 and human PD-L2. In another embodiment, human PD-L1 comprises an amino acid sequence having at least 90% identity to the amino acid sequence of SEQ ID NO:4 or 6 and human PD-L2 comprises an amino acid sequence having at least 90% identity to the amino acid sequence of SEQ ID NO:6. In still another embodiment, the isolated monoclonal antibody, or antigen-binding fragment thereof, inhibits one or more of the interactions selected from the group consisting of (a) PD-L1 binding to PD-1; (b) PD-L1 binding to B7-1; (c) PD-L2 binding to PD-1; (d) PD-L2 binding to RGMb; (e) a co-immunoinhibitory signal mediated by PD-L1 binding to PD-1; (f) a co-immunoinhibitory signal mediated by PD-L1 binding to B7-1; (g) a co-immunoinhibitory signal mediated by PD-L2 binding to PD-1; and (h) a co-immunoinhibitory signal mediated by PD-L2 binding to RGMb (e.g., the isolated monoclonal antibody, or antigen-binding fragment thereof, inhibits one or more co-immunoinhibitory signals of (e), (f), (g), or (h)). In yet another embodiment, the isolated monoclonal antibody, or antigen-binding fragment thereof, enhances one or more of the interactions selected from the group consisting of (a) PD-L1 binding to PD-1; (b) PD-L1 binding to B7-1; (c) PD-L2 binding to PD-1; (d) PD-L2 binding to RGMb; (e) a co-immunoinhibitory signal mediated by PD-L1 binding to PD-1; (f) a co-immunoinhibitory signal mediated by PD-L1 binding to B7-1; (g) a co-immunoinhibitory signal mediated by PD-L2 binding to PD-1; and (h) a co-immunoinhibitory signal mediated by PD-L2 binding to RGMb (e.g., the co-immunoinhibitory signal is (e), (f), (g), or (h)). In another embodiment, PD-1, B7-1, or RGMb is a fusion protein. In still another embodiment, the isolated monoclonal antibody, or antigen-binding fragment thereof, binds the peptide sequence CFTVTVPKDLYVVEYGSN or CYRSMISYGGA- DYKRITV. In yet another embodiment, the isolated monoclonal antibody is deposited as hybridoma clone and assigned an accession number. In another embodiment, the isolated monoclonal antibody comprises: a) a heavy chain sequence with at least about 95% identity to a heavy chain sequence selected from the group consisting of the sequences listed in Table 1 or b) a light chain sequence with at least about 95% identity to a light chain sequence selected from the group consisting of the sequences listed in Table 1. In still another embodiment, the isolated monoclonal antibody comprises: a) a heavy chain CDR sequence with at least about 95% identity to a heavy chain CDR sequence selected from the group consisting of the sequences listed in Table 1 or b) a light chain CDR sequence with at least about 95% identity to a light chain sequence CDR sequence selected from the group consisting of the sequences listed in Table 1. In yet another embodiment, the isolated monoclonal antibody comprises: a) a heavy chain sequence selected from the group consisting of the sequences listed in Table 1; or b) a light chain sequence selected from the group consisting of the sequences listed in Table 1. In another embodiment, the isolated monoclonal antibody comprises: a) a heavy chain CDR sequence selected from the group consisting of the sequences listed in Table 1; or b) a light chain CDR sequence selected from the group consisting of the sequences listed in Table 1. In still another embodiment, the isolated monoclonal antibody or antigen-binding fragment thereof is chimeric, humanized, composite, rodent, or human. In yet another embodiment, the isolated monoclonal antibody or antigen-binding fragment thereof is a F(ab')2 fragment, Fab fragment, scFv, bi-specific scFv, tri-specific scFv, diabody, single domain antibody (dAb), minibody, or molecular recognition unit (MRU). In another embodiment, the isolated monoclonal antibody or antigen-binding fragment thereof inhibits the binding of a commercial antibody to PD-L1 or PD-L2. In still another embodiment, the presence of the isolated monoclonal antibody or antigen-binding fragment thereof reduces or inhibits at least one PD-L1 or PD-L2 activity relative to the absence of the isolated monoclonal antibody or antigen-binding fragment thereof.

In another aspect, a pharmaceutical composition comprising an isolated monoclonal antibody, or antigen-binding fragment thereof, described herein and a pharmaceutically-acceptable carrier, is provided.

In still another aspect, an isolated nucleic acid molecule that hybridizes, under stringent conditions, with the complement of a nucleic acid encoding a polypeptide of a monoclonal antibody described herein, or a sequence with at least about 95% homology to a nucleic acid encoding a polypeptide of a monoclonal antibody described herein, is provided.

In yet another aspect, a vector comprising an isolated nucleic acid described herein, is provided.

In another aspect, host cell which comprises an isolated nucleic acid described herein and/or expresses the antibody or antigen-binding fragment thereof described herein, is provided.

In still another aspect, a transgenic animal which comprises an isolated nucleic acid described herein and/or expresses the antibody or antigen-binding fragment thereof described herein, is provided.

In yet another aspect, a method of producing at least one monoclonal antibody or antigen-binding fragment thereof, described herein, comprising culturing a cell that produces the at least one monoclonal antibody, or antigen-binding fragment thereof, from the cell culture, is provided.

In another aspect, a device or kit comprising at least one monoclonal antibody or antigen-binding fragment thereof, described herein, said device or kit optionally comprising a label to detect the at least one monoclonal antibody, or antigen-binding fragment thereof, or a complex comprising the monoclonal antibody or antigen-binding fragment thereof, is provided. In one embodiment, the device detects the presence of a PD-L1 and/or PD-L2 polypeptide in a sample by use of a sandwich assay or a competition assay.

In still another aspect, a method of detecting the presence or level of a PD-L1 and/or PD-L2 polypeptide said method comprising obtaining a sample and detecting said polypeptide in a sample by use of at least one monoclonal antibody, or antigen-binding fragment thereof, described herein, is provided. In one embodiment, the at least one monoclonal antibody or antigen-binding fragment thereof forms a complex with a PD-L1 and/or PD-L2 polypeptide and the complex is detected in the form of an enzyme linked immunosorbent assay (ELISA), radioimmune assay (RIA), or immunochemically. In another embodiment, the sample is obtained from a subject.

In yet another aspect, a method of monitoring the course, or recurrence, of a disease in a subject, said method comprising determining the level of a PD-L1 and/or PD-L2 polypeptide in a sample from said subject based on formation of a complex comprising at least one monoclonal antibody, or antigen-binding fragment thereof, described herein and the PD-L1 and/or PD-L2 polypeptide, wherein the level of PD-L1 and/or PD-L2 indicates the course, or recurrence, of the disease, is provided. In one embodiment, the step of determining is performed by enzyme linked immunosorbent assay (ELISA), radioimmune assay (RIA), immunochemically, or using an intracellular flow assay. In another embodiment, the disease is selected from the group consisting of cancer, metabolic syndrome, and dyslipidemia.

In another aspect, a method of determining whether to administer a PD-L1 and/or PD-L2 inhibitor to a subject, comprising determining the level of PD-L1 and/or PD-L2 polypeptide in a sample from said subject based on formation of a complex comprising at least one monoclonal antibody, or antigen-binding fragment thereof, described herein and the PD-L1 and/or PD-L2 polypeptide; and determining whether to administer the PD-L1 and/or PD-L2 inhibitor based on the level of PD-L1 and/or PD-L2 polypeptide detected, is provided. In one embodiment, the step of determining is performed by enzyme linked immunosorbent assay (ELISA), radioimmune assay (RIA), immunochemically, or using an intracellular flow assay.

In still another aspect, a method of reactivating exhausted T cells, comprising contacting a population of cells, wherein at least some cells express PD-L1 and/or PD-L2, with an effective amount of a composition comprising at least one monoclonal antibody, or antigen-binding fragment thereof, described herein.

In yet another aspect, a method of treating a subject having a condition that would benefit from modulation of an immune response, comprising administering to the subject an effective amount of a composition comprising at least one monoclonal antibody, or antigen-binding fragment thereof, described herein. In one embodiment, the condition is an infection (e.g., a viral infection, bacterial infection, protozoan infection, or helminth infection). In still another embodiment, the condition is cancer (e.g., a solid tumor, a hematologic cancer, bladder cancer, brain cancer, breast cancer, colon cancer, gastric cancer, glioma, head cancer, leukemia, liver cancer, lung cancer, lymphoma, myeloma, neck cancer, ovarian cancer, melanoma, pancreatic cancer, renal cancer, salivary cancer, stomach cancer, thymic epithelial cancer, or thyroid cancer). In yet another embodiment, the condition is an inflammatory disorder (e.g., acute disseminated encephalomyelitis, Addison's disease, ankylosing spondylitis, antiphospholipid antibody syndrome, autoimmune hemolytic anemia, autoimmune hepatitis, arthritis, Behcet's disease, Bullous pemphigoid, Celiac disease, Chagas' disease, Crohn's disease, Dermatomyositis, Diabetes mellitus type 1, Goodpasture's syndrome, graft-versus-host disease, Graves' disease, Guillain-Barre syndrome, Hashimoto's disease, hyper IgE syndrome, idiopathic thrombocytopenic purpura, lupus erythematosus, multiple sclerosis, myasthenia gravis, pemphigus, pernicious anaemia, polymyositis, primary biliary cirrhosis, psoriasis, rheumatoid arthritis, Sjogren's syndrome, temporal arteritis, vasculitis, or Wegener's granulomatosis). In another embodiment, the condition is transplant rejection (e.g., organ rejection, bone marrow transplant rejection, or non-myeloablative bone marrow transplant rejection).

DETAILED DESCRIPTION OF THE INVENTION

Current agents inefficiently modulate subsets of co-inhibitory pathways since they are only capable of binding and modulating the activity of single targets (e.g., CTLA4, B7-1, RGMb, PD-1, PD-L1, or PD-L2). This poses problems for the development of useful diagnostic and therapeutic agents, since the additional agents required to effectively modulate other co-inhibitory pathways (e.g., anti-CTLA4, anti-B7-1, anti-RGMb, anti-PD-1, anti-PD-L1, and/or anti-PD-L2 antibodies) significantly complicate diagnostic and therapeutic regimens and increase the burden of clinical regulatory requirements. Accordingly, the present invention is based, at least in part, on novel antibody compositions that bind to both PD-L1 and PD-L2. In addition, the problem of tolerization and deletion of host B cells that produce such desired compositions has been overcome by immunizing host animals harboring knockout mutations of PD-L1 and PD-L2, since these mice lack these proteins and so have not been tolerized or deleted of any B cells producing antibodies that bind to PD-L1 or PD-L2. Among the generated antibodies, preferred dual binding antibodies have been isolated that are monoclonal dual blocker antibodies that can block multiple inhibitory pathways. The achievement in generating the described dual binding antibodies is based on the discovery that the structures of PD-L1 and PD-L2 have regions of great similarity, particularly in the region in the IgV domain involved in binding to PD-1. In addition, it has been discovered that the peptides, CFTVTVPKDLYVVEYGSN and CYRSMISYGGADYKRITV, represent immunogenic epitopes for generating desired dual binding antibodies based on structural and sequence conservation analysis between PD-L1 and PD-L2, as well as the binding relationships between PD-1 and its ligands, PD-L1 and PD-L2.

In order that the present invention may be more readily understood, certain terms are first defined. Additional definitions are set forth throughout the detailed description.

The articles "a" and "an" are used herein to refer to one or to more than one (i.e. to at least one) of the grammatical object of the article. By way of example, "an element" means one element or more than one element.

As used herein, the term "activity," when used with respect to a polypeptide, e.g., human PD-L1 and/or PD-L2 polypeptide, includes activities which are inherent in the structure of the protein as described above.

As used herein, the term "antibody" includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. "Inactivating antibodies" refers to antibodies that do not induce the complement system. Antibodies may be polyclonal or monoclonal; xenogeneic, allogeneic, or syngeneic; or modified forms thereof (e.g., humanized, chimeric, etc.). Antibodies may also be fully human. In preferred embodiments, antibodies of the invention bind specifically or substantially specifically to human PD-L1 and human PD-L2.

As used herein, the term "antigen-binding portion" or "antigen-binding fragment" of an antibody, refers to one or more fragments of an antibody that retain the ability to specifically bind to an antigen (e.g., human PD-L1 and/or PD-L2). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_H$, $V_L$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_H$ and $V_L$ domains of a single arm of an antibody, (v) a dAb fragment (Ward et al., (1989) Nature 341:544 546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423 426; and Huston et al. (1988) Proc. Natl. Acad. Sci. USA 85:5879 5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

As used herein, the term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes). The term "T cell" includes CD4+ T cells and CD8+ T cells. The term T cell also includes T helper 1 type T cells, T helper 2 type T cells, T helper 17 type T cells and inhibitory T cells.

As used herein, the term "binding affinity" refers to a measure by which an agent binds to a target molecule. Binding affinity is "specific" if it is strong enough to bind a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in, for example, a BIACORE 3000 instrument using recombinant target protein (e.g., human PD-L1 and/or human PD-L2) as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "body fluid" refers to fluids that are excreted or secreted from the body as well as fluids that are normally not (e.g. amniotic fluid, aqueous humor, bile, blood, blood plasma, cerebrospinal fluid, cerumen, earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, and vomit).

As used herein, the terms "cancer" or "tumor" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, lymphomas, including including gray zone lymphoma, Hodgkin's lymphoma and non-Hodgkin's lymphoma (including both T and B cell non-Hodgkin's lymphomas, e.g., mantle zone lymphoma, mediastinal large B cell lymphoma, diffuse large B-cell lymphoma, follicular lymphoma, extranodal marginal zone lymphoma of mucosa-associated tissue (MALT lymphoma), Burkitt lymphoma, nodal marginal zone lymphoma, small lymphocytic lymphoma (SLL), lymphoplasmacytic lymphoma (also called Waldenstrom's macroglobulinaemia)), squamous cell carcinoma, B cell cancer, e.g., multiple myeloma, the heavy chain diseases, such as, for example, alpha chain disease, gamma chain disease, and mu chain disease, benign monoclonal gammopathy, immunocytic amyloidosis, melanomas (e.g., metastatic melanoma), breast cancer, lung cancer (e.g., small cell lung cancer and non-small cell lung cancer), bronchus cancer, colorectal cancer, prostate cancer (e.g., metastatic, hormone refractory prostate cancer), pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer (e.g., renal cell carcinoma), testicular cancer, biliary tract cancer, small bowel or appendix cancer, salivary gland cancer, thyroid gland cancer, adrenal gland cancer, osteosarcoma, chondrosarcoma, cancer of hematological tissues, and the like.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," $5^{th}$ Edition, U.S. Department of Health and Human Services, 1992; Chothia et al. (1987) J. Mol. Biol. 196, 901; and MacCallum et al., J. Mol. Biol. (1996) 262, 732, each of which is incorporated by reference in its entirety).

As used herein, the term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germline immunoglobulin sequences and variable regions comprising human germline or non-germline sequences from two or more unrelated human variable regions. A composite, human antibody is useful as an effective component in a therapeutic agent according to the present invention since the antigenicity of the composite, human antibody in the human body is lowered.

The present invention also encompasses "conservative sequence modifications", including nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an antibody of the present invention is preferably replaced with another amino acid residue from the same side chain family. Alternatively, in another embodiment, mutations can be introduced randomly along all or part of nucleic acid sequences encoding antibodies that bind both PD-L1 and/or PD-L2, such as by saturation mutagenesis, and the resulting modified antibodies can be screened for binding activity.

In addition, there is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequences in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 81%, 82%, 83%, 84%, 85%, 86%, 87%, 88%, 89%, 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=#of identical positions/total #of positions× 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11 17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444 453 (1970)) algorithm which has been incorporated into the GAP program in the GCG software package (available on the world wide web at the GCG company website), using either a Blosum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403 10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389 3402. When utilizing BLAST and Gapped BLAST programs, the default parameters of the respective programs (e.g., XBLAST and NBLAST) can be used (available on the world wide web at the NCBI website).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art (see, F. Ausubel, et al., ed. Current Protocols in Molecular Biology, Greene Publishing and Wiley Interscience, New York (1987)).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

As used herein, the term "dual binding antibody" refers to an antibody that has binding affinity for more than one physically distinct polypeptides having distinct polypeptide sequences. Such dual binding antibodies can, for example, recognize and bind a common epitope shared by two physically distinct polypeptides having distinct polypeptide sequences in regions other than the bound epitope sequences. In a preferred embodiment, the dual binding antibody is an "anti-PD-L1/PD-L2 antibody," also referred to herein as an "anti-PD-L1 and anti-PD-L2 antibody," an "anti-PD-L1/PD-L2 dual binding antibody," and the like.

As used herein, the term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the invention include human IgG1, IgG2 (IgG2A, IgG2B), IgG3 and IgG4.

As used herein, a molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

As used herein, "framework" or "FR" residues are those variable-domain residues other than the HVR residues as herein defined.

As used herein, "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, Annu. Rev. Immunol. 15:203-234 (1997). FcRs are reviewed in Ravetch and Kinet, Annu. Rev. Immunol. 9: 457-92 (1991); Capel et al., Immunomethods 4: 25-34 (1994); and de Haas et al., J. Lab. Clin. Med. 126: 330-41 (1995). Other FcRs, including those to be identified in the future, are encompassed by the term "FcR" herein.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like) Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

As used herein, the term "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the $C_H$ genes of the transgene were derived.

As used herein, the term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, the term "humanized antibody" refers to an antibody that consists of the CDR of antibodies derived from mammals other than human, and the FR region and the constant region of a human antibody. A humanized antibody is useful as an effective component in a therapeutic agent according to the present invention since antigenicity of the humanized antibody in the human body is lowered.

As used herein, the term "hypervariable region," "HVR," or "HV," refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. (2000) Immunity 13, 37-45; Johnson and Wu in Methods in Molecular Biology 248, 1-25 (Lo, ed., Human Press, Totowa, N.J., 2003)). Indeed, naturally occurring camelid antibodies consisting of a heavy chain only are functional and stable in the absence of light chain (see, e.g., Hamers-Casterman et al. (1993) Nature 363:446-448 (1993) and Sheriff et al. (1996) Nature Struct. Biol. 3, 733-736).

As used herein, the term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly affected by T cell activation, e.g., antibody production (humoral responses) and activation of cytokine responsive cells, e.g., macrophages.

As used herein, the term "inhibit" includes the decrease, limitation, or blockage, of, for example, a particular action, function, or interaction. As used herein, the term "inhibitory signal" refers to a signal transmitted via an inhibitory receptor (e.g., CTLA4, PD-1, or RGMb) for a polypeptide on an immune cell. Such a signal antagonizes a signal via an activating receptor (e.g., via a TCR or CD3 polypeptide) and can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

As used herein, the term "interaction," when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding a ligand, and thus be held inactive with respect to ligand binding activity (e.g., binding its ligand and triggering or inhibiting costimulation). To inhibit such an interaction results in the disruption of the activity of one or more molecules involved in the interaction. To enhance such an interaction is to prolong or increase the likelihood of said physical contact, and prolong or increase the likelihood of said activity.

As used herein, the term an "isolated antibody" is intended to refer to an antibody which is substantially free of other antibodies having different antigenic specificities (e.g., an isolated antibody that specifically binds to human PD-L1 and/or PD-L2 and is substantially free of antibodies that do not bind to human PD-L1 and/or PD-L2). An isolated antibody that specifically binds to an epitope of human PD-L1 and/or PD-L2 may, however, have cross-reactivity to other human PD-L1 and/or PD-L2 proteins, respectively, from different species. However, in preferred embodiments, the antibody maintains higher affinity and selectivity for human PD-L1 and/or PD-L2. In addition, an isolated antibody is typically substantially free of other cellular material and/or chemicals. In one embodiment of the invention, a combination of "isolated" monoclonal antibodies having different specificities to human PD-L1 and/or PD-L2 are combined in a well defined composition.

As used herein, the term "isotype" refers to the antibody class (e.g., IgM or IgG1) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

As used herein, a "kit" is any manufacture (e.g. a package or container) comprising at least one reagent, e.g. a probe, for specifically detecting or modulating the expression of a marker of the invention. The kit may be promoted, distributed, or sold as a unit for performing the methods of the present invention.

As used herein, the term "modulate" includes up-regulation and down-regulation, e.g., enhancing or inhibiting a response or biological activity.

As used herein, the term "monoclonal antibody", refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "nucleic acid molecule" is intended to include DNA molecules and RNA molecules. A nucleic acid molecule may be single-stranded or double-stranded, but preferably is double-stranded DNA. As used herein, the term "isolated nucleic acid molecule" in reference to nucleic acids encoding antibodies or antibody portions (e.g., $V_H$, $V_L$, CDR3) that bind to PD-L1 and/or PD-L2, is intended to refer to a nucleic acid molecule in which the nucleotide sequences encoding the antibody or antibody portion are free of other nucleotide sequences encoding antibodies or antibody portions that bind antigens other than PD-L1 and/or PD-L2, which other sequences may naturally flank the nucleic acid in human genomic DNA.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

An "over-expression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

As used herein, the term "patient" includes a human subject who has presented at a clinical setting with a particular symptom or symptoms suggesting one or more diagnoses. A patient may be in need of further categorization by clinical procedures well-known to medical practitioners of the art (or may have no further disease indications and appear to be in any or all respects normal). A patient's diagnosis may alter during the course of disease progression, such as development of further disease symptoms, or remission of the disease, either spontaneously or during the course of a therapeutic regimen or treatment. The term "diagnosis" does not preclude different earlier or later diagnoses for any particular patient or subject. The term "prognosis" refers to assessment for a subject or patient of a probability of developing a condition associated with or otherwise indicated by presence of one or more enzymes in a biological sample.

The term "PD-1" refers to a member of the immunoglobulin gene superfamily that functions as a coinhibitory receptor having PD-L1 and PD-L2 as known ligands. PD-1 was previously identified using a subtraction cloning based approach to select for proteins involved in apoptotic cell death. PD-1 is a member of the CD28/CTLA-4 family of molecules based on its ability to bind to PD-L1. Like CTLA4, PD-1 is rapidly induced on the surface of T-cells in response to anti-CD3 (Agata et al. 25 (1996) *Int. Immunol.* 8:765). In contrast to CTLA4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

The nucleic acid and amino acid sequences of a representative human PD-1 biomarker is available to the public at the GenBank database under NM_005018.2 and NP_005009.2 and is shown in Table 1 (see also Ishida et al. (1992) 20 *EMBO J* 11:3887; Shinohara et al. (1994) *Genomics* 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J.* 11:3887; Shinohara et al. (1994) *Genomics* 23:704; U.S. Pat. No. 5,698,520). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) Immunol. Today 20(6):285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) J. Exp. Med. 192:1027 for sequence data) and PD-L2 (See Latchman et al. (2001) Nat. Immunol. 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells.

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MHC molecules share the same types of sequence patterns and are called the C1-set within the Ig superfamily Other IgC domains fall within other sets. IgV domains also share sequence patterns and are called V set domains. IgV domains are longer than IgC domains and contain an additional pair of β strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation depending on the receptor it is interacting with. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

In some embodiments, B7-1 and/or B7-2 members of the B7 family are preferred. The proteins B7-1 (CD80) and B7-2 (CD86) are critical costimulatory molecules (Freeman et al. (1991) J. Exp. Med. 174:625; Freeman et al. (1989) J. Immunol. 143:2714; Azuma et al. (1993) Nature 366:76; Freeman et al. (1993) Science 262:909). B7-2 plays a predominant role during primary immune responses, while B7-1, which is upregulated later during an immune response, may be important for prolonging primary T cell responses or costimulating secondary T cell responses (Bluestone (1995) Immunity 2:555). PD-L1 binds to both PD-1 and B7-1. Both binding of T-cell-expressed B7-1 by PD-L1 and binding of T-cell-expressed PD-L1 by B7-1 result in T cell inhibition (Butte et al. (2007) Immunity 27:111). The nucleic acid and amino acid sequences of representative human B7-1 biomarkers are available to the public at the GenBank database under NM_005191.3 and NP_005182.1 (shown in Table 1 as SEQ ID NOs: 11 and 12). In addition, nucleic acid and polypeptide sequences of B7-1 orthologs in organisms other than humans are well known and include, for example, chimpanzee B7-1 (XM_001163234.2 and XP_001163234.1), dog B7-1 (NM_001003147.1 and NP_001003147.1), cow B7-1 (NM_001206439.1 and NP_001193368.1), mouse B7-1 (NM_009855.2 and NP_033985.3), and rat B7-1 (NM_012926.1 and NP_037058.1).

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The term "PD-L1" refers to a specific PD-1 ligand. Two forms of human PD-L1 molecules have been identified. One form is a naturally occurring PD-L1 soluble polypeptide, i.e., having a short hydrophilic domain at the COOH-terminal end and no transmembrane domain, and is referred to herein as PD-L1S (shown in Table 1 as SEQ ID NO: 4). The second form is a cell-associated polypeptide, i.e., having a transmembrane and cytoplasmic domain, referred to herein as PD-L1M (shown in SEQ ID NO: 6). The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence of SEQ ID NO: 4 is shown from about amino acid 1 to about amino acid 18. The signal sequence of SEQ ID NO: 6 is shown: from about amino acid 1 to about amino acid 18. The IgV domain of SEQ ID NO: 4 is shown from about amino acid 19 to about amino acid 134 and the IgV domain of SEQ ID NO: 6 is shown from about amino acid 19 to about amino acid 134. The IgC domain of SEQ ID NO: 4 is shown from about amino acid 135 to about amino acid 227 and the IgC domain of SEQ ID NO: 6 is shown from about amino acid 135 to about amino acid 227. The hydrophilic tail of the PD-L1 exemplified in SEQ ID NO: 4 comprises a hydrophilic tail shown from about amino acid 228 to about amino acid 245. The PD-L1 polypeptide exemplified in SEQ ID NO: 6 comprises a transmembrane domain shown from about amino acids 239 to about amino acid 259 of SEQ ID NO: 6 and a cytoplasmic domain shown of about 30 amino acids from 260 to about amino acid 290 of SEQ ID NO: 6. In addition, nucleic acid and polypeptide sequences of PD-L1 orthologs in organisms other than humans are well known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers (e.g., SEQ ID NOs: 7 and 8) are well known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of SEQ ID NO: 8 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19: 235-263. In still another embodiment, amino acid residues 20-120 of the native human PD-L2 polypeptide and amino acid residues 1-101 of the mature polypeptide comprise an IgV domain Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two β sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the C1 set within the Ig superfamily Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner, e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra- or intercellular signaling, 3) modulate activation of immune cells, e.g., T lymphocytes, and 4) modulate the immune response of an organism, e.g., a mouse or human organism.

The term "peripheral blood cell subtypes" refers to cell types normally found in the peripheral blood including, but is not limited to, eosinophils, neutrophils, T cells, monocytes, NK cells, granulocytes, and B cells.

As used herein, the term "rearranged" refers to a configuration of a heavy chain or light chain immunoglobulin locus wherein a V segment is positioned immediately adjacent to a D-J or J segment in a conformation encoding essentially a complete $V_H$ and $V_L$ domain, respectively. A rearranged immunoglobulin gene locus can be identified by comparison to germline DNA; a rearranged locus will have at least one recombined heptamer/nonamer homology element.

As used herein, the term "recombinant host cell" (or simply "host cell"), is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "RGMb" refers to a glycosylphophatidylinositol (GPI)-anchored member of the repulsive guidance molecule family Samad et al. in JBC Papers 2005, Vol. 280, 14122-

14129 describe the interaction between RGMb and the Type I and Type II receptors of bone morphogenetic protein (BMP). However, the interaction between RGMb and PD-L2 was not previously known. The nucleic acid and amino acid sequences of representative human RGMb biomarkers (e.g., SEQ ID NOs: 9 and 10) are well known in the art and are also available to the public at the GenBank database under NM_025239.3 and NP_079515.2. RGMb proteins are characterized by common structural elements. In some embodiments, RGMb proteins comprise conserved domains with homology to notch-3, phosphatidylinositol-4-phosphate-5-kinase type II beta, insulin-like growth factor binding protein-2, thrombospondin, ephrin type-B receptor 3 precursor, and Slit-2, all of which are known to influence axonal guidance, neurite outgrowth, and other neuronal developmental functions. The C-terminus of RGMb also contains a hydrophobic domain indicative of a 21 amino acid extracellular GPI anchoring. In addition, nucleic acid and polypeptide sequences of RGMb orthologs in organisms other than humans are well known and include, for example, mouse RGMb (NM_178615.3 and NP_848730.2), chimpanzee RGMb (XM_517848.3 and XP_517848.2), cow RGMb (XM_002689413.1 and XP_002689459.1), chicken RGMb (XM_42860.3 and XP_424860.3), and zebrafish RGMb (NM_001001727.1 and NP_001001727.1).

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

As used herein, the term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using human PD-L1 and/or PD-L2 as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, the term "subject" includes any living animal or human in need of diagnosis or prognosis for, or susceptible to, a condition, in particular to a condition mediated by PD-L1 and/or PD-L2, as described below. The term "non-human animal" includes all vertebrates, e.g., mammals and non-mammals, such as non-human primates, sheep, dog, cow, chickens, amphibians, reptiles, etc. A subject or non-human animal is treated if one or more beneficial or desired results, including desirably clinical results, are obtained. For purposes of this invention, beneficial or desired clinical results include, but are not limited to, one or more of the following: decreasing one or more symptoms resulting from the disease, increasing the quality of life of those suffering from the disease, decreasing the dose of other medications required to treat the disease, delaying the progression of the disease, and/or prolonging survival of individuals.

As used herein, the term "unrearranged" or "germline configuration" in reference to a V segment refers to the configuration wherein the V segment is not recombined so as to be immediately adjacent to a D or J segment.

As used herein, the term "vector" is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for a fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

Finally, nucleic acid and amino acid sequence information for nucleic acid and polypeptide molecules useful in the present invention are well known in the art and readily available on publicly available databases, such as the National Center for Biotechnology Information (NCBI). For example, exemplary nucleic acid and amino acid sequences derived from publicly available sequence databases are provided in Table 1 below. Table 1 also presents newly described antibody variable region and associated CDR sequences referred to herein.

TABLE 1

SEQ ID NO: 1 Human PD-1 cDNA Sequence

```
cactctggtg gggctgctcc aggc atg cag atc cca cag gcg ccc tgg cca           51
                          Met Gln Ile Pro Gln Ala Pro Trp Pro
                           1               5 gtc gtc tgg gcg gtg cta caa ctg ggc tgg cgg cca gga tgg ttc tta          99
Val Val Trp Ala Val Leu Gln Leu Gly Trp Arg Pro Gly Trp Phe Leu
 10              15                  20                  25 gac tcc cca gac agg ccc tgg aac ccc ccc acc ttc tcc cca gcc ctg         147
Asp Ser Pro Asp Arg Pro Trp Asn Pro Pro Thr Phe Ser Pro Ala Leu
                 30                  35                  40 ctc gtg gtg acc gaa ggg gac aac gcc acc ttc acc tgc agc ttc tcc         195
Leu Val Val Thr Glu Gly Asp Asn Ala Thr Phe Thr Cys Ser Phe Ser
             45                  50                  55 aac aca tcg gag agc ttc gtg cta aac tgg tac cgc atg agc ccc agc         243
Asn Thr Ser Glu Ser Phe Val Leu Asn Trp Tyr Arg Met Ser Pro Ser
         60                  65                  70 aac cag acg gac aag ctg gcc gcc ttc ccc gag gac cgc agc cag ccc         291
Asn Gln Thr Asp Lys Leu Ala Ala Phe Pro Glu Asp Arg Ser Gln Pro
     75                  80                  85 ggc cag gac tgc cgc ttc cgt gtc aca caa ctg ccc aac ggg cgt gac         339
Gly Gln Asp Cys Arg Phe Arg Val Thr Gln Leu Pro Asn Gly Arg Asp
 90                  95                 100                 105 ttc cac atg agc gtg gtc agg gcc cgg cgc aat gac agc ggc acc tac         387
Phe His Met Ser Val Val Arg Ala Arg Arg Asn Asp Ser Gly Thr Tyr
                110                 115                 120 ctc tgt ggg gcc atc tcc ctg gcc ccc aag gcg cag atc aaa gag agc         435
Leu Cys Gly Ala Ile Ser Leu Ala Pro Lys Ala Gln Ile Lys Glu Ser
            125                 130                 135 ctg cgg gca gag ctc agg gtg aca gag aga agg gca gaa gtg ccc aca         483
Leu Arg Ala Glu Leu Arg Val Thr Glu Arg Arg Ala Glu Val Pro Thr
        140                 145                 150 gcc cac ccc agc ccc tca ccc agg tca gcc ggc cag ttc caa acc ctg         531
Ala His Pro Ser Pro Ser Pro Arg Ser Ala Gly Gln Phe Gln Thr Leu
    155                 160                 165 gtg gtt ggt gtc gtg ggc ggc ctg ctg ggc agc ctg gtg ctg cta gtc         579
Val Val Gly Val Val Gly Gly Leu Leu Gly Ser Leu Val Leu Leu Val
170                 175                 180                 185 tgg gtc ctg gcc gtc atc tgc tcc cgg gcc gca cga ggg aca ata gga         627
Trp Val Leu Ala Val Ile Cys Ser Arg Ala Ala Arg Gly Thr Ile Gly
                190                 195                 200 gcc agg cgc acc ggc cag ccc ctg aag gag gac ccc tca gcc gtg cct         675
Ala Arg Arg Thr Gly Gln Pro Leu Lys Glu Asp Pro Ser Ala Val Pro
            205                 210                 215 gtg ttc tct gtg gac tat ggg gag ctg gat ttc cag tgg cga gag aag         723
Val Phe Ser Val Asp Tyr Gly Glu Leu Asp Phe Gln Trp Arg Glu Lys
        220                 225                 230 acc ccg gag ccc ccc gtg ccc tgt gtc cct gag cag acg gag tat gcc         771
Thr Pro Glu Pro Pro Val Pro Cys Val Pro Glu Gln Thr Glu Tyr Ala
    235                 240                 245 acc att gtc ttt cct agc gga atg ggc acc tca tcc ccc gcc cgc agg         819
Thr Ile Val Phe Pro Ser Gly Met Gly Thr Ser Ser Pro Ala Arg Arg
250                 255                 260                 265 ggc tca gct gac ggc cct cgg agt gcc cag cca ctg agg cct gag gat         867
Gly Ser Ala Asp Gly Pro Arg Ser Ala Gln Pro Leu Arg Pro Glu Asp
                270                 275                 280 gga cac tgc tct tgg ccc ctc tgaccggctt ccttggccac cagtgttctg cag       921
Gly His Cys Ser Trp Pro Leu
            285

SEQ ID NO: 2 Human PD-1 Amino Acid Sequence
Met Gln Ile Pro Gln Ala Pro Trp Pro Val Val Trp Ala Val Leu Gln
 1               5                  10                  15
```

TABLE 1-continued

```
Leu Gly Trp Arg Pro Gly Trp Phe Leu Asp Ser Pro Asp Arg Pro Trp
             20                  25                  30

Asn Pro Pro Thr Phe Ser Pro Ala Leu Leu Val Val Thr Glu Gly Asp
             35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Ser Ala Gly Gln Phe Gln Thr Leu Val Val Gly Val Val Gly Gly
            165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

SEQ ID NO: 3 Human PD-L1S cDNA Acid Sequence
gcttcccgag gctccgcacc agccgcgctt ctgtccgcct gcagggcatt ccagaaag      58
atg agg ata ttt gct gtc ttt ata ttc atg acc tac tgg cat ttg ctg    106
Met Arg Ile Phe Ala Val Phe Ile Phe Met Thr Tyr Trp His Leu Leu
 1               5                  10                  15 aac gca ttt act gtc acg gtt ccc aag gac cta tat gtg gta gag tat    154
Asn Ala Phe Thr Val Thr Val Pro Lys Asp Leu Tyr Val Val Glu Tyr
             20                  25                  30 ggt agc aat atg aca att gaa tgc aaa ttc cca gta gaa aaa caa tta    202
Gly Ser Asn Met Thr Ile Glu Cys Lys Phe Pro Val Glu Lys Gln Leu
         35                  40                  45 gac ctg gct gca cta att gtc tat tgg gaa atg gag gat aag aac att    250
Asp Leu Ala Ala Leu Ile Val Tyr Trp Glu Met Glu Asp Lys Asn Ile
 50                  55                  60 att caa ttt gtg cat gga gag gaa gac ctg aag gtt cag cat agt agc    298
Ile Gln Phe Val His Gly Glu Glu Asp Leu Lys Val Gln His Ser Ser
 65                  70                  75                  80 tac aga cag agg gcc cgg ctg ttg aag gac cag ctc tcc ctg gga aat    346
Tyr Arg Gln Arg Ala Arg Leu Leu Lys Asp Gln Leu Ser Leu Gly Asn
                 85                  90                  95 gct gca ctt cag atc aca gat gtg aaa ttg cag gat gca ggg gtg tac    394
Ala Ala Leu Gln Ile Thr Asp Val Lys Leu Gln Asp Ala Gly Val Tyr
            100                 105                 110
```

TABLE 1-continued

```
cgc tgc atg atc agc tat ggt ggt gcc gac tac aag cga att act gtg    442
Arg Cys Met Ile Ser Tyr Gly Gly Ala Asp Tyr Lys Arg Ile Thr Val
        115             120             125 aaa gtc aat gcc cca tac aac aaa atc aac caa aga att ttg gtt gtg    490
Lys Val Asn Ala Pro Tyr Asn Lys Ile Asn Gln Arg Ile Leu Val Val
130             135             140 gat cca gtc acc tct gaa cat gaa ctg aca tgt cag gct gag ggc tac    538
Asp Pro Val Thr Ser Glu His Glu Leu Thr Cys Gln Ala Glu Gly Tyr
145             150             155             160 ccc aag gcc gaa gtc atc tgg aca agc agt gac cat caa gtc ctg agt    586
Pro Lys Ala Glu Val Ile Trp Thr Ser Ser Asp His Gln Val Leu Ser
            165             170             175 ggt aag acc acc acc acc aat tcc aag aga gag gag aag ctt ttc aat    634
Gly Lys Thr Thr Thr Thr Asn Ser Lys Arg Glu Glu Lys Leu Phe Asn
            180             185             190 gtg acc agc aca ctg aga atc aac aca aca act aat gag att ttc tac    682
Val Thr Ser Thr Leu Arg Ile Asn Thr Thr Thr Asn Glu Ile Phe Tyr
        195             200             205 tgc act ttt agg aga tta gat cct gag gaa aac cat aca gct gaa ttg    730
Cys Thr Phe Arg Arg Leu Asp Pro Glu Glu Asn His Thr Ala Glu Leu
    210             215             220 gtc atc cca ggt aat att ctg aat gtg tcc att aaa ata tgt cta aca    778
Val Ile Pro Gly Asn Ile Leu Asn Val Ser Ile Lys Ile Cys Leu Thr
225             230             235             240 ctg tcc cct agc acc tagcatgatg tctgcctatc atagtcattc agtgattgtt    833
Leu Ser Pro Ser Thr
            245 gaataaatga atgaatgaat aacactatgt ttacaaaata tatcctaatt cctcacctcc    893
attcatccaa accatattgt tacttaataa acattcagca gatatttatg gaataaaaaa    953
aaaaaaaaa aaaaa                                                      968

SEQ ID NO: 4 Human PD-L1S Amino Acid Sequence
Met Arg Ile Phe Ala Val Phe Ile Phe Met Thr Tyr Trp His Leu Leu
1               5               10              15

Asn Ala Phe Thr Val Thr Val Pro Lys Asp Leu Tyr Val Val Glu Tyr
            20              25              30

Gly Ser Asn Met Thr Ile Glu Cys Lys Phe Pro Val Glu Lys Gln Leu
        35              40              45

Asp Leu Ala Ala Leu Ile Val Tyr Trp Glu Met Glu Asp Lys Asn Ile
    50              55              60

Ile Gln Phe Val His Gly Glu Glu Asp Leu Lys Val Gln His Ser Ser
65              70              75              80

Tyr Arg Gln Arg Ala Arg Leu Leu Lys Asp Gln Leu Ser Leu Gly Asn
            85              90              95

Ala Ala Leu Gln Ile Thr Asp Val Lys Leu Gln Asp Ala Gly Val Tyr
            100             105             110

Arg Cys Met Ile Ser Tyr Gly Gly Ala Asp Tyr Lys Arg Ile Thr Val
        115             120             125

Lys Val Asn Ala Pro Tyr Asn Lys Ile Asn Gln Arg Ile Leu Val Val
130             135             140

Asp Pro Val Thr Ser Glu His Glu Leu Thr Cys Gln Ala Glu Gly Tyr
145             150             155             160

Pro Lys Ala Glu Val Ile Trp Thr Ser Ser Asp His Gln Val Leu Ser
            165             170             175

Gly Lys Thr Thr Thr Thr Asn Ser Lys Arg Glu Glu Lys Leu Phe Asn
            180             185             190

Val Thr Ser Thr Leu Arg Ile Asn Thr Thr Thr Asn Glu Ile Phe Tyr
        195             200             205
```

TABLE 1-continued

```
Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245
```

SEQ ID NO: 5 Human PD-L1M cDNA Acid Sequence

```
cgaggctccg caccagccgc gcttctgtcc gcctgcaggg cattccagaa agatgagg      58
                                                        Met Arg
                                                            1 ata ttt gct gtc ttt ata ttc atg acc tac tgg cat ttg ctg aac gca    106
Ile Phe Ala Val Phe Ile Phe Met Thr Tyr Trp His Leu Leu Asn Ala
        5                  10                  15 ttt act gtc acg gtt ccc aag gac cta tat gtg gta gag tat ggt agc    154
Phe Thr Val Thr Val Pro Lys Asp Leu Tyr Val Val Glu Tyr Gly Ser
 20                  25                  30 aat atg aca att gaa tgc aaa ttc cca gta gaa aaa caa tta gac ctg    202
Asn Met Thr Ile Glu Cys Lys Phe Pro Val Glu Lys Gln Leu Asp Leu
 35                  40                  45                  50 gct gca cta att gtc tat tgg gaa atg gag gat aag aac att att caa    250
Ala Ala Leu Ile Val Tyr Trp Glu Met Glu Asp Lys Asn Ile Ile Gln
                 55                  60                  65 ttt gtg cat gga gag gaa gac ctg aag gtt cag cat agt agc tac aga    298
Phe Val His Gly Glu Glu Asp Leu Lys Val Gln His Ser Ser Tyr Arg
         70                  75                  80 cag agg gcc cgg ctg ttg aag gac cag ctc tcc ctg gga aat gct gca    346
Gln Arg Ala Arg Leu Leu Lys Asp Gln Leu Ser Leu Gly Asn Ala Ala
             85                  90                  95 ctt cag atc aca gat gtg aaa ttg cag gat gca ggg gtg tac cgc tgc    394
Leu Gln Ile Thr Asp Val Lys Leu Gln Asp Ala Gly Val Tyr Arg Cys
100                 105                 110 atg atc agc tat ggt ggt gcc gac tac aag cga att act gtg aaa gtc    442
Met Ile Ser Tyr Gly Gly Ala Asp Tyr Lys Arg Ile Thr Val Lys Val
115                 120                 125                 130 aat gcc cca tac aac aaa atc aac caa aga att ttg gtt gtg gat cca    490
Asn Ala Pro Tyr Asn Lys Ile Asn Gln Arg Ile Leu Val Val Asp Pro
                135                 140                 145 gtc acc tct gaa cat gaa ctg aca tgt cag gct gag ggc tac ccc aag    538
Val Thr Ser Glu His Glu Leu Thr Cys Gln Ala Glu Gly Tyr Pro Lys
            150                 155                 160 gcc gaa gtc atc tgg aca agc agt gac cat caa gtc ctg agt ggt aag    586
Ala Glu Val Ile Trp Thr Ser Ser Asp His Gln Val Leu Ser Gly Lys
        165                 170                 175 acc acc acc acc aat tcc aag aga gag gag aag ctt ttc aat gtg acc    634
Thr Thr Thr Thr Asn Ser Lys Arg Glu Glu Lys Leu Phe Asn Val Thr
180                 185                 190 agc aca ctg aga atc aac aca aca act aat gag att ttc tac tgc act    682
Ser Thr Leu Arg Ile Asn Thr Thr Thr Asn Glu Ile Phe Tyr Cys Thr
195                 200                 205                 210 ttt agg aga tta gat cct gag gaa aac cat aca gct gaa ttg gtc atc    730
Phe Arg Arg Leu Asp Pro Glu Glu Asn His Thr Ala Glu Leu Val Ile
                215                 220                 225 cca gaa cta cct ctg gca cat cct cca aat gaa agg act cac ttg gta    778
Pro Glu Leu Pro Leu Ala His Pro Pro Asn Glu Arg Thr His Leu Val
            230                 235                 240 att ctg gga gcc atc tta tta tgc ctt ggt gta gca ctg aca ttc atc    826
Ile Leu Gly Ala Ile Leu Leu Cys Leu Gly Val Ala Leu Thr Phe Ile
        245                 250                 255
```

TABLE 1-continued

```
ttc cgt tta aga aaa ggg aga atg atg gat gtg aaa aaa tgt ggc atc    874
Phe Arg Leu Arg Lys Gly Arg Met Met Asp Val Lys Lys Cys Gly Ile
    260                 265                 270 caa gat aca aac tca aag aag caa agt gat aca cat ttg gag gag acg    922
Gln Asp Thr Asn Ser Lys Lys Gln Ser Asp Thr His Leu Glu Glu Thr
275                 280                 285                 290 taatccagca ttggaacttc tgatcttcaa gcagggattc tcaacctgtg gtttaggggt   982
tcatcggggc tgagcgtgac aagaggaagg aatgggcccg tgggatgcag caatgtggg   1042 acttaaaagg cccaagcact gaaaatggaa cctggcgaaa gcagaggagg agaatgaaga  1102
aagatggagt caaacaggga gcctggaggg agaccttgat actttcaaat gcctgagggg  1162
ctcatcgacg cctgtgacag ggagaaagga tacttctgaa caaggagcct ccaagcaaat  1222
catccattgc tcatcctagg aagacgggtt gagaatccct aatttgaggg tcagttcctg  1282
cagaagtgcc ctttgcctcc actcaatgcc tcaatttgtt ttctgcatga ctgagagtct  1342
cagtgttgga acgggacagt atttatgtat gagtttttcc tatttatttt gagtctgtga  1402
ggtcttcttg tcatgtgagt gtggttgtga atgatttctt ttgaagatat attgtagtag  1462
atgttacaat tttgtcgcca aactaaactt gctgcttaat gatttgctca catctagtaa  1522
aacatggagt atttgtaaaa aaaaaaaaaa a                                  1553
```

SEQ ID NO: 6 Human PD-L1M Amino Acid Sequence

```
Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
             35                  40                  45

Asp Leu Ala Ala Leu Ile Val Tyr Trp Glu Met Glu Asp Lys Asn Ile
         50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255
```

TABLE 1-continued

```
Phe Ile Phe Arg Leu Arg Lys Gly Arg Met Met Asp Val Lys Lys Cys
            260                 265                 270

Gly Ile Gln Asp Thr Asn Ser Lys Gln Ser Asp Thr His Leu Glu
            275                 280                 285

Glu Thr
   290
```

SEQ ID NO: 7 Human PD-L2 cDNA Acid Sequence

```
atg atc ttc ctc ctg cta atg ttg agc ctg gaa ttg cag ctt cac cag      48
Met Ile Phe Leu Leu Leu Met Leu Ser Leu Glu Leu Gln Leu His Gln
 1               5                  10                  15 ata gca gct tta ttc aca gtg aca gtc cct aag gaa ctg tac ata ata      96
Ile Ala Ala Leu Phe Thr Val Thr Val Pro Lys Glu Leu Tyr Ile Ile
                20                  25                  30 gag cat ggc agc aat gtg acc ctg gaa tgc aac ttt gac act gga agt     144
Glu His Gly Ser Asn Val Thr Leu Glu Cys Asn Phe Asp Thr Gly Ser
             35                  40                  45 cat gtg aac ctt gga gca ata aca gcc agt ttg caa aag gtg gaa aat     192
His Val Asn Leu Gly Ala Ile Thr Ala Ser Leu Gln Lys Val Glu Asn
         50                  55                  60 gat aca tcc cca cac cgt gaa aga gcc act ttg ctg gag gag cag ctg     240
Asp Thr Ser Pro His Arg Glu Arg Ala Thr Leu Leu Glu Glu Gln Leu
 65                  70                  75                  80 ccc cta ggg aag gcc tcg ttc cac ata cct caa gtc caa gtg agg gac     288
Pro Leu Gly Lys Ala Ser Phe His Ile Pro Gln Val Gln Val Arg Asp
                 85                  90                  95 gaa gga cag tac caa tgc ata atc atc tat ggg gtc gcc tgg gac tac     336
Glu Gly Gln Tyr Gln Cys Ile Ile Ile Tyr Gly Val Ala Trp Asp Tyr
                100                 105                 110 aag tac ctg act ctg aaa gtc aaa gct tcc tac agg aaa ata aac act     384
Lys Tyr Leu Thr Leu Lys Val Lys Ala Ser Tyr Arg Lys Ile Asn Thr
            115                 120                 125 cac atc cta aag gtt cca gaa aca gat gag gta gag ctc acc tgc cag     432
His Ile Leu Lys Val Pro Glu Thr Asp Glu Val Glu Leu Thr Cys Gln
        130                 135                 140 gct aca ggt tat cct ctg gca gaa gta tcc tgg cca aac gtc agc gtt     480
Ala Thr Gly Tyr Pro Leu Ala Glu Val Ser Trp Pro Asn Val Ser Val
145                 150                 155                 160 cct gcc aac acc agc cac tcc agg acc cct gaa ggc ctc tac cag gtc     528
Pro Ala Asn Thr Ser His Ser Arg Thr Pro Glu Gly Leu Tyr Gln Val
                165                 170                 175 acc agt gtt ctg cgc cta aag cca ccc cct ggc aga aac ttc agc tgt     576
Thr Ser Val Leu Arg Leu Lys Pro Pro Pro Gly Arg Asn Phe Ser Cys
                180                 185                 190 gtg ttc tgg aat act cac gtg agg gaa ctt act ttg gcc agc att gac     624
Val Phe Trp Asn Thr His Val Arg Glu Leu Thr Leu Ala Ser Ile Asp
            195                 200                 205 ctt caa agt cag atg gaa ccc agg acc cat cca act tgg ctg ctt cac     672
Leu Gln Ser Gln Met Glu Pro Arg Thr His Pro Thr Trp Leu Leu His
        210                 215                 220 att ttc atc ccc tcc tgc atc att gct ttc att ttc ata gcc aca gtg     720
Ile Phe Ile Pro Ser Cys Ile Ile Ala Phe Ile Phe Ile Ala Thr Val
225                 230                 235                 240 ata gcc cta aga aaa caa ctc tgt caa aag ctg tat tct tca aaa gac     768
Ile Ala Leu Arg Lys Gln Leu Cys Gln Lys Leu Tyr Ser Ser Lys Asp
                245                 250                 255 aca aca aaa aga cct gtc acc aca aca aag agg gaa gtg aac agt gct     816
Thr Thr Lys Arg Pro Val Thr Thr Thr Lys Arg Glu Val Asn Ser Ala
                260                 265                 270 atc                                                                  819
Ile
```

TABLE 1-continued

SEQ ID NO: 8 Human PD-L2 Amino Acid Sequence

| | | | | | | | | | | | | | | |
|---|---|---|---|---|---|---|---|---|---|---|---|---|---|---|
| Met | Ile | Phe | Leu | Leu | Leu | Met | Leu | Ser | Leu | Glu | Leu | Gln | Leu | His | Gln |
| 1 | | | | 5 | | | | | 10 | | | | | 15 | |
| Ile | Ala | Ala | Leu | Phe | Thr | Val | Thr | Val | Pro | Lys | Glu | Leu | Tyr | Ile | Ile |
| | | | 20 | | | | 25 | | | | | 30 | | | |
| Glu | His | Gly | Ser | Asn | Val | Thr | Leu | Glu | Cys | Asn | Phe | Asp | Thr | Gly | Ser |
| | | 35 | | | | | 40 | | | | | 45 | | | |
| His | Val | Asn | Leu | Gly | Ala | Ile | Thr | Ala | Ser | Leu | Gln | Lys | Val | Glu | Asn |
| | 50 | | | | | 55 | | | | | 60 | | | | |
| Asp | Thr | Ser | Pro | His | Arg | Glu | Arg | Ala | Thr | Leu | Leu | Glu | Glu | Gln | Leu |
| 65 | | | | | 70 | | | | | 75 | | | | | 80 |
| Pro | Leu | Gly | Lys | Ala | Ser | Phe | His | Ile | Pro | Gln | Val | Gln | Val | Arg | Asp |
| | | | | 85 | | | | | 90 | | | | | 95 | |
| Glu | Gly | Gln | Tyr | Gln | Cys | Ile | Ile | Ile | Tyr | Gly | Val | Ala | Trp | Asp | Tyr |
| | | | | 100 | | | | | 105 | | | | | 110 | |
| Lys | Tyr | Leu | Thr | Leu | Lys | Val | Lys | Ala | Ser | Tyr | Arg | Lys | Ile | Asn | Thr |
| | | | 115 | | | | 120 | | | | | 125 | | | |
| His | Ile | Leu | Lys | Val | Pro | Glu | Thr | Asp | Glu | Val | Glu | Leu | Thr | Cys | Gln |
| | | 130 | | | | | 135 | | | | | 140 | | | |
| Ala | Thr | Gly | Tyr | Pro | Leu | Ala | Glu | Val | Ser | Trp | Pro | Asn | Val | Ser | Val |
| 145 | | | | | 150 | | | | | 155 | | | | | 160 |
| Pro | Ala | Asn | Thr | Ser | His | Ser | Arg | Thr | Pro | Glu | Gly | Leu | Tyr | Gln | Val |
| | | | | 165 | | | | | 170 | | | | | 175 | |
| Thr | Ser | Val | Leu | Arg | Leu | Lys | Pro | Pro | Pro | Gly | Arg | Asn | Phe | Ser | Cys |
| | | | 180 | | | | | 185 | | | | | 190 | | |
| Val | Phe | Trp | Asn | Thr | His | Val | Arg | Glu | Leu | Thr | Leu | Ala | Ser | Ile | Asp |
| | | 195 | | | | | 200 | | | | | 205 | | | |
| Leu | Gln | Ser | Gln | Met | Glu | Pro | Arg | Thr | His | Pro | Thr | Trp | Leu | Leu | His |
| | | 210 | | | | | 215 | | | | | 220 | | | |
| Ile | Phe | Ile | Pro | Ser | Cys | Ile | Ile | Ala | Phe | Ile | Phe | Ile | Ala | Thr | Val |
| 225 | | | | | 230 | | | | | 235 | | | | | 240 |
| Ile | Ala | Leu | Arg | Lys | Gln | Leu | Cys | Gln | Lys | Leu | Tyr | Ser | Ser | Lys | Asp |
| | | | | 245 | | | | | 250 | | | | | 255 | |
| Thr | Thr | Lys | Arg | Pro | Val | Thr | Thr | Thr | Lys | Arg | Glu | Val | Asn | Ser | Ala |
| | | | | 260 | | | | | 265 | | | | | 270 | |
| Ile | | | | | | | | | | | | | | | |

SEQ ID NO: 9 Human RGMb cDNA Sequence

```
  1 atgataagga agaagaggaa gcgaagcgcg ccccccggcc catgccgcag ccacgggccc
 61 agacccgcca cggcgcccgc gccgccgccc tcgccggagc ccacgagacc tgcatggacg
121 ggcatgggct tgagagcagc accttccagc gccgccgctg ccgccgccga ggttgagcag
181 cgccgcagcc ccgggctctg cccccgccg ctggagctgc tgctgctgct gctgttcagc
241 ctcgggctgc tccacgcagg tgactgccaa cagccagccc aatgtcgaat ccagaaatgc
301 accacggact tcgtgtccct gacttctcac ctgaactctg ccgttgacgg cttttgactct
361 gagttttgca aggccttgcg tgcctatgct ggctgcaccc agcgaacttc aaaagcctgc
421 cgtggcaacc tggtatacca ttctgccgtg ttgggtatca gtgacctcat gagccagagg
481 aattgttcca aggatggacc cacatcctct accaaccccg aagtgaccca tgatccttgc
541 aactatcaca gccacgctgg agccaggaa cacaggagag ggaccagaa ccctcccagt
601 tacctttttt gtggcttgtt tggagatcct cacctcagaa ctttcaagga taacttccaa
661 acatgcaaag tagaagggc ctggccactc atagataata attatctttc agttcaagtg
721 acaaacgtac ctgtggtccc tggatccagt gctactgcta caaataagat cactattatc
```

TABLE 1-continued

```
 781 ttcaaagccc accatgagtg tacagatcag aaagtctacc aagctgtgac agatgacctg
 841 ccggccgcct ttgtgatgg caccaccagt ggtggggaca gcgatgccaa gagcctgcgt
 901 atcgtggaaa gggagagtgg ccactatgtg gagatgcacg cccgctatat agggaccaca
 961 gtgtttgtgc ggcaggtggg tcgctacctg acccttgcca tccgtatgcc tgaagacctg
1021 gccatgtcct acgaggagag ccaggacctg cagctgtgcg tgaacggctg ccccctgagt
1081 gaacgcatcg atgacgggca gggccaggtg tctgccatcc tgggacacag cctgcctcgc
1141 acctccttgg tgcaggcctg gcctggctac acactggaga ctgccaacac tcaatgccat
1201 gagaagatgc cagtgaagga catctatttc cagtcctgtg tcttcgacct gctcaccact
1261 ggtgatgcca actttactgc cgcagcccac agtgccttgg aggatgtgga ggccctgcac
1321 ccaaggaagg aacgctggca cattttcccc agcagtggca atgggactcc ccgtggaggc
1381 agtgatttgt ctgtcagtct aggactcacc tgcttgatcc ttatcgtgtt tttgtag
```

SEQ ID NO: 10 Human RGMb Amino Acid Sequence
```
   1 mirkkrkrsa ppgpershgp rpatapappp speptrpawt gmglraapss aaaaaaeveq
  61 rrspglcppp lelllllfs lgllhagdcq qpaqcriqkc ttdfvsltsh lnsavdgfds
 121 efckalraya gctqrtskac rgnlvyhsav lgisdlmsqr ncskdgptss tnpevthdpc
 181 nyhshagare hrrgdqnpps ylfcglfgdp hlrtfkdnfq tckvegawpl idnnylsvqv
 241 tnvpvvpgss atatnkitii fkahhectdq kvyqavtddl paafvdgtts ggdsdakslr
 301 iveresghyv emharyigtt vfvrqvgryl tlairmpedl amsyeesqdl qlcvngcpls
 361 eriddgqgqv sailghslpr tslvqawpgy tletantqch ekmpvkdiyf qscvfdlltt
 421 gdanftaaah saledvealh prkerwhifp ssgngtprgg sdlsyslglt clilivfl
```

SEQ ID NO: 11 Human B7-1 cDNA Sequence
```
   1 atgggccaca cacggaggca gggaacatca ccatccaagt gtccatacct caatttcttt
  61 cagctcttgg tgctggctgg tctttctcac ttctgttcag tgttatcca cgtgaccaag
 121 gaagtgaaag aagtggcaac gctgtcctgt ggtcacaatg tttctgttga agagctggca
 181 caaactcgca tctactggca aaaggagaag aaaatggtgc tgactatgat gtctggggac
 241 atgaatatat ggcccgagta caagaaccgg accatctttg atatcactaa taacctctcc
 301 attgtgatcc tggctctgcg cccatctgac gagggcacat acgagtgtgt tgttctgaag
 361 tatgaaaaag acgctttcaa gcgggaacac ctggctaagt gacgttatc agtcaaagct
 421 gacttcccta cacctagtat atctgacttt gaaattccaa cttctaatat tagaaggata
 481 atttgctcaa cctctggagg ttttccagag cctcacctct cctggttgga aaatggagaa
 541 gaattaaatg ccatcaacac aacagtttcc caagatcctg aaactgagct ctatgctgtt
 601 agcagcaaac tggatttcaa tatgacaacc aaccacagct tcatgtgtct catcaagtat
 661 ggacatttaa gagtgaatca gaccttcaac tggaatacaa ccaagcaaga gcatttcct
 721 gataacctgc tcccatcctg ggccattacc ttaatctcag taaatggaat ttttgtgata
 781 tgctgcctga cctactgctt tgccccaaga tgcagagaga aggaggaa tgagagattg
 841 agaagggaaa gtgtacgccc tgtataa
```

SEQ ID NO: 12 Human B7-1 Amino Acid Sequence
```
   1 mghtrrqgts pskcpylnff qllvlaglsh fcsgvihvtk evkevatlsc ghnvsveela
  61 qtriywqkek kmvltmmsgd mniwpeyknr tifditnnls ivilalrpsd egtyecvvlk
 121 yekdafkreh laevtlsvka dfptpsisdf eiptsnirri icstsggfpe phlswlenge
 181 elnainttvs qdpetelyav ssklDfnmtt nhsfmcliky ghlrvnqtfn wnttkqehfp
 241 dnllpswait lisvngifvi ccltycfapr crerrrnerl rresvrpv
```

TABLE 1-continued

1B9 Light Chain Variable (vK) DNA and Amino Acid Sequences
LOCUS       1B9_VK    321 bp  DNA   linear
DEFINITION  1B9, DNA 321 bases.
FEATURES         Location/Qualifiers
J_segment        292..321
                 /label = JK
V_segment        265..291
                 /label = CDR3
V_region         169..264
                 /label = FWR3
V_segment        148..168
                 /label = CDR2
V_region         103..147
                 /label = FWR2
V_segment        70..102
                 /label = CDR1
V_region         1..69
                 /label = FWR1
CDS              1..321
                 /label = 1B9\VK
/translation = "DIVMTQSHKFMSTSLGDRVTITCKASQDVGISVVWYQQKPG
QSPKLLIYWASTRHTGVPDRFTGSGSGTDFTLTINNVQSEDLADYFCQQYSSYPL
TVGAGTKLELK" (SEQ ID NO: 14)

BASE COUNT 85 a 81 c 77 g 78 t
ORIGIN
    1 gacattgtga tgacccagtc tcacaaattc atgtccacat cactaggaga cagggtcacc 61 atcacctgca aggccagtca ggatgtgggt atttctgtag tttggtatca acagaaacca 121 gggcaatctc ctaaactact gatttactgg gcatccaccc ggcacactgg agtccctgat 181 cgcttcacag gcagtggatc tgggacagat tcactctga ccattaacaa tgtgcagtct 241 gaagacttgg cagattattt ctgtcagcaa tatagcagct atccgctcac ggtcggtgct 301 gggaccaagc tggagctgaa a (SEQ ID NO: 13)

1B9 Heavy Chain Variable DNA and Amino Acid Sequences
LOCUS       1B9_VH    363 bp  DNA   linear
DEFINITION  1B9, DNA 363 bases.
FEATURES         Location/Qualifiers
J_segment        331..363
                 /label = JH
V_segment        295..330
                 /label = CDR3
V_region         199..294
                 /label = FWR3
V_segment        151..198
                 /label = CDR2
V_region         109..150
                 /label = FWR2
V_segment        91..108
                 /label = CDR1
V_region         1..90
                 /label = FWR1
CDS              1..363
                 /label = 1B9\VH
/translation = "DVQLQESGPGLVKPSQSLSLTCTVTGYSITSDHAWNWIRQ
VPGNKLEWMGYITYRGSTTYSPSLKSRISITRDTSKNQFFLQLNSVTTEDTATY
YCARSMITTGYYVMDYWGQGTSVTVSS" (SEQ ID NO: 16)

BASE COUNT 92 a 99 c 82 g 90 t
ORIGIN
    1 gatgtgcagc ttcaggagtc gggacctggc ctggtgaaac cttctcagtc tctgtccctc 61 acctgcactg tcactggcta ctcaatcacc agtgatcatg cctggaactg gatccggcag 121 gttccaggaa acaaactgga gtggatgggc tacataacct accgtggtag cactacctat 181 agcccatctc tcaaaagtcg aatttctatc actcgagaca catccaagaa ccagttcttc 241 ctgcagttga attctgtgac tactgaggac acagccacat attactgtgc aagatctatg 301 attacgacgg ggtactatgt tatggactac tggggtcaag aacctcagt caccgtctcc 361 tca (SEQ ID NO: 15)

TABLE 1-continued

```
4H1 Light Chain Variable (vK) DNA and Amino Acid Sequences
LOCUS      4H1_VK 321 bp DNA linear
DEFINITION 4H1, DNA 321 bases.
FEATURES   Location/Qualifiers
J_segment  292..321
           /label = JK
V_segment  265..291
           /label = CDR3
V_region   169..264
           /label = FWR3
V_segment  148..168
           /label = CDR2
V_region   103..147
           /label = FWR2
V_segment  70..102
           /label = CDR1
V_region   1..69
           /label = FWR1
CDS        1..321
           /label = 4H1\VK
/translation = "DIVMTQSHKFMSTSVGDRVSISCKASQDVGISVAWYQQKP
GQSPKLLIYWASTRHTGVPVRFTGSGSGTDFTLTISNVQSEDLADYFCQQYSSY
PPTFGAGTKLELK" (SEQ ID NO: 18)

BASE COUNT 82 a 81 c 79 g 79 t
ORIGIN
    1 gacattgtga tgacccagtc tcacaaattc atgtccacat cagtaggaga cagggtcagc 61 atctcctgca aggccagtca ggatgtgggt atttctgtag cctggtatca acagaaacca 121 gggcaatctc ctaaactact gatttactgg gcatccaccc ggcacactgg agtccctgtt 181 cgcttcacag gcagtggatc tgggacagat ttcactctca ccataagcaa tgtgcagtct 241 gaagacttgg cagattattt ttgtcagcag tatagcagtt atccgcccac gttcggtgct 301 gggaccaagc tggagctgaa a (SEQ ID NO: 17)

4H1 Heavy Chain Variable DNA and Amino Acid Sequences
LOCUS      4H1_VH 363 bp DNA linear
DEFINITION 4H1, DNA 363 bases.
FEATURES   Location/Qualifiers
J_segment  331..363
           /label = JH
V_segment  295..330
           /label = CDR3
V_region   199..294
           /label = FWR3
V_segment  151..198
           /label = CDR2
V_region   109..150
           /label = FWR2
V_segment  91..108
           /label = CDR1
V_region   1..90
           /label = FWR1
CDS        1..363
           /label = 4H1\VH
/translation = "DVQLQESGPGLVKPSQSLSLTCTVTDYSITSDYAWTWIRQ
FPGNKLEWMGYITYRGTTRYNPSLTSRISFTRDTSKNQLFLQLNSVTTEDTGTY
CCARSMITTGYYAMDYWGQGTSVTVSS" (SEQ ID NO: 20)

BASE COUNT 90 a 103 c 82 g 88 t
ORIGIN
    1 gatgtgcagc ttcaggagtc gggacctggc ctggtgaaac cttctcagtc tctgtccctc 61 acctgcactg tcactgacta ctcaatcacc agtgattatg cctggacctg gatccggcag 121 tttccgggaa acaaactgga gtggatgggc tacataacct acagaggtac cactcgctac 181 aacccatctc tcacaagtcg aatctctttc actcgagaca catccaagaa ccagctcttc 241 ctgcagttga attctgtgac tactgaggac acaggcacat attgctgtgc aagatctatg 301 attacgacgg ggtactatgc tatggactac tggggtcaag gaacctcagt caccgtctcc 361 tca (SEQ ID NO: 19)
```

Various aspects of the invention are described in further detail in the following subsections.

I. Isolated Nucleic Acid Molecules

One aspect of the invention pertains to isolated nucleic acid molecules that encode polypeptides of the present invention (e.g., including the sequences in Table 1) or biologically active portions thereof, as well as nucleic acid fragments sufficient for use as hybridization probes to identify nucleic acid molecules encoding these polypeptides and fragments for use as PCR primers for the amplification or mutation of the nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. In some embodiments an "isolated" nucleic acid molecule is free of sequences which naturally flank the nucleic acid (i.e., sequences located at the 5' and 3' ends of the nucleic acid molecule) in the genomic DNA of the organism from which the nucleic acid is derived. For example, an "isolated" nucleic acid molecule, such as a cDNA molecule, can be substantially free of other cellular material, or culture medium, when produced by recombinant techniques, or substantially free of chemical precursors or other chemicals when chemically synthesized.

A nucleic acid molecule of the present invention (e.g., including the sequences in Table 1), or a portion thereof, can be isolated using standard molecular biology techniques and the sequence information provided herein. For example, a nucleic acid molecule encompassing all or a portion of sequences shown in Table 1 can be isolated by the polymerase chain reaction (PCR) using synthetic oligonucleotide primers designed based upon the sequences shown in Table 1.

A nucleic acid molecule of the invention can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleic acid sequences of the invention can be prepared by standard synthetic techniques, e.g., using an automated DNA synthesizer.

In another embodiment, an isolated nucleic acid molecule of the invention comprises a nucleic acid molecule which is a complement of a nucleic acid molecule of the present invention (e.g., including the sequences in Table 1), or a portion thereof. A nucleic acid molecule which is complementary to a nucleic acid molecule of the present invention (e.g., including the sequences in Table 1), or a portion thereof, is one which is sufficiently complementary to the nucleotide sequence shown in Table 1, such that it can hybridize to the respective nucleotide sequence shown in Table 1, thereby forming a stable duplex.

In still another embodiment, an isolated nucleic acid molecule of the present invention comprises a nucleotide sequence which is at least about 70%, 75%, 80%, 85%, 90%, 91%, 92%, 93%, 94%, 95%, 96%, 97%, 98%, 99% or more identical to the entire length of the nucleotide sequence shown in Table 1, or a portion of any of these nucleotide sequences.

Moreover, the nucleic acid molecule of the invention can comprise only a portion of a nucleic acid molecule of the present invention (e.g., including the sequences in Table 1), or a portion thereof, for example, a fragment which can be used as a probe or primer or a fragment which encodes a portion of a polypeptide of the invention, e.g., those in Table 1. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a nucleic acid molecule of the present invention (e.g., including the sequences in Table 1); of an anti-sense sequence of a nucleic acid molecule of the present invention (e.g., including the sequences in Table 1); or of a mutant of a nucleic acid molecule of the present invention (e.g., including the sequences in Table 1).

Probes based on a nucleic acid molecule of the present invention (e.g., including the sequences in Table 1) can be used to detect transcripts or genomic sequences encoding the same or homologous polypeptides. In one embodiment, the probe further comprises a label group attached thereto, e.g., the label group can be a radioisotope, a fluorescent compound, an enzyme, or an enzyme co-factor.

A nucleic acid fragment encoding a "biologically active portion of a polypeptide of the invention" can be prepared by isolating a portion of the nucleotide sequence of a nucleic acid molecule of the present invention (e.g., including the sequences in Table 1) which encodes a polypeptide having a biological activity of a polypeptide of the invention (e.g., the ability to bind to its antigenic target), expressing the encoded portion of the polypeptide of the invention (e.g., by recombinant expression in vitro) and assessing the activity of the encoded portion of the polypeptide of the invention.

In other embodiments, a nucleic acid fragment encoding a "peptide epitope of the invention" can be prepared by isolating a portion of the nucleotide sequence of a nucleic acid molecule of the present invention (e.g., including the sequences in Table 1) which encodes a polypeptide for which antibodies raised against the polypeptide will be specific (e.g., the human PD-L1 and PD-L2 peptide epitopes shown in Table 1).

The invention further encompasses nucleic acid molecules that differ from nucleotide sequence(s) shown in Table 1 due to degeneracy of the genetic code and thus encode the same polypeptides as those encoded by the respective nucleotide sequence shown in Table 1. In another embodiment, an isolated nucleic acid molecule of the invention has a nucleotide sequence encoding a polypeptide of the present invention (e.g., including the sequences in Table 1).

Nucleic acid molecules corresponding to homologues of a nucleic acid molecule of the present invention (e.g., including the sequences in Table 1) can be isolated based on their homology to the nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising a nucleic acid molecule of the present invention (e.g., including the sequences in Table 1).

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A non-limiting example of stringent hybridization conditions includes hybridization in 4× or 6× sodium chloride/sodium citrate (SSC), at about 65-70° C. (or hybridization in 4×SSC plus 50% formamide at about 42-50° C.) followed by one or more washes in 1×SSC, at about 65-70° C. A further non-limiting example of stringent hybridization conditions includes hybridization at 6×SSC at 45° C., followed by one or more washes in 0.2×SSC, 0.1% SDS at 65° C. A non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A non-limiting example of reduced stringency hybridization conditions includes hybridization in 4× or 6×SSC, at about 50-60° C. (or alternatively hybridization in 6×SSC plus 50% formamide at about 40-45° C.) followed by one or more washes in 2×, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(#of A+T bases)+4(#of G+C bases). For hybrids between 18 and 49 base pairs in length, $T_m$ (° C.)=81.5+16.6($\log_{10}[Na^+]$)+0.41(% G+C)−(600/N), where N is the number of bases in the hybrid, and [$Na^+$] is the concentration of sodium ions in the hybridization buffer ([$Na^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C., see e.g., Church and Gilbert (1984) Proc. Natl. Acad. Sci. USA 81:1991-1995 (or alternatively 0.2×SSC, 1% SDS).

The skilled artisan will further appreciate that changes can be introduced by mutation into a nucleic acid molecule of the present invention (e.g., including the sequences in Table 1), thereby leading to changes in the amino acid sequence of the encoded polypeptides of the present invention, without altering the functional ability of the polypeptides. For example, nucleotide substitutions leading to amino acid substitutions at "non-essential" amino acid residues can be made in a nucleic acid molecule of the present invention (e.g., including the sequences in Table 1). A "non-essential" amino acid residue is a residue that can be altered from a nucleic acid molecule of the present invention (e.g., including the sequences in Table 1) without altering the biological activity, whereas an "essential" amino acid residue is required for biological activity. For example, amino acid residues that are conserved among the polypeptides of the present invention, e.g., those required for binding of the polypeptides to its target antigen, are predicted to be particularly unamenable to alteration.

Accordingly, another aspect of the invention pertains to nucleic acid molecules encoding polypeptides of the present invention (e.g., including the sequences in Table 1) that contain changes in amino acid residues that are not essential for activity. Such polypeptides differ in amino acid sequence from the sequences in Table 1, or portions thereof, yet retain biological activity. In one embodiment, the isolated nucleic acid molecule comprises a nucleotide sequence encoding a polypeptide, wherein the polypeptide comprises an amino acid sequence at least about 71%, 75%, 80%, 85%, 90%, 91%, 92%, 93%, 94%, 95%, 96%, 97%, 98%, 99% or more identical to the sequences in Table 1, or portions thereof.

An isolated nucleic acid molecule encoding a polypeptide identical to the polypeptides of the sequences in Table 1, or portions thereof, can be created by introducing one or more nucleotide substitutions, additions or deletions into the nucleotide sequence of the sequences in Table 1, or portions thereof, such that one or more amino acid substitutions, additions or deletions are introduced into the encoded polypeptide. Mutations can be introduced into nucleic acid molecules of the present invention (e.g., including the sequences in Table 1) by standard techniques, such as site-directed mutagenesis and PCR-mediated mutagenesis. In one embodiment, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a polypeptide of the invention (e.g., including the sequences in Table 1) can be replaced with another amino acid residue from the same side chain family. Alternatively, in another embodiment, mutations can be introduced randomly along all or part of a nucleic acid molecule(s) of the present invention (e.g., including the sequences in Table 1), such as by saturation mutagenesis, and the resultant mutants can be screened for biological activity to identify mutants that retain activity. Following mutagenesis of a nucleic acid molecule of the present invention (e.g., including the sequences in Table 1), the encoded polypeptide can be expressed recombinantly and the activity of the polypeptide can be determined.

In one embodiment, a mutant polypeptide of the invention can be assayed for the ability to bind to and/or modulate the activity of PD-L1 and/or PD-L2.

Yet another aspect of the invention pertains to isolated nucleic acid molecules encoding fusion proteins. Such nucleic acid molecules, comprising at least a first nucleotide sequence encoding a polypeptide of the invention (e.g., including the sequences in Table 1) operatively linked to a second nucleotide sequence encoding a polypeptide of the invention (e.g., including the sequences in Table 1) can be prepared by standard recombinant DNA techniques.

The expression characteristics of a nucleic acid molecules of the present invention (e.g., including the sequences in Table 1) within a cell line or microorganism may be modified by inserting a heterologous DNA regulatory element into the genome of a stable cell line or cloned microorganism such that the inserted regulatory element is operatively linked with a nucleic acid molecule of the present invention (e.g., including the sequences in Table 1). For example, a heterologous regulatory element may be inserted into a stable cell line or cloned microorganism, such that it is operatively linked with a nucleic acid molecule of the present invention (e.g., including the sequences in Table 1), using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated Polypeptide Molecules

One aspect of the invention pertains to isolated polypeptides of the present invention (e.g., including the sequences in Table 1) and biologically active portions thereof. In one embodiment, polypeptides of the present invention (e.g., including the sequences in Table 1), and biologically active portions thereof can be isolated from cells or tissue sources by an appropriate purification scheme using standard protein purification techniques. In another embodiment, polypeptides of the present invention (e.g., including the sequences in Table 1), and biologically active portions thereof are produced by recombinant DNA techniques. Alternatively, polypeptides of the present invention (e.g., including the sequences in Table 1), and biologically active portions thereof can be chemically synthesized using standard peptide synthesis techniques.

An "isolated" or "purified" polypeptide or biologically active portion thereof is substantially free of cellular material or other contaminating proteins from the cell or tissue source from which the polypeptides of the present invention (e.g., including the sequences in Table 1) is derived, or substantially free from chemical precursors or other chemicals when chemically synthesized. The language "substantially free of cellular material" includes preparations of polypeptide(s) of the present invention (e.g., including the sequences in Table 1), and biologically active portions thereof, in which the polypeptide is separated from cellular components of the cells from which it is isolated or recombinantly produced. In one embodiment, the language "substantially free of cellular material" includes preparations of polypeptide(s) of the present invention (e.g., including the sequences in Table 1), and biologically active portions thereof having less than about 30% (by dry weight) of proteins not of the present invention (also referred to herein as a "contaminating protein"), more preferably less than about 20% of proteins not of the present invention, still more preferably less than about 10% of proteins not of the present invention, and most preferably less than about 5% of proteins not of the present invention. When polypeptides of the present invention (e.g., including the sequences in Table 1) or biologically active portion thereof are recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of polypeptide(s) of the present invention (e.g., including the sequences in Table 1) or biologically active portion thereof in which the polypeptide is separated from chemical precursors or other chemicals which are involved in the synthesis of the polypeptide. In one embodiment, the language "substantially free of chemical precursors or other chemicals" includes preparations of polypeptide(s) of the present invention (e.g., including the sequences in Table 1) or biologically active portion thereof having less than about 30% (by dry weight) of chemical precursors or of proteins not of the present invention, more preferably less than about 20% chemical precursors or of proteins not of the present invention, still more preferably less than about 10% chemical precursors or of proteins not of the present invention, and most preferably less than about 5% chemical precursors or of proteins not of the present invention.

As used herein, a "biologically active portion" of polypeptide(s) of the present invention (e.g., including the sequences in Table 1) include polypeptides which participate in an interaction between PD-L1 and its receptors, as well as PD-L2 and its receptors. In some embodiments, PD-L1 and/or PD-L2 are the human orthologs. Biologically active portions of a polypeptide(s) of the present invention (e.g., including the sequences in Table 1) include peptides comprising amino acid sequences sufficiently identical to or derived from the amino acid sequence of polypeptide(s) of the present invention (e.g., including the sequences in Table 1), which include fewer amino acids than the respective, full length polypeptide(s) of the present invention (e.g., including the sequences in Table 1), and exhibit at least one activity of the respective polypeptide(s) of the present invention (e.g., including the sequences in Table 1). In one embodiment, biologically active portions comprise a domain or motif with the ability to specifically bind PD-L1 and/or PD-L2 according to the antigen, respectively, to which it was raised or designed to bind.

In another embodiment, polypeptide(s) of the present invention (e.g., including the sequences in Table 1) has an amino acid sequence shown in Table 1. In other embodiments, the polypeptide is substantially identical to polypeptide(s) shown in Table 1, and retains the functional activity of the respective polypeptide(s) shown in Table 1, yet differs in amino acid sequence due to mutagenesis, as described in detail herein. Accordingly, in another embodiment, a polypeptide(s) of the present invention is a polypeptide which comprises an amino acid sequence at least about 71%, 75%, 80%, 85%, 90%, 91%, 92%, 93%, 94%, 95%, 96% 97%, 98%, 99%, 99.5%, or 99.9% or more identical to a polypeptide(s) shown in Table 1.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In one embodiment, the length of a reference sequence aligned for comparison purposes is at least 30%, preferably at least 40%, more preferably at least 50%, even more preferably at least 60%, and even more preferably at least 70%, 80%, 90%, 95%, 96%, 97%, 98%, 99%, 99.5%, or 99.9% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also provides chimeric or fusion proteins. As used herein, a "chimeric protein" or "fusion protein" comprises a polypeptide(s) of the present invention (e.g., including the sequences in Table 1) operatively linked to a polypeptide not of the present invention. A "polypeptide(s) of the present invention" refers to a polypeptide having an amino acid sequence corresponding to a polypeptide shown in Table 1, whereas a "polypeptide not of the present invention" refers to a polypeptide not having an amino acid sequence corresponding to a polypeptide which is not substantially homologous to a polypeptide shown in Table 1, e.g., a polypeptide which is different from a polypeptide shown in Table 1 and which is derived from the same or a different organism. Within the fusion protein, the term "operatively linked" is intended to indicate that the polypeptide(s) of the present invention and the polypeptide(s) not of the present invention are fused in-frame to each other. The polypeptide(s) not of the present invention can be fused to the N-terminus or C-terminus of the polypeptide(s) of the present invention and corresponds to a moiety that alters the solubility, binding affinity, stability, or valency of the polypeptide(s) of the present invention.

For example, in one embodiment, the fusion protein is a GST fusion protein with a polypeptide(s) of the present invention. Such fusion proteins can facilitate the purification of recombinant polypeptides of the invention. In another embodiment, the fusion protein contains a heterologous signal sequence at its N-terminus. In yet another embodiment, the fusion protein contains a cytotoxic moiety (e.g., toxin). In certain host cells (e.g., mammalian host cells), expression and/or secretion of polypeptide(s) of the present invention can be increased through use of a heterologous signal sequence.

A chimeric or fusion polypeptide(s) of the present invention (e.g., including the sequences in Table 1) can be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, Ausubel et al., eds., John Wiley & Sons: 1992). Moreover, many expression vectors are commercially available that already encode a fusion moiety (e.g., a GST polypeptide).

The amino acid sequences of polypeptide(s) of the present invention (e.g., including the sequences in Table 1) identified herein will enable those of skill in the art to produce polypeptides corresponding to polypeptide(s) of the present invention (e.g., including the sequences in Table 1). Such polypeptides can be produced in prokaryotic or eukaryotic host cells by expression of polynucleotides encoding a polypeptide(s) of the present invention (e.g., including the sequences in Table 1). Alternatively, such peptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu. Rev. Biochem. 57:957; and Offord, R. E. (1980) Semisynthetic Proteins, Wiley Publishing, which are incorporated herein by reference).

III. Antibodies That Bind Both PD-L1 and PD-L2

Without being bound by theory, and offered to improve the understanding of the disclosed invention, it is believed that the antibodies of the present invention are unique relative to known PD-L1 or PD-L2 binding antibodies within at least one of the CDRs (complementarity determining regions) which participate in binding to the PD-L1 and PD-L2 polypeptide, at least because existing PD-L1 or PD-L2 binding antibodies do not have binding affinity for both PD-L1 and PD-L2. This belief is based in part on the well known structural arrangement of elements, including the CDR containing hypervariable regions, of an antibody's structure. Antibodies of the present invention may also differ from known PD-L1 and/or PD-L2 binding antibodies at more than one CDR and/or at more than one amino acid position within one or more CDR. These differences may provide the antibodies of the disclosed invention with the characteristic of binding to conserved epitopes of both PD-L1 and PD-L2 relative to previous antibodies against PD-L1 and/or PD-L2. In one embodiment, antibodies of the present invention specifically bind to the conserved PD-L1 and PD-L2 peptide sequences, CFTVTVPKDLY-VVEYGSN and CYRSMISYGGADYKRITV, which represent immunogenic epitopes for generating desired dual binding antibodies based on structural and sequence conservation analysis between PD-L1 and PD-L2, as well as the binding relationships between PD-1 and its ligands, PD-L1 and PD-L2. Accordingly, the antibodies of the present invention recognize both PD-L1 and PD-L2 with higher specificity and/or sensitivity relative to known PD-L1 or PD-L2 antibodies. Such antibodies are suitable for, among other uses Western blotting (or immunoblotting), immunohistochemistry (IHC), detection of denatured or fixed forms of PD-L1 and/or PD-L2, ELISA assays, and RIA assays.

In preferred embodiments, the antibodies of the present invention and antigen-binding fragments thereof may also inhibit (block) PD-L1 and/or PD-L2 activity and so act as PD-L1 and/or PD-L2 inhibitors. Such antibodies, and fragments, may be used to both detect the presence of PD-L1 and/or PD-L2 and to inhibit PD-L1 and/or PD-L2 activity without the need for introduction of an additional PD-L1 and/or PD-L2 inhibitor. Alternatively, a PD-L1 and/or PD-L2 inhibitory antibody or antigen-binding fragment thereof may be used in combination with another PD-L1 and/or PD-L2 inhibitor, such as in a composition for inhibiting PD-L1 and/or PD-L2 activity or as administered, separately or in combination, to a subject as part of a method to inhibit PD-L1 and/or PD-L2 activity.

Monoclonal antibodies of the invention can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

One method for generating hybridomas which produces monoclonal antibodies of the invention is the murine system. Hybridoma production in the mouse is well known in the art, including immunization protocols and techniques for isolating and fusing immunized splenocytes.

Polyclonal antibodies can be prepared by immunizing a suitable subject with a polypeptide immunogen (e.g., those listed in Table 1). However, conventional immunization protocols, as those used in the field to date, will not generate desired anti-PD-L1/PD-L2 antibodies with any reasonable expectation of success. Specifically, immunization of normal wild-type host animals will delete antibodies that react against host PD-L1 and/or PD-L2 and thereby delete a large number of B cells and antibodies produced therefrom that bind to structures conserved between the host PD-L1 and/or PD-L2 and the immunizing PD-L1 and/or PD-L2 sequences. Accordingly, it has been discovered herein that immunization of host animals having a genetic knockout for both PD-L1 and PD-L2 (i.e., double genetic knockouts) such that PD-L1 and PD-L2 polypeptides are not expressed inhibits or prevents tolerization and deletion of B cells producing cross-reactive antibodies that bind to immunizing PD-L1 and PD-L2 sequences.

A variety of immunization and boosting approaches can be used to generate an immune response containing desired PD-L1/PD-L2 antibodies, including traditional immunization schedules (typically two immunizations in the first four to five weeks, followed by additional immunizations if the desired titer is not achieved), with a final boost three to four days prior to harvest of cells for cloning and antibody isolation. Additional approaches include the rapid immunization in multiple sites, or RIMMS immunization protocol (see Kilpatrick et al. (1997) *Hybridoma* 16(4):381-9 and Bynum et al. (1999) *Hybridoma* 19(5):407-11). Additionally, immunization/boosting approaches may be adapted by the use of a combination of immunogens, including soluble extracellular domain fragments of PD-L1 and/or PD-L2, cells engineered to express high levels of PD-L1 and/or PD-L2 on their surface, purified solubilized PD-L1 or PD-L2, and peptides derived from PD-L1 and/or PD-L2 (e.g., see Table 1).

The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci. Chem.* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating an anti-PD-L1 and/or PD-L2 monoclonal antibody (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology (NY)* 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology (NY)* 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-PD-L1/PD-L2 dual binding antibodies, such as chimeric, composite, and humanized monoclonal antibodies, which can be made using standard recombinant DNA techniques, can be generated. Such chimeric, composite, and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125, 023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225, 539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology (NY)* 12:396-399; Chen, S-Y. et al. (1994) *Hum. Gene Ther.* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

In another embodiment, human monoclonal antibodies directed against PD-L1 and PD-L2 can be generated using transgenic or transchromosomal mice carrying parts of the human immune system rather than the mouse system. In one embodiment, transgenic mice, referred to herein as "HuMAb mice" which contain a human immunoglobulin gene mini-loci that encodes unrearranged human heavy (μ and γ) and κ light chain immunoglobulin sequences, together with targeted mutations that inactivate the endogenous μ and κ chain loci (Lonberg, N. et al. (1994) Nature 368(6474): 856 859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49 101; Lonberg, N. and Huszar, D. (1995) Intern. Rev. Immunol. Vol. 13: 65 93, and Harding, F. and Lonberg, N. (1995) Ann. N. Y Acad. Sci 764:536 546). The preparation of HuMAb mice is described in Taylor, L. et al. (1992) Nucleic Acids Research 20:6287 6295; Chen, J. et al. (1993) International Immunology 5: 647 656; Tuaillon et al. (1993) Proc. Natl. Acad. Sci USA 90:3720 3724; Choi et al. (1993) Nature Genetics 4:117 123; Chen, J. et al. (1993) EMBO J. 12: 821 830; Tuaillon et al. (1994) J. Immunol. 152:2912 2920; Lonberg et al., (1994) Nature 368(6474): 856 859; Lonberg, N. (1994) Handbook of Experimental Pharmacology 113:49 101; Taylor, L. et al. (1994) International Immunology 6: 579 591; Lonberg, N. and Huszar, D. (1995) Intern. Rev. Immunol. Vol. 13: 65 93; Harding, F. and Lonberg, N. (1995) Ann. N.Y. Acad. Sci 764:536 546; Fishwild, D. et al. (1996) Nature Biotechnology 14: 845 851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992.

In another embodiment, an antibody for use in the invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to PD-L1 and PD-L2. In one embodiment, the bispecific antibody could specifically bind to both PD-L1 and PD-L2, in addition to other desirable targets, such as other co-immunoinhibitory polypeptides (e.g., CTLA4, B7-1, PD-1, and the like).

Yet another aspect of the invention pertains to anti-PD-L1/PD-L2 polypeptide antibodies that are obtainable by a process comprising, immunizing an animal with an immunogenic PD-L1 and PD-L2 polypeptide or immunogenic portions thereof (e.g., polypeptides shown in Table 1), and then isolating from the animal antibodies that specifically bind to the polypeptide.

In still another aspect of the invention, partial or known antibody sequences can be used to generate and/or express new antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L et al., 1998, Nature 332:323 327; Jones, P. et al., 1986, Nature 321:522 525; and Queen, C. et al., 1989, Proc. Natl. Acad. See. U.S.A. 86:10029 10033). Such framework sequences can be obtained from public DNA databases that include germline or non-germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody. Partial heavy and light chain sequence spanning the CDR regions is typically sufficient for this purpose. The partial sequence is used to determine which germline and/or non-germline variable and joining gene segments contributed to the recombined antibody variable genes. The germline and/or non-germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons. The process can also be used to screen libraries of particular immunoglobulin encoding sequences in one species (e.g., human) to design cognate immunoglobulin encoding sequences from known antibody sequence in another species (e.g., mouse).

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266L19867019870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for this use are known in the art. Fully human and chimeric antibodies of the present invention also include IgG2, IgG3, IgE, IgA, IgM, and IgD antibodies. Similar plasmids can be constructed for expression of other heavy chain isotypes, or for expression of antibodies comprising lambda light chains.

Thus, in another aspect of the invention, the structural features of known, non-human or human antibodies (e.g., a mouse anti-human PD-L1/PD-L2 antibody) can be used to create structurally related human anti-human PD-L1/PD-L2 antibodies that retain at least one functional property of the antibodies of the invention, such as binding to PD-L1 and PD-L2. Another functional property includes inhibiting binding of the original known, non-human or human antibodies in a competition ELISA assay. In addition, one or more CDR or variable regions of the present invention (e.g., including the sequences of Table 1, or portions thereof) can be combined recombinantly with known human framework regions and CDRs to create additional, recombinantly-engineered, human anti-PD-L1/PD-L2 antibodies of the present invention.

Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of variable regions of the present invention (e.g., including the sequences of Table 1, or portions thereof). The antibodies further can comprise the CDR2s of variable regions of the present invention (e.g., including the sequences of Table 1, or portions thereof). The antibodies further can comprise the CDR1s of variable regions of the present invention (e.g., including the sequences of Table 1, or portions thereof). In other embodiments, the antibodies can comprise any combinations of the CDRs.

The CDR1, 2, and/or 3 regions of the engineered antibodies described above can comprise the exact amino acid sequence(s) as those of variable regions of the present invention (e.g., including the sequences of Table 1, or portions thereof) disclosed herein. However, the ordinarily skilled artisan will appreciate that some deviation from the exact CDR sequences may be possible while still retaining the ability of the antibody to bind PD-L1 and/or PD-L2 effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention (e.g., including the sequences of Table 1, or portions thereof).

The structural features of non-human or human antibodies described herein can be used to create structurally related human antibodies that retain at least one functional property of the antibodies of the present invention, such as binding to both human PD-L1 and PD-L2. Another functional property includes inhibiting binding of the original known, non-human or human PD-L1 and/or PD-L2 antibodies in a competition ELISA assay. Table 1 presents numerous vK and vH sequences containing numerous CDRs that can be mixed and matched in any combination so long as the recombinant antibody or antigen-binding fragment thereof maintains the ability to bind PD-L1 and PD-L2.

In some embodiments, monoclonal antibodies capable of binding human PD-L1 and PD-L2 are provided, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 1.

Similarly, monoclonal antibodies capable of binding human PD-L1 and PD-L2, comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 1, are also provided.

Monoclonal antibodies capable of binding human PD-L1 and PD-L2, comprising a heavy chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of heavy chain variable domain CDRs presented in Table 1; and comprising a light chain wherein the variable domain comprises at least a CDR having a sequence that is at least 80%, 85%, 90%, 91%, 92%, 93%, 94%, 95%, 96%, 97%, 98%, 99%, 99.5% or 100% identical from the group of light chain variable domain CDRs presented in Table 1, are also provided.

A skilled artisan will note that such percentage homology is equivalent to and can be achieved by introducing 1, 2, 3, 4, 5, 6, 7, 8, 9, 10, or more conservative amino acid substitutions within a given CDR.

The monoclonal antibodies of the present invention can comprise a heavy chain, wherein the variable domain comprises at least a CDR having a sequence selected from the group consisting of the heavy chain variable domain CDRs presented in Table 1 and a light chain, wherein the variable domain comprises at least a CDR having a sequence selected from the group consisting of the light chain variable domain CDRs presented in Table 1.

Such monoclonal antibodies can comprise a light chain, wherein the variable domain comprises at least a CDR having a sequence selected from the group consisting of CDR-L1, CDR-L2, and CDR-L3, as described herein; and/or a heavy chain, wherein the variable domain comprises at least a CDR having a sequence selected from the group consisting of CDR-H1, CDR-H2, and CDR-H3, as described herein. In some embodiments, the monoclonal antibodies capable of binding human PD-L1 and PD-L2 comprises or consists of CDR-L1, CDR-L2, CDR-L3, CDR-H1, CDR-H2, and CDR-H3, as described herein.

The heavy chain variable domain of the monoclonal antibodies of the present invention can comprise or consist of the vH amino acid sequence set forth in Table 1 and/or the light chain variable domain of the monoclonal antibodies of the present invention can comprise or consist of the vκ amino acid sequence set forth in Table 1.

The present invention further provides fragments of said monoclonal antibodies which include, but are not limited to, Fv, Fab, F(ab')2, Fab', dsFv, scFv, sc(Fv)2 and diabodies; and multispecific antibodies formed from antibody fragments. For example, a number of immunoinhibitory molecules, such as CTLA-4, and the like, can be bound in a bispecific or multispecific manner Other fragments of the monoclonal antibodies of the present invention are also contemplated. For example, individual immunoglobulin heavy and/or light chains are provided, wherein the variable domains thereof comprise at least a CDR presented in Table 1. In one embodiment, the immunoglobulin heavy chain comprises at least a CDR having a sequence that is at least 80%, 85%, 90%, 91%, 92%, 93%, 94%, 95%, 96%, 97%, 98%, 99%, 99.5% or 100% identical from the group of heavy chain or light chain variable domain CDRs presented in Table 1. In another embodiment, an immunoglobulin light chain comprises at least a CDR having a sequence that is at least 80%, 85%, 90%, 91%, 92%, 93%, 94%, 95%, 96%, 97%, 98%, 99%, 99.5% or 100% identical from the group of light chain or heavy chain variable domain CDRs described herein (e.g., presented in Table 1), are also provided.

In some embodiments, the immunoglobulin heavy and/or light chain comprises a variable domain comprising at least one of CDR-L1, CDR-L2, CDR-L3, CDR-H1, CDR-H2, or CDR-H3 described herein. Such immunoglobulin heavy chains can comprise or consist of at least one of CDR-H1, CDR-H2, and CDR-H3. Such immunoglobulin light chains can comprise or consist of at least one of CDR-L1, CDR-L2, and CDR-L3.

In other embodiments, an immunoglobulin heavy and/or light chain according to the present invention comprises or consists of a vH or vκ variable domain sequence, respectively, provided in Table 1.

The present invention further provides polypeptides which have a sequence selected from the group consisting of vH variable domain, vκ variable domain, CDR-L1, CDR-L2, CDR-L3, CDR-H1, CDR-H2, and CDR-H3 sequences described herein.

Antibodies, immunoglobulins, and polypeptides of the invention can be use in an isolated (e.g., purified) form or contained in a vector, such as a membrane or lipid vesicle (e.g. a liposome).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce binding activity and can be corrected by replacing the amino acids with amino acid residues of the original antibody derived from a non-human animal.

Modifications and changes may be made in the structure of the antibodies of the present invention, and in the DNA sequences encoding them, and still obtain a functional molecule that encodes an antibody and polypeptide with desirable characteristics. For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said polypeptides, without appreciable loss of their biological activity.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (<RTI 3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody to, for example, increase stability. By "altering" is meant deleting one or more carbohydrate moieties found in the antibody, and/or adding one or more glycosylation sites that are not present in the antibody. Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Similarly, removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr et al. (1987) and by Edge et al. (1981). Enzymatic cleavage of carbohydrate moieties on antibodies can be achieved by the use of a variety of endo- and exo-glycosidases as described by Thotakura et al. (1987).

Other modifications can involve the formation of immunoconjugates. For example, in one type of covalent modification, antibodies or proteins are covalently linked to one of a variety of non proteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

Conjugation of antibodies or other proteins of the present invention with heterologous agents can be made using a variety of bifunctional protein coupling agents including but not limited to N-succinimidyl (2-pyridyldithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, carbon labeled 1-isothiocyanatobenzyl methyldiethylene triaminepentaacetic acid (MX-DTPA) is an exemplary chelating agent for conjugation of radionucleotide to the antibody (WO 94/11026).

In another aspect, the present invention features antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated antibodies can be used diagnostically or prognostically to monitor polypeptide levels in tissue as part of a clinical testing procedure, e.g., to determine the efficacy of a given treatment regimen. Detection can be facilitated by coupling (i e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); an example of a luminescent material includes luminol; examples of bioluminescent materials include luciferase, luciferin, and aequorin, and examples of suitable radioactive material include $^{125}$I, $^{131}$I, $^{35}$S, or $^{3}$H. [0134] As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, Pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

In some embodiments, conjugations can be made using a "cleavable linker" facilitating release of the cytotoxic agent or growth inhibitory agent in a cell. For example, an acid-labile linker, peptidase-sensitive linker, photolabile linker, dimethyl linker or disulfide-containing linker (See e.g. U.S. Pat. No. 5,208,020) may be used. Alternatively, a fusion protein comprising the antibody and cytotoxic agent or growth inhibitory agent may be made, by recombinant techniques or peptide synthesis. The length of DNA may comprise respective regions encoding the two portions of the conjugate either adjacent one another or separated by a region encoding a linker peptide which does not destroy the desired properties of the conjugate.

In addition to simply binding PD-L1 and PD-L2, antibodies, such as those described herein, may be selected for their effects on PD-L1 and PD-L2 functions, such as modulating FoxP3 expression, modulating phosphorylation of ERK1 or ERK2, modulating phosphorylation of PKC-θ, modulating phosphorylation of SHP-2, modulating cytokine production, and modulating cellular proliferation and/or metastasis, is determined.

In some embodiments, the test compound has an effect selected from the group consisting of (a) upregulates PD-L2/RGMb signaling and thereby downregulates ERK 1 or ERK 2 phosphorylation; (b) downregulates PD-L2/RGMb signaling and thereby upregulates ERK 1 or ERK 2 phosphorylation; (c) upregulates PD-L2/RGMb signaling and thereby downregulates PKC-θ phosphorylation; (d) downregulates PD-L2/RGMb signaling and thereby upregulates PKC-θ phosphorylation; (e) upregulates PD-L2/RGMb signaling and thereby upregulates SHSP-2 phosphorylation; and (f) downregulates PD-L2/RGMb signaling and thereby downregulates SHP-2 phosphorylation.

FoxP3, ERK1/ERK2, PKC-θ, and SHP-2 are well known in the art. For example, FOXP3 has a role in regulating the development of B cells, T cells and CD25+/CD4+ regulatory T cells. It is expressed in adult T-cell leukaemia/lymphoma and is widely used as a marker of a population of regulatory T cells (Tregs) that control immunotolerance and enable tumour cells to evade the host response (Bignone and Banham (2008) EOBT 8:1897-1920). SHP-2 (also known as Syp, SHPTP2, PTP2C, PTPN11, PTP1D and BPTP3) is a member of the family of non-membrane tyrosine phosphatases (U.S. Pat. Nos. 5,589,375, and 5,831,009). The SHP-2 protein contains two src homology 2 (SH2) domains, conserved regions of approximately 100 amino acids originally identified in Src protein tyrosine kinases, that promote protein-protein interactions through phosphotyrosyl residue binding (Neel, Semin Cell. Bioi. 4: 419-432 (1993)). These two domains have been shown to display differential functions in the regulation of the SHP-2 phosphatase and consequently affect different signaling pathways. The N-terminal SH2 domain serves as a regulatory and recruiting domain, producing an autoinhibitory effect through intramolecular interactions with the internal catalytic phosphatase domain. While the C-terminal SH2 domain acts merely to recruit other proteins for intermolecular interactions necessary for signal transduction (Pei et al., Proc. Natl. Acad. Sci. US.A. 93: 1141-1145 20 (1996)). The phosphorylation state of the SHP-2 molecule regulates its phosphatase activity. Protein-tyrosine phosphatases, including SH2-containing phosphatases, are highly conserved among eukaryotes from such diverse species as mammals, including humans, to yeast and Xenopus. SHP-2 has been shown to play a critical role in aberrant immunological responses (e.g., in the allergic response. (Pazdrak et al., J. Exp. 30 Med. 186: 561-568 (1997)). SHP-2 phosphorylation is easily detectable by methods known in the art, including, without limitation, the detection of altered mobility of the SHP-2 molecule on a PAGE gel, phosphorylation assays, and assays which measure the activity of the SHP-2 molecule. Detection of SHP-2 phosphorylation may be direct, or alternatively may be indirect, e.g., detection of a downstream activity or event.

ERK1 and ERK2 (also known as MAPK1 and MAPK2) are themselves kinases (Boulton, et al., Cell 65: 663-675, (1991)). Activation of the ERK molecule is via serine/threonine phosphorylation or tyrosine phosphorylation. Inhibition of ERK 1 and 2 activation may result from inhibition of upstream phosphorylation of the ERK 1 and 2 molecules, or may result from the activation of a phosphatase which dephosphorylates ERK1 and 2, to reduce activity. The ERK proteins are known to be activated by phosphorylation by the MEK molecule, a dual-specificity kinase. Upon activation, ERK1 and ERK2 translocate to the nucleus where they can directly phosphorylate and activate a variety of transcription 20 factors including c-Myc, C/EBP~, p62, TCF/Elk-1, ATF-2 and c-Jun. The phosphorylation state/activation state of the ERK1 and 2 molecules upon T cell activation is an indication of signaling via PD-1. The phosphorylation state/state of activation of ERK 1 and 2 can readily be determined by the skilled practitioner using assays readily available in the art. For instance, the phosphorylation state of the ERK1 25 and 2 molecules can be determined using an antibody specific for the phosphorylated form of the p42/44 ERK.1/2 proteins (phospho-Thr202/Tyr204 specific), several of which are commercially available. Alternatively, the phosphorylation state of the ERK.1 and 2 molecules can be determined by their mobility on a gel, using an antibody which recognizes ERK1 and 2, regardless of the phosphorylation state) for identification. Alternatively, the activation state of ERK.1 and 2 can be determined by assaying kinase activity of the ERK.1 and 2 molecules. Determination of the ERK1 and 2 phosphorylation/activation state may also by indirect methods, e.g., detection of a downstream activity or event.

The PKC isoenzymes play an important role in many cell signaling events. PKC-θ (also known as PKC-θ, PKCT, PRKCT, nPKC-θ and PRKCQ) is a calcium-independent isoform of the PKC family of serine-threonine kinases. Transient overexpression of the PKC-θ protein in murine thymoma cells resulted in transcriptional activation of an interleukin-2 promoter-driven construct (Baier et al., Eur. 15 J Biochem. 225: 195-203(1994)), indicating a role for PKC-θ in T-cell signaling pathways. PKC-θ has also been shown to be activated in the course of T cell receptor mediated T cell activation, and this activation correlates with translocation of the PKC-θ molecule to the plasma membrane at the site of APC contact (U.S. Pat. No. 6,040,152). PKC-θ has also been implicated in other cellular processes including apoptosis (Datta et al., J Biol. Chern. 272: 20317-20320 (1997)), cytoskeletal arrangement (Pietromonaco et al., J Biol. Chern. 273: 7594-7603 (1998); Simons et al., Biochem. Biop~ys. Res. Commun. 253: 561-565 (1998)), proliferation (Passalacqua et al., Biochem. J 337: 113-118 (1999)), and angiogenesis and wound repair (Tang et al., J Bioi. Chern. 272: 28704-25 28711 (1997)). The phosphorylation state reflects the activation state of the PKC-θ molecule with phosphorylation indicating activation. The phosphorylation state/state of activation or PKC-θ can readily be determined by the skilled practitioner using assays readily available in the art. For instance, the phosphorylation state of the PKC-θ molecule can be determined using an antibody specific for the phosphorylated form of the PKC-θ protein (e.g., anti-phospho T538), which is commercially available. Alternatively, the phosphorylation state of the PKC-θ molecule can be determined by its mobility on a gel, using an antibody which recognizes PKC-θ (regardless of the phosphorylation state) for detection. Alternatively, the activation state of PKC-θ can be determined by assaying kinase activity of the PKC-θ molecule (Kupfer et al., U.S. Pat. No. 6,040,152), or by assaying for translocation to the membrane at the point of APC contact (Kupfer et al., U.S. Pat. No. 6,040,152). Determination of the PKC-θ phosphorylation/activation state may also be by indirect methods, e.g., detection of a downstream activity or event.

IV. Recombinant Expression Vectors and Host Cells

Another aspect of the invention pertains to vectors, preferably expression vectors, containing a nucleic acid molecule encoding a polypeptide of the present invention (e.g., including the sequences of Table 1, or portions thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors of the invention can be designed for expression of polypeptides of the present invention (e.g., including the sequences of Table 1, or portions thereof) in prokaryotic or eukaryotic cells. For example, the polypeptides can be expressed in bacterial cells such as E. coli, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of polypeptides in prokaryotes is most often carried out in E. coli with vectors containing constitutive or inducible promoters directing the expression of either fusion or non-fusion proteins. Fusion vectors add a number of amino acids to a polypeptide encoded therein, usually to the amino terminus of the recombinant polypeptide. Such fusion vectors typically serve three purposes: 1) to increase expression of recombinant polypeptide; 2) to increase the solubility of the recombinant polypeptide; and 3) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant polypeptide.

Examples of suitable inducible non-fusion E. coli expression vectors include pTrc (Amann et al. (1988) Gene 69:301-315) and pET 1 Id (Studier et al. (1990) Methods Enzymol. 185:60-89). Target gene expression from the pTrc vector relies on host RNA polymerase transcription from a hybrid trp-lac fusion promoter. Target gene expression from the pET 11 d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant polypeptide expression in E. coli is to express the polypeptide in host bacteria with impaired capacity to proteolytically cleave the recombinant polypeptide (Gottesman, S. (1990) Methods Enzymol. 185:119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast S. cerevisiae include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and picZ (Invitrogen Corp, San Diego, Calif.).

Alternatively, polypeptides of the present invention (e.g., including the sequences of Table 1, or portions thereof) can be expressed in insect cells using baculovirus expression vectors. Baculovirus vectors available for expression of polypeptides in cultured insect cells (e.g., Sf 9 cells) include the pAc 'series (Smith et al. (1983) Mol. Cell Biol. 3:2156-2165) and the pVL series (Lucklow and Summers (1989) Virology 170:31-39).

In yet another embodiment, a nucleic acid of the present invention (e.g., including the sequences of Table 1, or portions thereof) is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) Science 249:374-379) and the .alpha.-fetoprotein promoter (Campes and Tilghman (1989) Genes Dev. 3:537-546).

Another aspect of the invention pertains to host cells into which a nucleic acid molecule of the present invention (e.g., Table 1) is introduced within a recombinant expression vector or a nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the present invention (e.g., including the sequences of Table 1, or portions thereof) can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a PD-L1 and/or PD-L2 polypeptide or anti-PD-L1 and/or PD-L2 antibody polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a polypeptide of the present invention (e.g., including the sequences of Table 1, or portions thereof). Accordingly, the invention further provides methods for producing a polypeptide of the present invention (e.g., including the sequences of Table 1, or portions thereof) using the host cells of the present invention. In one embodiment, the method comprises culturing the host cell of the invention (into which a recombinant expression vector encoding a polypeptide of the present invention (e.g., including the sequences of Table 1, or portions thereof) has been introduced) in a suitable medium such that a polypeptide of the present invention (e.g., including the sequences of Table 1, or portions thereof) is produced. In another embodiment, the method further comprises isolating a polypeptide of the present invention (e.g., including the sequences of Table 1, or portions thereof) from the medium or the host cell.

The host cells of the invention can also be used to produce non-human transgenic animals, as described below.

V. Antibody Conjugates/Immunotoxins

In another aspect, the present invention features anti-PD-L1/PD-L2 antibodies conjugated to a therapeutic moiety, such as a cytotoxin, a drug (e.g., an immunosuppressant) or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated anti-PD-L1/PD-L2 antibodies can be used diagnostically or prognostically to monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $_{125}I$, $_{131}I$, $_{35}S$ and $_3H$.

The antibody conjugates of the invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

VI. Uses and Methods of the Invention

The compositions described herein (including dual binding antibodies, as well as derivatives and conjugates thereof) can be used in a variety of diagnostic and prognostic applications. For example, many human maladies could benefit from modulated immune response (e.g., either upregulation or downregulation of immune responses) and this can be achieved in an efficient manner by simultaneously modulating a network of co-immunoinhibitory signaling pathways mediated via PD-L1 and PD-L2 using a single agent. Thus, methods for modulating the binding and/or signaling of co-immunoinhibitory pathways mediated via PD-L1 and PD-L2 (e.g., modulating one or more of the interactions selected from the group consisting of (a) PD-L1 binding to PD-1; (b) PD-L1 binding to B7-1; (c) PD-L2 binding to PD-1; (d) PD-L2 binding to RGMb; (e) a co-immunoinhibitory signal mediated by PD-L1 binding to PD-1; (f) a co-immunoinhibitory signal mediated by PD-L1 binding to B7-1; (g) a co-immunoinhibitory signal mediated by PD-L2 binding to PD-1; and (h) a co-immunoinhibitory signal mediated by PD-L2 binding to RGMb) using the compositions of the present invention are contemplated. In addition, methods for modulating the biological activity of PD-L1 and PD-L2 using the compositions of the invention are contemplated. In particular, compositions of the present invention (e.g., anti-PD-L1/PD-L2 antibodies) described herein are useful for diagnostic and prognostic applications related to particular conditions mediated by PD-L1 and PD-L2.

In some embodiments, the antibodies are associated with a component or device for the use of the antibodies in an ELISA or RIA. Non-limiting examples include antibodies immobilized on solid surfaces for use in these assays (e.g., linked and/or conjugated to a detectable label based on light or radiation emission as described above). In other embodiments, the antibodies are associated with a device or strip for detection of PD-L1 and/or PD-L2 by use of an immunochromatographic or immunochemical assay such as in a "sandwich" or competitive assay. Additional examples of such devices or strips are those designed for home testing or rapid point of care testing. Further examples include those that are designed for the simultaneous analysis of multiple analytes in a single sample. For example, an unlabeled antibody of the invention may be applied to a "capture" PD-L1 and/or PD-L2 polypeptides in a biological sample and the captured (or immobilized) PD-L1 and/or PD-L2 polypeptides may be bound to a labeled form of an antibody of the present invention for detection. Other standard embodiments of immunoassays are well known the skilled artisan, including assays based on, for example, immunodiffusion, immunoelectrophoresis, immunohistopathology, immunohistochemistry, and histopathology.

1. Screening Methods

One aspect of the present invention relates to screening assays, including non-cell based assays. In one embodiment, the assays provide a method for identifying antibodies which modulate the interaction between PD-L1/PD-L1 receptors and/or PD-L2/PD-L2 receptors (PD-L1 and PD-L2 (e.g., (a) PD-L1 binding to PD-1; (b) PD-L1 binding to B7-1; (c) PD-L2 binding to PD-1; (d) PD-L2 binding to RGMb). In another embodiments, the assays provide a method for identifying antibodies which modulate the biological activity of PD-L1 and/or PD-L2.

In one embodiment, the invention relates to assays for screening candidate or test antibodies which bind to, or modulate the biological activity of PD-L1 and/or PD-L2, e.g., modulate the ability of the polypeptide to interact with (e.g., bind to) its cognate binding partner. In one embodiment, a method for identifying an antibody to modulate an immune response entails determining the ability of the antibody to modulate, e g enhance or inhibit, the interaction between between PD-L1/PD-L1 receptors and/or PD-L2/PD-L2 receptors (PD-L1 and PD-L2 (e.g., (a) PD-L1 binding to PD-1; (b) PD-L1 binding to B7-1; (c) PD-L2 binding to PD-1; (d) PD-L2 binding to RGMb).

In one embodiment, an assay is a cell-free assay, comprising contacting PD-L1 or PD-L2, with a test antibody and determining the ability of the test antibody to modulate (e.g. stimulate or inhibit) the interaction between between PD-L1/PD-L1 receptors and/or PD-L2/PD-L2 receptors (PD-L1 and PD-L2 (e.g., (a) PD-L1 binding to PD-1; (b) PD-L1 binding to B7-1; (c) PD-L2 binding to PD-1; (d) PD-L2 binding to RGMb). Determining modulation of the interaction between between PD-L1/PD-L1 receptors and/or PD-L2/PD-L2 receptors (PD-L1 and PD-L2 (e.g., (a) PD-L1 binding to PD-1; (b) PD-L1 binding to B7-1; (c) PD-L2 binding to PD-1; (d) PD-L2 binding to RGMb) can be accomplished, e.g., by measuring direct binding or by measuring indirect parameters as described below.

For example, in a direct binding assay, PD-L1 or PD-L2 protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemission or by scintillation counting. Alternatively, the targets can be enzymatically labeled with, for example, horseradish peroxidase, alkaline phosphatase, or luciferase, and the enzymatic label detected by determination of conversion of an appropriate substrate to product.

Determining the interaction between PD-L1/PD-L1 receptors and/or PD-L2/PD-L2 receptors (PD-L1 and PD-L2 (e.g., (a) PD-L1 binding to PD-1; (b) PD-L1 binding to B7-1; (c) PD-L2 binding to PD-1; (d) PD-L2 binding to RGMb) can also be accomplished using a technology such as real-time Biomolecular Interaction Analysis (BIA) (Sjolander, S. and Urbaniczky, C. (1991) *Anal. Chem.* 63:2338-2345 and Szabo et al. (1995) *Curr. Opin. Struct. Biol.*

5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. Polypeptides or molecules can be immobilized on a BIAcore chip and antibodies can be tested for binding to the immobilized polypeptides or molecules. An example of using the BIA technology is described by Fitz et al. (1997) *Oncogene* 15:613.

In one or more embodiments of the above described assay methods, it may be desirable to immobilize polypeptides or molecules to facilitate separation of complexed from uncomplexed forms of one or both of the proteins or molecules, as well as to accommodate automation of the assay. Binding of a test antibody to a target (e.g., PD-L1 or PD-L2) can be accomplished in any vessel suitable for containing the reactants. Non-limiting examples of such vessels include microtiter plates, test tubes, and microcentrifuge tubes Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene. In one embodiment, a fusion protein can be provided which adds a domain that allows one or both of the proteins to be bound to a matrix. For example, glutathione-S-transferase/PD-L1 or PD-L2 fusion proteins, or glutathione-S-transferase/target fusion proteins, can be adsorbed onto glutathione sepharose beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of PD-L1 and/or PD-L2 binding or activity can be determined using standard techniques.

In an alternative embodiment, determining the ability of an antibody of the invention to modulate the interaction between PD-L1/PD-L1 receptors and PD-L2/PD-L2 receptors (e.g., PD-L1 and PD-L2 (e.g., (a) PD-L1 binding to PD-1; (b) PD-L1 binding to B7-1; (c) PD-L2 binding to PD-1; (d) PD-L2 binding to RGMb) can be accomplished by determining the ability of the test antibody to modulate the activity of a polypeptide or product that functions downstream of PD-L1 and/or PD-L2, e.g., co-immunoinhibitory-related signaling.

In an alternative embodiment, determining the ability of an antibody of the invention to modulate the interaction between PD-L1/PD-L1 receptors and PD-L2/PD-L2 receptors (e.g., PD-L1 and PD-L2 (e.g., (a) PD-L1 binding to PD-1; (b) PD-L1 binding to B7-1; (c) PD-L2 binding to PD-1; (d) PD-L2 binding to RGMb) can be accomplished by determining the ability of the test antibody to modulate the binding of a PD-1-, B7-1-, or RGMb-Ig fusion protein to a PD-L1- or PD-L2-transfected cell.

This invention further pertains to novel antibodies identified by the above-described screening assays. Accordingly, it is within the scope of this invention to further use an antibody identified as described herein in an appropriate animal model. For example, an antibody identified as described herein can be used in an animal model to determine the efficacy, toxicity, or side effects of treatment with such an antibody. Alternatively, an antibody identified as described herein can be used in an animal model to determine the mechanism of action of such an antibody. Furthermore, this invention pertains to uses of novel antibodies identified by the above-described screening assays for treatments as described herein.

2. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the expression and/or activity level of PD-L1 and/or PD-L2 or fragments thereof, in the context of a biological sample (e.g., blood, serum, cells, or tissue) to thereby determine whether an individual is afflicted with a disease or disorder, or is at risk of developing a disorder, associated with aberrant or unwanted biomarker expression or activity. The invention also provides for prognostic (or predictive) assays for determining whether an individual is at risk of developing a disorder associated with biomarker polypeptide, nucleic acid expression or activity. For example, mutations in a biomarker gene can be assayed in a biological sample.

Such assays can be used for prognostic or predictive purpose to thereby prophylactically treat an individual prior to the onset or after recurrence of a disorder characterized by or associated with biomarker polypeptide, nucleic acid expression or activity.

Another aspect of the invention pertains to monitoring the influence of agents (e.g., drugs, compounds, and small nucleic acid-based molecules) on the expression or activity of PD-L1 and/or PD-L2, or fragments thereof, in clinical trials. These and other agents are described in further detail in the following sections.

3. Diagnostic Assays

The present invention provides, in part, methods, systems, and code for accurately classifying whether a biological sample is associated with a disease or disorder associated with aberrant expression or activity of by PD-L1 and/or PD-L2. In some embodiments, the present invention is useful for classifying a sample (e.g., from a subject) as associated with or at risk for a disease or disorder mediated by PD-L1 and/or PD-L2 (known as a PD-L1 sample and/or PD-L2 sample) using a statistical algorithm and/or empirical data (e.g., the presence or level of an PD-L1 and/or PD-L2).

An exemplary method for detecting the level of expression or activity of PD-L1 and/or PD-L2 or fragments thereof, and thus useful for classifying whether a sample is associated with a disease or disorder mediated by PD-L1 and/or PD-L2 or a clinical subtype thereof involves obtaining a biological sample from a test subject and contacting the biological sample with an antibody or antigen-binding fragment thereof of the present invention capable of detecting PD-L1 and/or PD-L2 such that the level of expression or activity of PD-L1 and/or PD-L2 is detected in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a PD-L1 sample and/or PD-L2 sample based upon a prediction or probability value and the presence or level of PD-L1 and/or PD-L2. The use of a single learning statistical classifier system typically classifies the sample as a PD-L1 sample and/or PD-L2 sample (e.g., chronic infection) sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the PD-L1 sample and/or PD-L2 sample classification results to a clinician, e.g., a gastroenterologist or a general practitioner.

In another embodiment, the method of the present invention further provides a diagnosis in the form of a probability that the individual has a condition or disorder associated with aberrant expression or activity of PD-L1 and/or PD-L2. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having the condition or disorder. In yet another embodiment, the method of the present invention further provides a prognosis of the condition or disorder in the individual. In some instances, the method of classifying a sample as an PD-L1 sample and/or PD-L2 sample is further based on the symptoms (e.g., clinical factors) of the individual from which the sample is obtained. The symptoms or group of symptoms can be, for example, diarrhea, abdominal pain, cramping, fever, anemia, weight loss, anxiety, depression, and combinations thereof. In some embodiments, the diagnosis of an individual as having a condition or disorder associated with aberrant expression or activity of PD-L1 and/or PD-L2 is followed by administering to the individual a therapeutically effective amount of a drug useful for treating one or more symptoms associated with the condition or disorder (e.g., chemotherapeutic agents).

In one embodiment, the methods further involve obtaining a control biological sample (e.g., biological sample from a subject who does not have a condition or disorder mediated by PD-L1 and/or PD-L2), a biological sample from the subject during remission or before developing a condition or disorder mediated by PD-L1 and/or PD-L2, or a biological sample from the subject during treatment for developing a condition or disorder mediated by PD-L1 and/or PD-L2.

4. Prognostic Assays

The diagnostic methods described herein can furthermore be utilized to identify subjects having or at risk of developing a disease or disorder associated with aberrant expression or activity of PD-L1 and/or PD-L2 or a fragment thereof. As used herein, the term "aberrant" includes biomarker expression or activity levels which deviates from the normal expression or activity in a control.

The assays described herein, such as the preceding diagnostic assays or the following assays, can be utilized to identify a subject having or at risk of developing a disorder associated with a misregulation of PD-L1 and/or PD-L2 activity or expression, such as in cancer. Alternatively, the prognostic assays can be utilized to identify a subject having or at risk for developing a disorder associated with a misregulation of PD-L1 and/or PD-L2 activity or expression, such as in cancer. Thus, the present invention provides a method for identifying and/or classifying a disease associated with aberrant expression or activity of PD-L1 and/or PD-L2 or a fragment thereof. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant biomarker expression or activity. Thus, the present invention provides methods for determining whether a subject can be effectively treated with an agent for a disease associated with aberrant PD-L1 and/or PD-L2 expression or activity in which a test sample is obtained and PD-L1 and/or PD-L2 expression or activity is detected (e.g., wherein a significant increase or decrease in biomarker polypeptide or nucleic acid expression or activity relative to a control is diagnostic for a subject that can be administered the agent to treat a disorder associated with aberrant PD-L1 and/or PD-L2 expression or activity). In some embodiments, significant increase or decrease in biomarker expression or activity comprises at least 2 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher or lower, respectively, than the expression activity or level of the marker in a control sample.

5. Monitoring of Effects During Clinical Trials

Monitoring the influence of agents (e.g., drugs) on the expression or activity of PD-L1 and/or PD-L2 or a fragment thereof (e.g., the modulation of cancer) can be applied not only in basic drug screening, but also in clinical trials. For example, the effectiveness of an agent can be determined by detecting a modulation (i.e., increase or decrease) in expression and/or activity of PD-L1 and/or PD-L2 using an antibody of the present invention, relative to a control reference. In such clinical trials, the expression and/or activity of PD-L1 and/or PD-L2 can be used as a "read out" or marker of the phenotype of a particular cell or condition.

In some embodiments, the present invention provides a method for monitoring the effectiveness of treatment of a subject with an agent (e.g., an agonist, antagonist, peptidomimetic, polypeptide, peptide, nucleic acid, small molecule, or other drug) including the steps of (i) obtaining a pre-administration sample from a subject prior to administration of the agent; (ii) detecting the level of expression and/or activity of PD-L1 and/or PD-L2 or fragments thereof in the preadministration sample; (iii) obtaining one or more post-administration samples from the subject; (iv) detecting the level of expression or activity of PD-L1 and/or PD-L2 or fragments thereof in the post-administration samples; (v) comparing the level of expression or activity of PD-L1 and/or PD-L2 or fragments thereof in the pre-administration sample with that of the biomarker in the post administration sample or samples; and (vi) altering the administration of the agent to the subject accordingly. For example, increased administration of the agent may be desirable to decrease the expression or activity of PD-L1 and/or PD-L2 to lower levels than detected. According to such an embodiment, PD-L1 and/or PD-L2 expression or activity may be used as an indicator of the effectiveness of an agent, even in the absence of an observable phenotypic response.

6. Treatment Methods

The compositions described herein (including dual binding antibodies and derivatives and conjugates thereof) can be used in a variety of in vitro and in vivo therapeutic applications (e.g., by upregulating or downregulating the immune response). In one embodiment, antibodies that block the interaction between between PD-L1/PD-L1 receptors and PD-L2/PD-L2 receptors (e.g., PD-L1 and PD-L2 (e.g., (a) PD-L1 binding to PD-1; (b) PD-L1 binding to B7-1; (c) PD-L2 binding to PD-1; (d) PD-L2 binding to RGMb) can prevent inhibitory signaling. In one embodiment, antibodies that block costimulatory signal of the PD-1 ligand block a costimulatory signal to an immune cell. Furthermore, ligation of PD-L2 can induce cytokine secretion and survival of dendritic cells. Thus, antibodies that block PD-L2 ligation can inhibit dendritic cell survival and reduce cytokine expression by dendritic cells, and through these mechanisms inhibit an immune response. In particular, antibodies described herein are useful for therapeutic applications related to particular conditions mediated by PD-L1 and PD-L2, as discussed, for example, in Keir et al. (2008) Annu. Rev. Immunol. 26:677; Sharpe et al., (2007) Nat. Immunol. 8:239; Freeman et al. (2007) J. Exp. Med. 10:2223.

In one embodiment, the antibodies and the antigen-binding fragments of the present invention are useful for therapeutic applications, in addition to diagnostic, prognostic, and prevention applications, regarding neurodegenerative diseases including, but not limited to, geriopsychosis, Alzheimer disease, Down syndrome, Parkinson's disease, Creutzfeldt-Jakob disease, diabetic neuropathy, Parkinson syndrome, Huntington's disease, Machado-Joseph disease, amyotrophic lateral sclerosis, and diabetic neuropathy.

In another embodiment, the antibodies and the antigen-binding fragments of the present invention are useful for therapeutic applications, in addition to diagnostic, prognostic, and prevention applications (such as treating, and delaying the onset or progression of the diseases), to inhibit diseases that upregulate the immune reaction, for example, asthma, autoimmune diseases (glomerular nephritis, arthritis, dilated cardiomyopathy-like disease, ulceous colitis, Sjogren syndrome, Crohn disease, systemic erythematoses, chronic rheumatoid arthritis, multiple sclerosis, psoriasis, allergic contact dermatitis, polymyosiis, pachyderma, periarteritis nodosa, rheumatic fever, vitiligo vulgaris, insulin dependent diabetes mellitus, Behcet disease, Hashimoto disease, Addison disease, dermatomyositis, myasthenia gravis, Reiter syndrome, Graves' disease, anaemia perniciosa, Goodpasture syndrome, sterility disease, chronic active hepatitis, pemphigus, autoimmune thrombopenic purpura, and autoimmune hemolytic anemia, active chronic hepatitis, Addison's disease, anti-phospholipid syndrome, atopic allergy, autoimmune atrophic gastritis, achlorhydra autoimmune, celiac disease, Cushing's syndrome, dermatomyositis, discoid lupus, erythematosis, Goodpasture's syndrome, Hashimoto's thyroiditis, idiopathic adrenal atrophy, idiopathic thrombocytopenia, insulin-dependent diabetes, Lambert-Eaton syndrome, lupoid hepatitis, some cases of lymphopenia, mixed connective tissue disease, pemphigoid, pemphigus vulgaris, pernicious anema, phacogenic uveitis, polyarteritis nodosa, polyglandular autosyndromes, primary biliary cirrhosis, primary sclerosing cholangitis, Raynaud's syndrome, relapsing polychondritis, Schmidt's syndrome, limited scleroderma (or crest syndrome), sympathetic ophthalmia, systemic lupus erythematosis, Takayasu's arteritis, temporal arteritis, thyrotoxicosis, type b insulin resistance, ulcerative colitis and Wegener's granulomatosis).

In still another embodiment, the antibodies and the antigen-binding fragments of the present invention are useful for therapeutic applications, in addition to diagnostic, prognostic, and prevention applications (such as treating and delaying the onset or progression of the diseases) for persistent infectious disease (e.g., viral infectious diseases including HPV, HBV, hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, and influenza virus. Other antigens associated with pathogens that can be used as described herein are antigens of various parasites, includes malaria, preferably malaria peptide based on repeats of NANP. In addition, bacterial, fungal and other pathogenic diseases are included, such as *Aspergillus, Brugia, Candida, Chlamydia, Coccidia, Cryptococcus, Dirofilaria, Gonococcus, Histoplasma, Leishmania, Mycobacterium, Mycoplasma, Paramecium, Pertussis, Plasmodium, Pneumococcus, Pneumocystis, Rickettsia, Salmonella, Shigella, Staphylococcus, Streptococcus, Toxoplasma* and *Vibriocholerae*. Exemplary species include *Neisseria gonorrhea, Mycobacterium tuberculosis, Candida albicans, Candida tropicalis, Trichomonas vaginalis, Haemophilus vaginalis,* Group B *Streptococcus* sp., *Microplasma hominis, Hemophilus ducreyi, Granuloma inguinale, Lymphopathia venereum, Treponema pallidum, Brucella abortus. Brucella melitensis, Brucella suis, Brucella canis, Campylobacter fetus, Campylobacter fetus* intestinalis, *Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani, Clostridium botulinum*; or, a fungus, such as, e.g., *Paracoccidioides brasiliensis*; or other pathogen, e.g., *Plasmodium falciparum*. Also included are National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens*; *Staphylococcus enterotoxin* B, *Salmonella species*, *Shigella dysenteriae*, *Escherichia coli* strain O157:H7, *Vibrio cholerae*, *Cryptosporidium parvum*; Category C agents, such as nipah virus, hantaviruses, tickborne hemorrhagic fever viruses, tickborne encephalitis viruses, yellow fever, and multidrug-resistant tuberculosis; helminths, such as *Schistosoma* and *Taenia*; and protozoa, such as *Leishmania* (e.g., *L. mexicana*) and *Plasmodium*.

In still another embodiment, the antibodies or the antigen-binding fragments of the present invention are useful for therapeutic applications, in addition to diagnostic, prognostic, and prevention applications regarding organ graft rejection, graft-versus-host disease (GVHD), allergic disease, and diseases caused by attenuation of immune reactions mediated by PD-L1 and PD-L2.

In some embodiments, downregulation of immune responses is desired. For example, the immune response can be downmodulated using anti-PD-L1/PD-L2 antibodies that block costimulation by a PD-1 ligand such as PD-L1, or which promote the binding of PD-L1 and/or PD-L2 with PD-1, (e.g., while not affecting or while inhibiting costimulation by PD-1 ligand).

In one embodiment of the invention, tolerance is induced against specific antigens by co-administering an antigen with an antibody which blocks B7-mediated and/or PD-1 ligand-mediated costimulation. For example, tolerance can be induced to specific proteins. In one embodiment, immune responses to allergens, or to foreign proteins to which an immune response is undesirable, can be inhibited. For example, patients that receive Factor VIII frequently generate antibodies against this clotting factor. Co-administration of an antibody that blocks a B7-mediated and/or PD-1 ligand-mediated costimulatory signal or an antibody that stimulates a CTLA4-, PD-1- and/or RGMb-mediated inhibitory signal in combination with recombinant factor VIII (or by physically linked to Factor VIII, e.g., by cross-linking) can result in immune response downregulation.

In another embodiment, treatment methods may further use agents that block an activity of costimulatory pathways, such as that of other B lymphocyte antigen like B7-1, B7-2, or B7-3) to further downmodulate immune responses. Two separate agents that downmodulate immune responses can be combined as a single composition or administered separately (simultaneously or sequentially) to more effectively downregulate immune cell mediated immune responses in a subject. Furthermore, a therapeutically active amount of one or more of the subject antibodies, can be used in conjunction with other downmodulating reagents to influence immune responses. Examples of other immunomodulating reagents include, without limitation, antibodies that block a costimulatory signal, (e.g., against CD28 or ICOS), antibodies that act as agonists of CTLA4, and/or antibodies against other immune cell markers (e.g., against CD40, against CD40 ligand, or against cytokines), fusion proteins (e.g., CTLA4-Fc), and immunosuppressive drugs (e.g., rapamycin, cyclosporine A or FK506). In some embodiments, an PD-L1/PD-L2 dual-blocking antibody of the present invention can be combined with radiation therapy and/or a histone deacetylase inhibitor (e.g., vorinostat, romidepsin, panobinostat, valproic acid, belinostat, mocetinostat, abexinostat, entinostat, SB-939, resminostat, givinostat, quisinostat, and the like) to enhance therapeutic efficacy.

Downregulating or preventing a PD-1 ligand costimulation, or promoting an interaction between a PD-1 ligand and PD-1 is useful to downmodulate the immune response, e.g., in situations of tissue, skin and organ transplantation, in graft-versus-host disease (GVHD), or in inflammatory diseases such as systemic lupus erythematosus, and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of an antibody which inhibits PD-1 ligand costimulation alone or in conjunction with another downmodulatory agent, prior to or at the time of transplantation can promote the generation of an inhibitory signal. Moreover, inhibition of PD-1 ligand costimulatory signals, or promotion of a PD-1 ligand or PD-1 inhibitory signals, may also be sufficient to anergize the immune cells, thereby inducing tolerance in a subject. Induction of long-term tolerance by blocking a PD-1 ligand mediated costimulatory signal may avoid the necessity of repeated administration of these blocking reagents.

To achieve sufficient immunosuppression or tolerance in a subject, it may also be desirable to block the costimulatory function of other polypeptides. For example, it may be desirable to block the function of B7-1, B7-2, or B7-1 and B7-2 by administering a soluble form of a combination of peptides having an activity of each of these antigens, blocking antibodies against these antigens or blocking small molecules (separately or together in a single composition) prior to or at the time of transplantation. Alternatively, it may be desirable to promote inhibitory activity of a PD-1 ligand or PD-1 and inhibit a costimulatory activity of B7-1 and/or B7-2. Other downmodulatory agents that can be used in connection with the downmodulatory methods of the invention include, for example, agents that transmit an inhibitory signal via CTLA4, soluble forms of CTLA4, antibodies that activate an inhibitory signal via CTLA4, blocking antibodies against other immune cell markers or soluble forms of other receptor ligand pairs (e.g., agents that disrupt the interaction between CD40 and CD40 ligand (e.g., anti CD40 ligand antibodies)), antibodies against cytokines, or immunosuppressive drugs.

Downregulating immune responses is useful for treating a number of conditions, e.g., in situations of tissue, skin and organ transplantation, in graft-versus-host disease (GVHD), or in autoimmune diseases such as systemic lupus erythematosus, multiple sclerosis, allergy, a transplant, hypersensitivity response, a disorder requiring increased CD4+ T cell production or function, a disorder requiring improved vaccination efficiency, a disorder requiring increased regulatory T cell production or function, and a disorder requiring improved vaccination efficiency. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of an agent described herein prior to or at the time of transplantation can promote the generation of an inhibitory signal. Moreover, inhibition may also be sufficient to anergize the immune cells, thereby inducing tolerance in a subject. Induction of long-term tolerance avoids the necessity of repeated administration of these blocking reagents.

Downmodulation of immune responses are also useful in treating autoimmune disease. Many autoimmune disorders are the result of inappropriate activation of immune cells that are reactive against self tissue and which promote the production of cytokines and autoantibodies involved in the pathology of the diseases. Preventing the activation of autoreactive immune cells may reduce or eliminate disease symptoms. Administration of agents described herein are useful for preventing the generating of autoantibodies or cytokines which may be involved in the disease process. Additionally, agents that promote an inhibitory function mediated by the interaction between RGMb and PD-L2 may induce antigen-specific tolerance of autoreactive immune cells, which could lead to long-term relief from the disease. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see, e.g., Paul ed., Fundamental Immunology, Raven Press, New York, Third Edition 1993, chapter 30).

Inhibition of immune cell activation is also useful therapeutically in the treatment of allergy and allergic reactions, e.g., by inhibiting IgE production. Allergic reactions can be systemic or local in nature, depending on the route of entry of the allergen and the pattern of deposition of IgE on mast cells or basophils. Thus, inhibition of immune cell mediated allergic responses locally or systemically by administration of an agent described herein that promotes an inhibitory function mediated by RGMb and PD-L2.

Inhibition of immune cell activation may also be important therapeutically in parasitic and viral infections of immune cells. For example, in the acquired immune deficiency syndrome (AIDS), viral replication is stimulated by immune cell activation. Modulation of these interactions may result in inhibition of viral replication and thereby ameliorate the course of AIDS. Modulation of these interactions may also be useful in promoting the maintenance of pregnancy. Females at risk for spontaneous abortion (e.g., those who have previously had a spontaneous abortion or those who have had difficulty conceiving) because of immunologic rejection of the embryo or fetus can be treated with agents that modulate these interactions.

Downregulation of an immune response by modulating the interaction between RGMb and PD-L2 may also be useful in treating an autoimmune attack of autologous tissues. It is therefore within the scope of the invention to modulate conditions exacerbated by autoimmune attack, such as autoimmune disorders, as well as conditions such as heart disease, myocardial infarction, and atherosclerosis.

Also useful therapeutically is the simultaneous blockage of the interaction of PD-L1 and PD-L2 with co-immunoinhibitory receptors as a means of upregulating an immune response. Upregulation of immune responses can be in the form of enhancing an existing immune response or eliciting an initial immune response. For instance, enhancing an immune response using the subject compositions and methods is useful in cases of infections with microbes (e.g., bacteria, viruses, or parasites). In one embodiment, an antibody that blocks the interaction of PD-L1 and PD-L2 with co-immunoinhibitory receptors is used to enhance the immune response. Such an antibody (e.g., a blocking (non-activating) antibody that blocks PD-L1 and PD-L2 binding to PD-1 with or without blocking PD-L2 binding to RGMb) is therapeutically useful in situations where upregulation of antibody and cell-mediated responses would be beneficial (e.g., in treating cancer, an infectious disease (e.g., bacteria, viruses, or parasites), a parasitic infection, asthma associated with impaired airway tolerance, a neurological disease, and an immunosuppressive disease). Exemplary disorders include viral skin diseases, such as Herpes or shingles, in which case such an agent can be delivered topically to the skin. In addition, systemic viral diseases such as influenza, the common cold, and encephalitis might be alleviated by systemic administration of such agents.

Alternatively, immune responses can be enhanced in an infected patient through an ex vivo approach, for instance, by removing immune cells from the patient, contacting immune cells in vitro with an agent that modulate the interaction between RGMb and PD-L2 and reintroducing the in vitro stimulated immune cells into the patient.

In certain instances, it may be desirable to further administer other agents that upregulate immune responses, for example, forms of other B7 family members that transduce signals via costimulatory receptors, in order to further augment the immune response.

Agents that upregulate an immune response can be used prophylactically in vaccines against various polypeptides (e.g., polypeptides derived from pathogens). Immunity against a pathogen (e.g., a virus) can be induced by vaccinating with a viral protein along with an agent that upregulates an immune response, in an appropriate adjuvant.

In another embodiment, upregulation or enhancement of an immune response function, as described herein, is useful in the induction of tumor immunity. In another embodiment, the immune response can be stimulated by the methods described herein, such that preexisting tolerance, clonal deletion, and/or exhaustion (e.g., T cell exhaustion) is overcome. For example, immune responses against antigens to which a subject cannot mount a significant immune response, e.g., to an autologous antigen, such as a tumor specific antigens can be induced by administering appropriate agents described herein that upregulate the imimune response. In one embodiment, an autologous antigen, such as a tumor-specific antigen, can be coadministered. In another embodiment, an immune response can be stimulated against an antigen (e.g., an autologous antigen) to treat a neurological disorder. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

In still another embodiment, agents described herein useful for upregulating immune responses can further be linked, or operatively attached, to toxins using techniques that are known in the art, e.g., crosslinking or via recombinant DNA techniques. Such agents can result in cellular destruction of desired cells. In one embodiment, a toxin can be conjugated to an antibody, such as a bispecific antibody. Such antibodies are useful for targeting a specific cell population, e.g., using a marker found only on a certain type of cell, e.g., RGMb- and/or PD-L2-expressing cell. The preparation of immunotoxins is, in general, well known in the art (see, e.g., U.S. Pat. No. 4,340,535, and EP 44167). Numerous types of disulfide-bond containing linkers are known which can successfully be employed to conjugate the toxin moiety with a polypeptide. In one embodiment, linkers that contain a disulfide bond that is sterically "hindered" are preferred, due to their greater stability in vivo, thus preventing release of the toxin moiety prior to binding at the site of action. A wide variety of toxins are known that may be conjugated to polypeptides or antibodies of the invention. Examples include: numerous useful plant-, fungus- or even bacteria-derived toxins, which, by way of example, include various A chain toxins, particularly ricin A chain, ribosome inactivating proteins such as saporin or gelonin, α-sarcin, aspergillin, restrictocin, ribonucleases, such as placental ribonuclease, angiogenic, diphtheria toxin, and *Pseudomonas* exotoxin, etc. A preferred toxin moiety for use in connection with the invention is toxin A chain which has been treated to modify or remove carbohydrate residues, deglycosylated A chain. (U.S. Pat. No. 5,776,427). Infusion of one or a combination of such cytotoxic agents, (e.g., ricin fusions) into a patient may result in the death of immune cells.

7. Kits

The present invention also encompasses kits for detecting PD-L1 and/or PD-L2 polypeptides. For example, the kit can comprise at least one anti-PD-L1/PD-L2 antibody of the present invention and/or control reagents (e.g., PD-L1 and/or PD-L2 protein standards) in a suitable container.

A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or PD-L1 and/or PD-L2 protein standards). A kit may additionally include buffers and other reagents recognized for use in a method of the disclosed invention. Non-limiting examples include agents to reduce non-specific binding, such as a carrier protein or a detergent.

VII. Administration of Agents

The immune modulating agents of the invention are administered to subjects in a biologically compatible form suitable for pharmaceutical administration in vivo, to either enhance or suppress immune cell mediated immune responses. By "biologically compatible form suitable for administration in vivo" is meant a form of the protein to be administered in which any toxic effects are outweighed by the therapeutic effects of the protein. The term "subject" is intended to include living organisms in which an immune response can be elicited, e.g., mammals Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of an agent may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The agents or the invention described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin. Sterile injectable solutions can be prepared by incorporating an agent of the invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent of the invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

This invention is further illustrated by the following examples which should not be construed as limiting. The contents of all references, patents and published patent applications cited throughout this application, as well as the Figures, are incorporated herein by reference. Other embodiments of the present invention are described in the following Examples. The present invention is further illustrated by the following examples which should not be construed as further limiting.

EXAMPLES

Example 1

Discovery and Characterization of Antibodies Blocking PD-L1 and PD-L2 Interactions with PD-1

Human PD-L1 or PD-L2 extracellular domain, each fused to mouse IgG2a constant region (PD-L1-mIgG2a and PD-L2-mIgG2a, respectively) were used as immunogens. Female BALB/c or C57BL/6 PD-L1/PD-L2 dual knockout mice (Bu et al. (2011) *Arterioscler. Thromb. Vasc. Biol.* 31(5):1100-7) were immunized using traditional and rapid immunization in multiple sites (RIMMS) protocols.

Traditional Immunization

The traditional immunization protocol utilized BALB/c dual knock-out mice and immunization with PD-L2-mIgG2a in complete Freund's adjuvant (CFA) on day 1, followed by PD-L2-mIgG2a in incomplete Freund's adjuvant (IFA) on days 15 and 29, followed by immunization with PD-L1-mIgG2a in IFA on days 43 and 57. Titer was assessed on day 67 and the animals were boosted with oligo-histidine tagged PD-L1 and PD-L2 extracellular domain proteins on day 74. Splenocytes were collected and fusions performed on day 78.

Hybridomas were formed using PEG-mediated fusion with SP 2/0 mouse myeloma cells as the fusion partner. Hybridomas were plated in multiwell plates at clonal density onto MRC-5 human diploid lung fibroblast feeder layers and grown in HAT media (hypoxanthine/aminopterin/thymidine, ATCC 69x), then gradually weaned to HT media (ATCC 71x). Hybridomas were screened for binding to PD-L1, PD-L2 and an irrelevant antigen using a FACS-based staining assay.

Sequences for the isolated monoclonal antibodies, such as the 1B9 and 4H1 monoclonal antibodies, are provided in Table 1. Briefly, the variable domain of the light and heavy chains of the mAbs were sequenced and the complementarity determining regions (CDR) domains thereof are provided. Numbering is shown according to nucleic acid positions and the corresponding amino acid residues, corresponding to CDRs for example, can easily be identified based on the provided translations.

Following subcloning, hybridomas 1B9 and 4H1 from the traditional immunization strategy (now designated 1B9.2E11.3 and 4H1.G10.15, respectively) were further characterized in an additional FACS-based staining assay. Hybridoma supernatants were mixed with 300.19 cells expressing either human PD-L1 or PD-L2 or untransfected 300.19 cells and incubated with agitation at 4° C. for 30 minutes. The cells were collected by centrifugation, rinsed with PBS with 2% fetal bovine serum (FBS), then incubated with a phycoerythrin (PE) labeled goat-anti-mouse IgG antibody with agitation at 4° C. for 30 minutes. Cells were again collected by centrifugation, washed, then preserved in PBS with 2% formaldehyde prior to FACS analysis. Controls were an isotype control antibody (MOPC31C) and no antibody ("Blank"). Results (mean fluorescence intensity, or MFI) are summarized in Table 2; note that in this assay, MFI is proportional to antibody binding.

TABLE 2

| Antibody | PD-L1 expressing 300.19 cells | PD-L2 expressing 300.19 cells | Untransfected 300.19 cells |
|---|---|---|---|
| Isotype control | 45 | 19 | 21 |
| Blank | 21 | 37 | |
| 1B9.2E11.3 | 26957 | 1289 | 79 |
| 4H1.G10.15 | 27893 | 93 | 20 |

Similar binding assays as described for the experimental results shown in Table 2 were conducted using a variety of monoclonal antibody titers and with additional negative controls. The results are shown in Table 3 and these results confirm the results shown in Table 2.

TABLE 3

| Well Name | mAb/Cell Used | Sample | Specificity | mAb concentration undiluted or 10 ug/ml | 1 to 10 or 1 ug/ml | 1 to 100 or 0.1 ug/ml | |
|---|---|---|---|---|---|---|---|
| Human PD-L1-expressing 300 Cells | | | | | | | |
| A8 | 1B9.2E11.7 | Supernatant | Dual | 242571 | 235986 | 236865 | Mean |
| A11 | 4H1.F9.19 | Supernatant | Dual | 241489 | 238240 | 223289 | of PE |
| E6 | WASH | N/A | Neg. Ctrl. | 396 | 183 | 171 | Signal |
| F7 | MOPC31C | Antibody | Neg. Ctrl. | 263 | 183 | 250 | |
| E8 | 29E.2A3 | Antibody | PD-L1 Alone | 234726 | 234336 | 109412 | |
| E9 | 3.2 | Antibody | PD-L2 Alone | 819 | 1333 | 588 | |

| Well Name | mAb Used | Sample | Specificity | mAb concentration undiluted or 10 ug/ml | 1 to 10 or 1 ug/ml | 1 to 100 or 0.1 ug/ml | |
|---|---|---|---|---|---|---|---|
| Human PD-L2-expressing 300 Cells | | | | | | | |
| A8 | 1B9.2E11.7 | Supernatant | Dual | 9786 | 2719 | 1253 | Mean |
| A11 | 4H1.F9.19 | Supernatant | Dual | 840 | 757 | 672 | of PE |
| E6 | WASH | N/A | Neg. Ctrl. | 586 | 370 | 209 | Signal |
| E7 | MOPC31C | Antibody | Neg. Ctrl. | 173 | 164 | 149 | |
| B8 | 29E.2A3 | Antibody | PD-L1 Alone | 251 | 150 | 150 | |
| E9 | 3.2 | Antibody | PD-L2 Alone | 218582 | 205735 | 80064 | |
| Negative Control 300.19 Cells | | | | | | | |
| A8 | 1B9.2E11.7 | Supernatant | Dual | 1019 | 706 | 669 | Mean |
| A11 | 4H1.F9.19 | Supernatant | Dual | 827 | 630 | 624 | of PE |
| E6 | WASH | N/A | Neg. Ctrl. | 254 | 229 | 320 | Signal |
| E7 | MOPC31C | Antibody | Neg. Ctrl. | 208 | 210 | 194 | |
| E8 | 29E.2A3 | Antibody | PD-L1 Alone | 206 | 214 | 183 | |
| E9 | 3.2 | Antibody | PD-L2 Alone | 410 | 213 | 252 | |

1B9.2E11.3 and 4H1.G10.15 were also characterized using an assay which measures blockade of PD-L1/PD-1 or PD-L2/PD-1 binding was assessed using a FACS-based assay. Antibodies were mixed with 300.19 cells expressing either human PD-L1 or PD-L2 and incubated with agitation at 4° C. for 30 minutes. The cells then incubated with agitation at 4° C. for 30 minutes with human PD-1 ectodomain/human IgG1 fusion protein. Cells were collected by centrifugation, rinsed with PBS with 2% fetal bovine serum (FBS). PD-1/PD-L1 or PD-1/PD-L2 binding was detected by incubation with a PE labeled goat-anti-human IgG antibody (absorbed to remove reactivity with mouse Ig) with agitation at 4° C. for 30 minutes. Cells were again collected by centrifugation, washed, then preserved in PBS with 2% formaldehyde prior to FACS analysis. Controls were an isotype control antibody (MOPC31C) and PD-1(−) control (no PD-1 ectodomain/human IgG1 fusion protein). Results (MFI) are summarized in Table 4; note that in this assay, MFI is inversely proportional to blockage of PD-1/PD-L binding.

TABLE 4

| Antibody | PD-L1 expressing 300.19 cells | PD-L2 expressing 300.19 cells |
|---|---|---|
| Isotype control | 26671 | 19203 |
| PD-1(−) control | 47 | 19 |
| 1B9.2E11.3 | 51 | 20248 |
| 4H1.G10.15 | 44 | 21100 |

Similar competition binding assays as described for the experimental results shown in Table 4 were conducted using a variety of monoclonal antibody titers and with additional negative controls. The results are shown in Table 5 and these results confirm the results shown in Table 4.

TABLE 5

| Well Name | mAb Used | mAb Specificity | 90 ug/ml | 30 ug/ml | 10 ug/ml | 3.3 ug/ml | 1.1 ug/ml | 0.37 ug/ml | 0.12 ug/ml | 0.04 ug/ml | |
|---|---|---|---|---|---|---|---|---|---|---|---|
| | | | | | | mAb concentration | | | | | |
| | | | Human PD-L1-expressing 300 Cells | | | | | | | | |
| A1 | 1B9 | Dual | 62 | 52 | 57 | 46 | 66 | 50 | 188 | 5801 | Mean |
| A2 | 4H1 | Dual | 49 | 80 | 48 | 57 | 92 | 55 | 61 | 4623 | of PE |
| A3 | 29E.2A3 | PD-L1 Alone | 54 | 53 | 52 | 50 | 51 | 65 | 523 | 6105 | Signal |
| A4 | 9E5. | PD-L2 Alone | 9390 | 13126 | 14549 | 12800 | 14701 | 14318 | 13382 | 12101 | |
| A5 | MOPC31C | Neg. Ctrl. | 11767 | 14889 | 12572 | 11943 | 13578 | 13454 | 15209 | 13302 | |
| A6 | CELLS ALONE | Neg. Ctrl. | 49 | | | | | | | | |
| | | | Human PD-L2-expressing 300 Cells | | | | | | | | |
| A8 | 1B9 | Dual | 43979 | 52595 | 58371 | 54304 | 58865 | 55826 | 52061 | 58006 | Mean |
| A9 | 4H1 | Dual | 52174 | 56129 | 56772 | 55980 | 54643 | 52394 | 52477 | 54704 | of PE |
| A10 | 29E.2A3 | PD-L1 Alone | 55075 | 53919 | 53834 | 56665 | 56121 | 52881 | 53928 | 58825 | Signal |
| A11 | 9E5. | PD-L2 Alone | 6105 | 24250 | 42020 | 46722 | 51993 | 51071 | 53939 | 57482 | |
| A12 | MOPC31C | Neg. Ctrl. | 53544 | 54188 | 52462 | 52618 | 58440 | 60567 | 59108 | 60825 | |
| A7 | CELLS ALONE | Neg. Ctrl. | 37 | | | | | | | | |

In addition, the capacity of dual- and PD-L1-only binding monoclonal antibodies to block the binding of human B7-1 to human PD-L1 was assayed according to the FACS analyses described for the experimental results shown in Tables 4 and 5. Briefly, 300-hPD-L1 cells were pre-incubated with the mAbs for 30 minutes. Human B7-1-human igG fusion protein (R&D systems) was added at 1 ug·mL and incubated for 30 minutes with a single post-wash. Mouse Ig absorbed Fab2 goat anti-human IgG-PE (Southern Biotech 2043-09) was added at 2.5 ug/mL for 30 minutes and then washed twice. The results shown in Table 6 demonstrate that antibodies 1B9 and 4H1 block B7-1 binding to PD-L1.

TABLE 6

| Well Name | mAb Specificity mAb Concentration (ug/ml) | PD-L1 Alone 29E.2A3 | PD-L1 Alone 339.4C10 | PD-L1 Alone 298.3D12 | Dual 368A.1.1B9 | Dual 368A.1.4H1 | Neg. Ctrl. C1.18 mIgG2a control | Neg. Ctrl. MOPC31C mIgG1 control | |
|---|---|---|---|---|---|---|---|---|---|
| A1 | 20 | 811 | 1768 | 1399 | 917 | 895 | 4541 | 3590 | Mean |
| A2 | 10 | 797 | 1702 | 879 | 936 | 914 | 3912 | 3547 | of PE |
| A3 | 5 | 853 | 1620 | 791 | 933 | 903 | 3857 | 3579 | Signal |
| A4 | 2.5 | 823 | 1715 | 864 | 933 | 873 | 3879 | 3879 | |
| A5 | 1.25 | 788 | 1793 | 865 | 910 | 926 | 3724 | 3493 | |
| A6 | 0.625 | 850 | 1760 | 842 | 804 | 938 | 3843 | 3707 | |
| A7 | 0.313 | 770 | 1754 | 869 | 944 | 862 | 3758 | 3962 | |
| A8 | 0.156 | 853 | 2267 | 863 | 944 | 928 | 4032 | 3722 | |
| A9 | 0.078 | 807 | 3087 | 983 | 1035 | 1141 | 3937 | 4317 | |
| A10 | 0.039 | 1227 | 3502 | 1326 | 1469 | 1707 | 4281 | 3986 | |
| A11 | 0.0195 | 1707 | 3467 | 1633 | 2124 | 2231 | 3505 | 4763 | |
| A12 | 0.0098 | 2540 | 4196 | 2240 | 2804 | 3037 | 4058 | 4406 | |

RIMMS Immunization

B16 mice were immunized according to a RIMMS protocol. Mice were immunized with human PD-L1-mIgG2a and/or PD-L2-mIgG2a in adjuvant by subcutaneous/intraperitoneal (SC/IP) or footpad injection as described in Table 7. Titer was assessed on day 18 and splenocytes were collected for fusions on day 21.

TABLE 7

| Day | PD-L1 | PD-L2 | Adjuvant | Injection type |
|---|---|---|---|---|
| 1 | — | 100 µg | CFA | SC/IP |
| 1 | — | 5 µg | Alum | Footpad |
| 4 | 25 µg | 100 µg | PBS | SC/IP |
| 4 | 5 µg | 5 µg | Alum | Footpad |
| 6 | 25 µg | 50 µg | IFA | SC/IP |
| 6 | 5 µg | 5 µg | Alum | Footpad |
| 8 | 50 µg | 50 µg | PBS | SC/IP |
| 8 | 5 µg | 5 µg | Alum | Footpad |
| 11 | 50 µg | 50 µg | IFA | SC/IP |
| 11 | 5 µg | 5 µg | Alum | Footpad |
| 13 | 50 µg | 25 µg | PBS | SC/IP |
| 13 | 5 µg | 5 µg | Alum | Footpad |
| 15 | 100 µg | 25 µg | IFA | SC/IP |
| 15 | 5 µg | 5 µg | Alum | Footpad |
| 18 | 100 µg | — | PBS | SC/IP |
| 18 | 5 µg | — | Alum | Footpad |

Fusions were performed as described for the traditional immunization strategy, and hybridoma supernatents were screened for binding to human PD-L1 and PD-L2.

The screening assay tested binding of hybridoma supernatants to a mixture of untransfected 300.19 murine pre-B cells, 300.19 cells expressing human PD-L1 and 300.19 cells expressing human PD-L2 (in a ratio of approximately 20%, 40%, 40%, respectively). Antibodies (hybridoma supernatents or control antibodies) were incubated with the cell mixtures with agitation at 4° C. for 30 minutes, then the cells were collected by centrifugation, rinsed with PBS with 2% fetal bovine serum (FBS), and incubated with a phycoerythrin (PE) labeled goat-anti-mouse Ig antibody with agitation at 4° C. for 30 minutes. Cells were again collected by centrifugation, washed, then preserved in PBS with 2% formaldehyde prior to FACS analysis. Controls were (a) an antibody specific for human PD-L1, (b) an antibody specific for human PD-L2, (c) a mixture of the anti-PD-L1 and PD-L2 antibodies, and an isotype control (MOPC31C).

FACS data was analyzed by drawing a gate ("cells") around viable cells—"cells, total mean fluorescence" shows their staining intensity. A gate ("P1") was set to analyze the MFI of cells above the isotype control MFI. % P1 shows the percent of cells in P1 which indicates the percentage of positively staining cells; P1 median fluorescence shows the MFI of cells in the P1 gate. Hybridomas with % P1 above 70% and P1 fluorescence signal above 5000 were considered to be of interest for subcloning and further characterization. FACS data for 29 of the hybridomas from the RIMMS protocol are shown in Table 8.

TABLE 8

| Well Name | Cells, Total Mean Fluorescence | P1 Median Fluorescence | % P1 |
|---|---|---|---|
| 1A8 | 116863 | 105657 | 91.3 |
| 1E4. | 102070 | 102939 | 91.6 |
| 8G2 | 35225 | 38667 | 85.8 |
| 1D11 | 42647 | 19719 | 90.2 |
| 3A2 | 38540 | 17065 | 85 |
| 3B11 | 6379 | 7605 | 73.7 |

TABLE 8-continued

| Well Name | Cells, Total Mean Fluorescence | P1 Median Fluorescence | % P1 |
|---|---|---|---|
| 3F4 | 10722 | 10532 | 86 |
| 3H6 | 85640 | 12883 | 89.4 |
| 4C1 | 88622 | 21998 | 90.7 |
| 4E1. | 12184 | 11595 | 86.7 |
| 5A6 | 9395 | 9587 | 81.3 |
| 9C12 | 9069 | 8981 | 86.1 |
| 1B4 | 6716 | 5889 | 83.1 |
| 1B11 | 7445 | 5974 | 84.4 |
| 1F6 | 94441 | 119771 | 81.1 |
| 1H8 | 5201 | 6268 | 70.9 |
| 1H12 | 6357 | 6072 | 85.6 |
| 2D5 | 96521 | 115477 | 84 |
| 2H11 | 51086 | 47720 | 84.4 |
| 3D12 | 5534 | 5690 | 84.2 |
| 4C8 | 88961 | 109423 | 78.2 |
| 4C9 | 51501 | 15177 | 87.4 |
| 5E10. | 11634 | 7170 | 80.4 |
| 5H4 | 5281 | 5642 | 80 |
| 5H5 | 5172 | 5537 | 80.6 |
| 8A1 | 7224 | 6657 | 79.2 |
| 9G9 | 11365 | 11400 | 73.6 |
| 10A7 | 30658 | 41786 | 54.9 |
| 10H6 | 17860 | 26851 | 46.4 |
| Anti-PD-L1 control | 99315 | 205842 | 48.2 |
| Anti-PD-L2 control | 82131 | 170077 | 48.2 |
| Anti-PD-L1/L2 control | 156820 | 179733 | 87.2 |
| Isotype control | 1620 | 151802 | 0.9 |

Example 2

Discovery and Characterization of Antibodies Blocking PD-L1 and PD-L2 Interactions with PD-1 Using In Vitro Antibody Library Technology PD-L1 and PD-L2 soluble extracellular domain proteins and cells transfected with PD-L1 or PD-L2 proteins are used to select in vitro antibody libraries to discover antibodies which bind to both PD-L1 and PD-L2 and block their interaction with PD-1. Soluble PD-L1 and PD-L2 target proteins used for library selection are whole ectodomain constructs or constructs comprising the IgV domain only.

Multiple libraries are used to discover antibodies blocking PD-L1 and PD-L2 interactions with PD-1, including Metha1, a $1.2 \times 10^{10}$ member library constructed of randomly paired heavy and light chain genes isolated from the peripheral blood of 57 non-immunized human volunteers, Metha2, a $1.5 \times 10^{10}$ member library constructed of randomly pair heavy and lambda light chains captured from the peripheral blood of 57 non-immunized human volunteers, and Griffin1, a $1.2 \times 10^{9}$ member semi-synthetic library based on the lox library (Herschorn et al. (2010) *J. Immunol.* 185(12):7623-32). Libraries are selected by panning with immobilized target protein or by incubation with tagged target protein and subsequent recovery using the tag (e.g., using streptavidin-coated magnetic beads to collect biotinylated target protein). Multiple rounds of selection, recovery and phage rescue are used to enrich for the desired antibodies.

Multiple selection strategies are used to discover the desired antibodies, including selection with one of the target proteins followed by screening the selected antibodies for binding to the other target protein and rounds of selection alternating the target proteins. Additionally, rounds of selection on whole cells expressing a target protein are incorporated in some strategies.

DNA encoding antibodies which bind specifically to both human PD-L1 and human PD-L2 is isolated from the selected phage and is used to construct whole IgG format antibodies. The antibodies are characterized for binding to the target proteins (human PD-L1 and human PD-L2) as well as the mouse and cynomolgus monkey homologues. Additionally, the antibodies are tested in an assay of PD-L1/PD-1 and PD-L2/PD-1 interaction blockade (see, for example, Example 1).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising one or more isolated nucleic acid molecules that encodes a monoclonal antibody that specifically binds both PD-L1 and PD-L2, or antigen-binding fragment thereof, wherein
   a) the antibody comprises i) three light chain CDRs: CDR-L1, CDR-L2, and CDR-L3, wherein CDR-L1 consists of the amino acid sequence encoded by nucleotides 70-102 of SEQ ID NO: 13, CDR-L2 consists of the amino acid sequence encoded by nucleotides 148-168 of SEQ ID NO: 13, and CDR-L3 consists of the amino acid sequence encoded by nucleotides 265-291 of SEQ ID NO: 13; and ii) three heavy chain CDRs: CDR-H1, CDR-H2, and CDR-H3, wherein CDR-H1 consists of the amino acid sequence encoded by nucleotides 91-108 of SEQ ID NO: 15, CDR-H2 consists of the amino acid sequence encoded by nucleotides 151-198 of SEQ ID NO: 15, and CDR-H3 consists of the amino acid sequence encoded by nucleotides 295-330 of SEQ ID NO: 15; or
   b) the antigen-binding fragment thereof comprises i) three light chain CDRs: CDR-L1, CDR-L2, and CDR-L3, wherein CDR-L1 consists of the amino acid sequence encoded by nucleotides 70-102 of SEQ ID NO: 13, CDR-L2 consists of the amino acid sequence encoded by nucleotides 148-168 of SEQ ID NO: 13, and CDR-L3 consists of the amino acid sequence encoded by nucleotides 265-291 of SEQ ID NO: 13; and ii) three heavy chain CDRs: CDR-H1, CDR-H2, and CDR-H3, wherein CDR-H1 consists of the amino acid sequence encoded by nucleotides 91-108 of SEQ ID NO: 15, CDR-H2 consists of the amino acid sequence encoded by nucleotides 151-198 of SEQ ID NO: 15, and CDR-H3 consists of the amino acid sequence encoded by nucleotides 295-330 of SEQ ID NO: 15.

2. A vector comprising the isolated nucleic acid of claim 1.

3. A host cell comprising the vector of claim 2 which expresses the monoclonal antibody or antigen-binding fragment thereof.

4. A non-human transgenic animal comprising the nucleic acid of claim 1.

5. A method of producing at least one monoclonal antibody that specifically binds both PD-L1 and PD-L2, or antigen-binding fragment thereof, comprising culturing a cell comprising the isolated nucleic acid of claim 1 that produces the at least one monoclonal antibody, or antigen-binding fragment thereof, from the cell culture.

6. The isolated nucleic acid of claim 1, wherein the monoclonal antibody or antigen-binding fragment thereof inhibits one or more of the interactions selected from the group consisting of (a) PD-L1 binding to PD-1; (b) PD-L1 binding to B7-1; (c) PD-L2 binding to PD-1; (d) PD-L2 binding to RGMb; (e) a co-immunoinhibitory signal mediated by PD-L1 binding to PD-1; (f) a co-immunoinhibitory signal mediated by PD-L1 binding to B7-1; (g) a co-immunoinhibitory signal mediated by PD-L2 binding to PD-1; and (h) a co-immunoinhibitory signal mediated by PD-L2 binding to RGMb.

7. The isolated nucleic acid of claim 6, wherein the monoclonal antibody or antigen-binding fragment thereof inhibits one or more co-immunoinhibitory signals of (e), (f), (g), or (h).

8. The isolated nucleic acid of claim 1, wherein the monoclonal antibody or antigen-binding fragment thereof is chimeric.

9. The isolated nucleic acid of claim 1, wherein the monoclonal antibody or antigen-binding fragment thereof is a F(ab')2 fragment, Fab fragment, scFv, bi-specific scFv, tri-specific scFv, or diabody.

10. The isolated nucleic acid of claim 1, wherein the monoclonal antibody or antigen-binding fragment thereof comprises an immunoglobulin heavy chain constant domain selected from the group consisting of IgG, IgG1, IgG2, IgG2A, IgG2B, IgG3, IgG4, IgA, IgM, IgD, and IgE constant domains.

11. A composition comprising one or more isolated nucleic acid molecules that encodes a monoclonal antibody that specifically binds both PD-L1 and PD-L2, or antigen-binding fragment thereof, wherein
   a) the antibody comprises i) three light chain CDRs: CDR-L1, CDR-L2, and CDR-L3, wherein CDR-L1 consists of the amino acid sequence encoded by nucleotides 70-102 of SEQ ID NO: 17, CDR-L2 consists of the amino acid sequence encoded by nucleotides 148-168 of SEQ ID NO: 17, CDR-L3 consists of the amino acid sequence encoded by nucleotides 265-291 of SEQ ID NO: 17; and ii) three heavy chain CDRs: CDR-H1, CDR-H2, and CDR-H3, wherein CDR-H1 consists of the amino acid sequence encoded by nucleotides 91-108 of SEQ ID NO: 19, CDR-H2 consists of the amino acid sequence encoded by nucleotides 151-198 of SEQ ID NO: 19, and CDR-H3 consists of the amino acid sequence encoded by nucleotides 295-330 of SEQ ID NO: 19; or
   b) the antigen-binding fragment thereof comprises i) three light chain CDRs: CDR-L1, CDR-L2, and CDR-L3, wherein CDR-L1 consists of the amino acid sequence encoded by nucleotides 70-102 of SEQ ID NO: 17, CDR-L2 consists of the amino acid sequence encoded by nucleotides 148-168 of SEQ ID NO: 17, CDR-L3 consists of the amino acid sequence encoded by nucleotides 265-291 of SEQ ID NO: 17; and ii) three heavy chain CDRs: CDR-H1, CDR-H2, and CDR-H3, wherein CDR-H1 consists of the amino acid sequence encoded by nucleotides 91-108 of SEQ ID NO: 19, CDR-H2 consists of the amino acid sequence encoded by nucleotides 151-198 of SEQ ID NO: 19, and CDR-H3 consists of the amino acid sequence encoded by nucleotides 295-330 of SEQ ID NO: 19.

12. A vector comprising the isolated nucleic acid of claim 11.

13. A host cell comprising the vector of claim 12 which expresses the monoclonal antibody or antigen-binding fragment thereof.

14. A non-human transgenic animal comprising the nucleic acid of claim 11.

15. A method of producing at least one monoclonal antibody that specifically binds both PD-L1 and PD-L2, or antigen-binding fragment thereof, comprising culturing a cell comprising the isolated nucleic acid of claim 11 that produces the at least one monoclonal antibody, or antigen-binding fragment thereof, from the cell culture.

16. The isolated nucleic acid of claim 11, wherein the monoclonal antibody or antigen-binding fragment thereof inhibits one or more of the interactions selected from the group consisting of (a) PD-L1 binding to PD-1; (b) PD-L1 binding to B7-1; (c) PD-L2 binding to PD-1; (d) PD-L2 binding to RGMb; (e) a co-immunoinhibitory signal mediated by PD-L1 binding to PD-1; (f) a co-immunoinhibitory signal mediated by PD-L1 binding to B7-1; (g) a co-immunoinhibitory signal mediated by PD-L2 binding to PD-1; and (h) a co-immunoinhibitory signal mediated by PD-L2 binding to RGMb.

17. The isolated nucleic acid of claim 16, wherein the monoclonal antibody or antigen-binding fragment thereof inhibits one or more co-immunoinhibitory signals of (e), (f), (g), or (h).

18. The isolated nucleic acid of claim 11, wherein the monoclonal antibody or antigen-binding fragment thereof is chimeric.

19. The isolated nucleic acid of claim 11, wherein the monoclonal antibody or antigen-binding fragment thereof is a F(ab')2 fragment, Fab fragment, scFv, bi-specific scFv, tri-specific scFv, or diabody.

20. The isolated nucleic acid of claim 11, wherein the monoclonal antibody or antigen-binding fragment thereof comprises an immunoglobulin heavy chain constant domain selected from the group consisting of IgG, IgG1, IgG2, IgG2A, IgG2B, IgG3, IgG4, IgA, IgM, IgD, and IgE constant domains.

\* \* \* \* \*

SEQUENCE LISTING

```
<160> NUMBER OF SEQ ID NOS: 22

<210> SEQ ID NO 1
<211> LENGTH: 921
<212> TYPE: DNA
<213> ORGANISM: Homo sapiens

<400> SEQUENCE: 1
cactctggtg gggctgctcc aggcatgcag atcccacagg cgccctggcc agtcgtctgg      60
gcggtgctac aactgggctg gcggccagga tggttcttag actccccaga caggccctgg     120
aaccccccca ccttctcccc agccctgctc gtggtgaccg aaggggacaa cgccaccttc     180
acctgcagct tctccaacac atcggagagc ttcgtgctaa actggtaccg catgagcccc     240
agcaaccaga cggacaagct ggccgccttc ccgaggacc gcagccagcc cggccaggac      300
tgccgcttcc gtgtcacaca actgcccaac gggcgtgact tccacatgag cgtggtcagg     360
gcccggcgca atgacagcgg cacctacctc tgtggggcca tctccctggc ccccaaggcg     420
cagatcaaag agagcctgcg ggcagagctc agggtgacag agagaagggc agaagtgccc     480
acagcccacc ccagccctc acccaggtca gccggccagt tccaaaccct ggtggttggt     540
gtcgtgggcg gcctgctggg cagcctggtg ctgctagtct gggtcctggc cgtcatctgc     600
tcccgggccg cacgagggac aataggagcc aggcgcaccg gccagcccct gaaggaggac     660
ccctcagccg tgcctgtgtt ctctgtggac tatggggagc tggatttcca gtggcgagag     720 aagacccegg agcccccgt gccctgtgtc cctgagcaga cggagtatgc caccattgtc     780
tttcctagcg gaatgggcac ctcatccccc gcccgcaggg gctcagctga cggccctcgg     840
agtgcccagc cactgaggcc tgaggatgga cactgctctt ggccctctg accggcttcc     900 ttggccacca gtgttctgca g                                              921

<210> SEQ ID NO 2
<211> LENGTH: 288
<212> TYPE: PRT
<213> ORGANISM: Homo sapiens

<400> SEQUENCE: 2

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45
```

```
Asn Ala Thr Phe Thr Cys Ser Phe Ser Asn Thr Ser Glu Ser Phe Val
             50                  55                  60
Leu Asn Trp Tyr Arg Met Ser Pro Ser Asn Gln Thr Asp Lys Leu Ala
 65                  70                  75                  80
Ala Phe Pro Glu Asp Arg Ser Gln Pro Gly Gln Asp Cys Arg Phe Arg
                 85                  90                  95
Val Thr Gln Leu Pro Asn Gly Arg Asp Phe His Met Ser Val Val Arg
            100                 105                 110
Ala Arg Arg Asn Asp Ser Gly Thr Tyr Leu Cys Gly Ala Ile Ser Leu
            115                 120                 125
Ala Pro Lys Ala Gln Ile Lys Glu Ser Leu Arg Ala Glu Leu Arg Val
        130                 135                 140
Thr Glu Arg Arg Ala Glu Val Pro Thr Ala His Pro Ser Pro Ser Pro
145                 150                 155                 160
Arg Ser Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
            195                 200                 205
Leu Lys Glu Asp Pro Ser Ala Val Pro Val Phe Ser Val Asp Tyr Gly
210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
            275                 280                 285

<210> SEQ ID NO 3
<211> LENGTH: 968
<212> TYPE: DNA
<213> ORGANISM: Homo sapiens

<400> SEQUENCE: 3
gcttcccgag gctccgcacc agccgcgctt ctgtccgcct gcagggcatt ccagaaagat      60
gaggatattt gctgtcttta tattcatgac ctactggcat ttgctgaacg catttactgt     120
cacggttccc aaggacctat atgtggtaga gtatggtagc aatatgacaa ttgaatgcaa     180
attcccagta gaaaacaat  agacctggc  tgcactaatt gtctattggg aaatggagga     240
taagaacatt attcaatttg tgcatggaga ggaagacctg aaggttcagc atagtagcta     300
cagacagagg gcccggctgt tgaaggacca gctctcctg  ggaaatgctg cacttcagat     360
cacagatgtg aaattgcagg atgcaggggt gtaccgctgc atgatcagct atggtggtgc     420
cgactacaag cgaattactg tgaaagtcaa tgccccatac aacaaaatca ccaaagaat      480 tttggttgtg gatccagtca cctctgaaca tgaactgaca tgtcaggctg agggctaccc     540
caaggccgaa gtcatctgga caagcagtga ccatcaagtc ctgagtggta agaccaccac     600
caccaattcc aagagagagg agaagctttt caatgtgacc agcacactga gaatcaacac     660
aacaactaat gagatttct  actgcacttt taggagatta gatcctgagg aaaaccatac     720
agctgaattg gtcatcccag gtaatattct gaatgtgtcc attaaaatat gtctaacact     780
```

```
gtcccctagc acctagcatg atgtctgcct atcatagtca ttcagtgatt gttgaataaa      840
tgaatgaatg aataacacta tgtttacaaa atatatccta attcctcacc tccattcatc      900
caaaccatat tgttacttaa taaacattca gcagatattt atggaataaa aaaaaaaaaa      960
aaaaaaaa                                                               968
```

<210> SEQ ID NO 4
<211> LENGTH: 245
<212> TYPE: PRT
<213> ORGANISM: Homo sapiens

<400> SEQUENCE: 4

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245
```

<210> SEQ ID NO 5
<211> LENGTH: 1553
<212> TYPE: DNA
<213> ORGANISM: Homo sapiens

<400> SEQUENCE: 5

```
cgaggctccg caccagccgc gcttctgtcc gcctgcaggg cattccagaa agatgaggat      60
atttgctgtc tttatattca tgacctactg gcatttgctg aacgcattta ctgtcacggt     120
tcccaaggac ctatatgtgg tagagtatgg tagcaatatg acaattgaat gcaaattccc     180
agtagaaaaa caattagacc tggctgcact aattgtctat tgggaaatgg aggataagaa     240
```

```
cattattcaa tttgtgcatg gagaggaaga cctgaaggtt cagcatagta gctacagaca    300
gagggcccgg ctgttgaagg accagctctc cctgggaaat gctgcacttc agatcacaga    360
tgtgaaattg caggatgcag gggtgtaccg ctgcatgatc agctatggtg gtgccgacta    420
caagcgaatt actgtgaaag tcaatgcccc atacaacaaa atcaaccaaa gaattttggt    480
tgtggatcca gtcacctctg aacatgaact gacatgtcag gctgagggct accccaaggc    540
cgaagtcatc tggacaagca gtgaccatca agtcctgagt ggtaagacca ccaccaccaa    600
ttccaagaga gaggagaagc ttttcaatgt gaccagcaca ctgagaatca cacaacaac     660
taatgagatt ttctactgca cttttaggag attagatcct gaggaaaacc atacagctga    720
attggtcatc ccagaactac ctctggcaca tcctccaaat gaaaggactc acttggtaat    780
tctgggagcc atcttattat gccttggtgt agcactgaca ttcatcttcc gtttaagaaa    840
agggagaatg atggatgtga aaaaatgtgg catccaagat acaaactcaa agaagcaaag    900
tgatacacat ttggaggaga cgtaatccag cattggaact tctgatcttc aagcagggat    960
tctcaacctg tggtttaggg gttcatcggg gctgagcgtg acaagaggaa ggaatgggcc    1020
cgtgggatgc aggcaatgtg ggacttaaaa ggcccaagca ctgaaaatgg aacctggcga    1080
aagcagagga ggagaatgaa gaaagatgga gtcaaacagg gagcctggag ggagaccttg    1140
atactttcaa atgcctgagg ggctcatcga cgcctgtgac agggagaaag gatacttctg    1200
aacaaggagc ctccaagcaa atcatccatt gctcatccta ggaagacggg ttgagaatcc    1260
ctaatttgag ggtcagttcc tgcagaagtg cccctttgcct ccactcaatg cctcaatttg    1320
ttttctgcat gactgagagt ctcagtgttg aacgggaca gtatttatgt atgagttttt     1380
cctatttatt ttgagtctgt gaggtcttct tgtcatgtga gtgtggttgt gaatgatttc    1440
ttttgaagat atattgtagt agatgttaca attttgtcgc caaactaaac ttgctgctta    1500
atgatttgct cacatctagt aaaacatgga gtatttgtaa aaaaaaaaa aaa             1553
```

<210> SEQ ID NO 6
<211> LENGTH: 290
<212> TYPE: PRT
<213> ORGANISM: Homo sapiens

<400> SEQUENCE: 6

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140
```

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
                195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr
    290

<210> SEQ ID NO 7
<211> LENGTH: 819
<212> TYPE: DNA
<213> ORGANISM: Homo sapiens

<400> SEQUENCE: 7
atgatcttcc tcctgctaat gttgagcctg gaattgcagc ttcaccagat agcagcttta      60
ttcacagtga cagtccctaa ggaactgtac ataatagagc atggcagcaa tgtgaccctg     120
gaatgcaact ttgacactgg aagtcatgtg aaccttggag caataacagc cagtttgcaa     180
aaggtggaaa atgatacatc cccacaccgt gaaagagcca ctttgctgga ggagcagctg     240
cccctaggga aggcctcgtt ccacatacct caagtccaag tgagggacga aggacagtac     300
caatgcataa tcatctatgg ggtcgcctgg gactacaagt acctgactct gaaagtcaaa     360
gcttcctaca ggaaaataaa cactcacatc ctaaaggttc agaaacaga tgaggtagag     420
ctcacctgcc aggctacagg ttatcctctg cagaagtat cctggccaaa cgtcagcgtt     480
cctgccaaca ccagccactc caggaccct gaaggcctct accaggtcac cagtgttctg     540
cgcctaaagc cacccctgg cagaaacttc agctgtgtgt tctggaatac tcacgtgagg     600
gaacttactt tggccagcat tgaccttcaa agtcagatgg aacccaggac ccatccaact     660
tggctgcttc acattttcat cccctcctgc atcattgctt tcattttcat agccacagtg     720
atagccctaa gaaacaact ctgtcaaaag ctgtattctt caaagacac aacaaaaga      780
cctgtcacca acaaagag ggaagtgaac agtgctatc                           819

<210> SEQ ID NO 8
<211> LENGTH: 273
<212> TYPE: PRT
<213> ORGANISM: Homo sapiens

<400> SEQUENCE: 8

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
 50                  55                  60

Asp Thr Ser Pro His Arg Glu Arg Ala Thr Leu Leu Glu Glu Gln Leu
 65                  70                  75                  80

Pro Leu Gly Lys Ala Ser Phe His Ile Pro Gln Val Gln Val Arg Asp
                 85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
            195                 200                 205

Leu Gln Ser Gln Met Glu Pro Arg Thr His Pro Thr Trp Leu Leu His
210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile

<210> SEQ ID NO 9
<211> LENGTH: 1437
<212> TYPE: DNA
<213> ORGANISM: Homo sapiens

<400> SEQUENCE: 9
atgataagga agaagaggaa gcgaagcgcg cccccccggcc catgccgcag ccacgggccc        60
agacccgcca cggcgcccgc gccgccgccc tcgccggagc ccacgagacc tgcatggacg       120
ggcatgggct tgagagcagc accttccagc gccgccgctg ccgccgccga ggttgagcag       180
cgccgcagcc ccgggctctg ccccccgccg ctggagctgc tgctgctgct gctgttcagc       240
ctcgggctgc tccacgcagg tgactgccaa cagccagccc aatgtcgaat ccagaaatgc       300
accacggact tcgtgtccct gacttctcac ctgaactctg ccgttgacgg ctttgactct       360
gagttttgca aggccttgcg tgcctatgct ggctgcaccc agcgaacttc aaaagcctgc       420
cgtggcaacc tggtatacca ttctgccgtg ttgggtatca gtgacctcat gagccagagg       480
aattgttcca aggatggacc cacatcctct accaaccccg aagtgaccca tgatccttgc       540
aactatcaca gccacgctgg agccagggaa cacaggagag ggaccagaa ccctcccagt       600 taccttttt gtggcttgtt tggagatcct cacctcagaa ctttcaagga taacttccaa       660
acatgcaaag tagaagggc ctggccactc atagataata attatctttc agttcaagtg       720

```
acaaacgtac ctgtggtccc tggatccagt gctactgcta caaataagat cactattatc    780
ttcaaagccc accatgagtg tacagatcag aaagtctacc aagctgtgac agatgacctg    840
ccggccgcct ttgtggatgg caccaccagt ggtggggaca gcgatgccaa gagcctgcgt    900
atcgtggaaa gggagagtgg ccactatgtg gagatgcacg cccgctatat agggaccaca    960
gtgtttgtgc ggcaggtggg tcgctacctg acccttgcca tccgtatgcc tgaagacctg   1020
gccatgtcct acgaggagag ccaggacctg cagctgtgcg tgaacggctg ccccctgagt   1080
gaacgcatcg atgacgggca gggccaggtg tctgccatcc tgggacacag cctgcctcgc   1140
acctccttgg tgcaggcctg gcctggctac acactggaga ctgccaacac tcaatgccat   1200
gagaagatgc cagtgaagga catctatttc cagtcctgtg tcttcgacct gctcaccact   1260
ggtgatgcca actttactgc cgcagcccac agtgccttgg aggatgtgga ggccctgcac   1320
ccaaggaagg aacgctggca catttttccc agcagtggca atgggactcc ccgtggaggc   1380
agtgatttgt ctgtcagtct aggactcacc tgcttgatcc ttatcgtgtt tttgtag      1437

<210> SEQ ID NO 10
<211> LENGTH: 478
<212> TYPE: PRT
<213> ORGANISM: Homo sapiens

<400> SEQUENCE: 10

Met Ile Arg Lys Lys Arg Lys Arg Ser Ala Pro Gly Pro Cys Arg
1               5                   10                  15

Ser His Gly Pro Arg Pro Ala Thr Ala Pro Ala Pro Pro Ser Pro
                20                  25                  30

Glu Pro Thr Arg Pro Ala Trp Thr Gly Met Gly Leu Arg Ala Pro
        35                  40                  45

Ser Ser Ala Ala Ala Ala Ala Glu Val Glu Gln Arg Arg Ser Pro
    50                  55                  60

Gly Leu Cys Pro Pro Leu Glu Leu Leu Leu Leu Leu Leu Phe Ser
65                  70                  75                  80

Leu Gly Leu Leu His Ala Gly Asp Cys Gln Gln Pro Ala Gln Cys Arg
                85                  90                  95

Ile Gln Lys Cys Thr Thr Asp Phe Val Ser Leu Thr Ser His Leu Asn
                100                 105                 110

Ser Ala Val Asp Gly Phe Asp Ser Glu Phe Cys Lys Ala Leu Arg Ala
        115                 120                 125

Tyr Ala Gly Cys Thr Gln Arg Thr Ser Lys Ala Cys Arg Gly Asn Leu
    130                 135                 140

Val Tyr His Ser Ala Val Leu Gly Ile Ser Asp Leu Met Ser Gln Arg
145                 150                 155                 160

Asn Cys Ser Lys Asp Gly Pro Thr Ser Ser Thr Asn Pro Glu Val Thr
                165                 170                 175

His Asp Pro Cys Asn Tyr His Ser His Ala Gly Ala Arg Glu His Arg
            180                 185                 190

Arg Gly Asp Gln Asn Pro Pro Ser Tyr Leu Phe Cys Gly Leu Phe Gly
        195                 200                 205

Asp Pro His Leu Arg Thr Phe Lys Asp Asn Phe Gln Thr Cys Lys Val
    210                 215                 220

Glu Gly Ala Trp Pro Leu Ile Asp Asn Asn Tyr Leu Ser Val Gln Val
225                 230                 235                 240

Thr Asn Val Pro Val Val Pro Gly Ser Ser Ala Thr Ala Thr Asn Lys
                245                 250                 255
```

```
Ile Thr Ile Ile Phe Lys Ala His His Glu Cys Thr Asp Gln Lys Val
        260                 265                 270

Tyr Gln Ala Val Thr Asp Asp Leu Pro Ala Ala Phe Val Asp Gly Thr
            275                 280                 285

Thr Ser Gly Gly Asp Ser Asp Ala Lys Ser Leu Arg Ile Val Glu Arg
        290                 295                 300

Glu Ser Gly His Tyr Val Glu Met His Ala Arg Tyr Ile Gly Thr Thr
305                 310                 315                 320

Val Phe Val Arg Gln Val Gly Arg Tyr Leu Thr Leu Ala Ile Arg Met
                325                 330                 335

Pro Glu Asp Leu Ala Met Ser Tyr Glu Glu Ser Gln Asp Leu Gln Leu
            340                 345                 350

Cys Val Asn Gly Cys Pro Leu Ser Glu Arg Ile Asp Asp Gly Gln Gly
        355                 360                 365

Gln Val Ser Ala Ile Leu Gly His Ser Leu Pro Arg Thr Ser Leu Val
        370                 375                 380

Gln Ala Trp Pro Gly Tyr Thr Leu Glu Thr Ala Asn Thr Gln Cys His
385                 390                 395                 400

Glu Lys Met Pro Val Lys Asp Ile Tyr Phe Gln Ser Cys Val Phe Asp
                405                 410                 415

Leu Leu Thr Thr Gly Asp Ala Asn Phe Thr Ala Ala His Ser Ala
            420                 425                 430

Leu Glu Asp Val Glu Ala Leu His Pro Arg Lys Glu Arg Trp His Ile
            435                 440                 445

Phe Pro Ser Ser Gly Asn Gly Thr Pro Arg Gly Gly Ser Asp Leu Ser
    450                 455                 460

Val Ser Leu Gly Leu Thr Cys Leu Ile Leu Ile Val Phe Leu
465                 470                 475

<210> SEQ ID NO 11
<211> LENGTH: 867
<212> TYPE: DNA
<213> ORGANISM: Homo sapiens

<400> SEQUENCE: 11
atgggccaca cacggaggca gggaacatca ccatccaagt gtccatacct caatttcttt      60
cagctcttgg tgctggctgg tctttctcac ttctgttcag gtgttatcca cgtgaccaag     120
gaagtgaaag aagtggcaac gctgtcctgt ggtcacaatg tttctgttga agagctggca     180
caaactcgca tctactggca aaaggagaag aaaatggtgc tgactatgat gtctggggac     240
atgaatatat ggcccgagta caagaaccgg accatctttg atatcactaa taacctctcc     300
attgtgatcc tggctctgcg cccatctgac gagggcacat acgagtgtgt tgttctgaag     360
tatgaaaaag acgctttcaa gcgggaacac ctggctgaag tgacgttatc agtcaaagct     420
gacttcccta cacctagtat atctgacttt gaaattccaa cttctaatat tagaaggata     480
atttgctcaa cctctggagg ttttccagag cctcacctct cctggttgga aaatggagaa     540
gaattaaatg ccatcaacac aacagtttcc caagatcctg aaactgagct ctatgctgtt     600
agcagcaaac tggatttcaa tatgacaacc aaccacagct tcatgtgtct catcaagtat     660
ggacatttaa gagtgaatca gaccttcaac tggaatacaa ccaagcaaga gcattttcct     720 gataaccctgc tcccatcctg ggccattacc ttaatctcag taaatggaat tttgtgata     780 tgctgcctga cctactgctt tgccccaaga tgcagagaga aaggaggaa tgagagattg     840 agaagggaaa gtgtacgccc tgtataa                                         867
```

<210> SEQ ID NO 12
<211> LENGTH: 288
<212> TYPE: PRT
<213> ORGANISM: Homo sapiens

<400> SEQUENCE: 12

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285

<210> SEQ ID NO 13
<211> LENGTH: 321
<212> TYPE: DNA
<213> ORGANISM: Artificial Sequence
<220> FEATURE:
<223> OTHER INFORMATION: Antibody 1B9 vK DNA

<400> SEQUENCE: 13
gacattgtga tgacccagtc tcacaaattc atgtccacat cactaggaga cagggtcacc      60
atcacctgca aggccagtca ggatgtgggt atttctgtag tttggtatca acagaaacca     120
gggcaatctc ctaaaactact gatttactgg gcatccaccc ggcacactgg agtccctgat    180
cgcttcacag gcagtggatc tgggacagat ttcactctga ccattaacaa tgtgcagtct    240

```
gaagacttgg cagattattt ctgtcagcaa tatagcagct atccgctcac ggtcggtgct    300
gggaccaagc tggagctgaa a                                             321
```

<210> SEQ ID NO 14
<211> LENGTH: 107
<212> TYPE: PRT
<213> ORGANISM: Artificial Sequence
<220> FEATURE:
<223> OTHER INFORMATION: Antibody 1B9 vK protein

<400> SEQUENCE: 14

```
Asp Ile Val Met Thr Gln Ser His Lys Phe Met Ser Thr Ser Leu Gly
1               5                   10                  15

Asp Arg Val Thr Ile Thr Cys Lys Ala Ser Gln Asp Val Gly Ile Ser
            20                  25                  30

Val Val Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys Gln Gln Tyr Ser Ser Tyr Pro Leu
                85                  90                  95

Thr Val Gly Ala Gly Thr Lys Leu Glu Leu Lys
            100                 105
```

<210> SEQ ID NO 15
<211> LENGTH: 363
<212> TYPE: DNA
<213> ORGANISM: Artificial Sequence
<220> FEATURE:
<223> OTHER INFORMATION: Antibody 1B9 vH DNA

<400> SEQUENCE: 15

```
gatgtgcagc ttcaggagtc gggacctggc ctggtgaaac cttctcagtc tctgtccctc    60
acctgcactg tcactggcta ctcaatcacc agtgatcatg cctggaactg gatccggcag   120
gttccaggaa acaaactgga gtggatgggc tacataacct accgtggtag cactacctat   180
agcccatctc tcaaaagtcg aatttctatc actcgagaca catccaagaa ccagttcttc   240
ctgcagttga attctgtgac tactgaggac acagccacat attactgtgc aagatctatg   300
attacgacgg ggtactatgt tatggactac tggggtcaag gaacctcagt caccgtctcc   360
tca                                                                363
```

<210> SEQ ID NO 16
<211> LENGTH: 121
<212> TYPE: PRT
<213> ORGANISM: Artificial Sequence
<220> FEATURE:
<223> OTHER INFORMATION: Antibody 1B9 vH protein

<400> SEQUENCE: 16

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

His Ala Trp Asn Trp Ile Arg Gln Val Pro Gly Asn Lys Leu Glu Trp
        35                  40                  45
```

```
Met Gly Tyr Ile Thr Tyr Arg Gly Ser Thr Thr Tyr Ser Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Glu Asp Thr Ala Thr Tyr Tyr Cys
                 85                  90                  95

Ala Arg Ser Met Ile Thr Thr Gly Tyr Tyr Val Met Asp Tyr Trp Gly
            100                 105                 110

Gln Gly Thr Ser Val Thr Val Ser Ser
            115                 120
```

<210> SEQ ID NO 17
<211> LENGTH: 321
<212> TYPE: DNA
<213> ORGANISM: Artificial Sequence
<220> FEATURE:
<223> OTHER INFORMATION: Antibody 4H1 vK DNA

<400> SEQUENCE: 17

```
gacattgtga tgacccagtc tcacaaattc atgtccacat cagtaggaga cagggtcagc    60
atctcctgca aggccagtca ggatgtgggt atttctgtag cctggtatca acagaaacca   120
gggcaatctc ctaaactact gatttactgg gcatccaccc ggcacactgg agtccctgtt   180
cgcttcacag gcagtggatc tgggacagat ttcactctca ccataagcaa tgtgcagtct   240
gaagacttgg cagattattt ttgtcagcag tatagcagtt atccgccacc gttcggtgct   300
gggaccaagc tggagctgaa a                                             321
```

<210> SEQ ID NO 18
<211> LENGTH: 107
<212> TYPE: PRT
<213> ORGANISM: Artificial Sequence
<220> FEATURE:
<223> OTHER INFORMATION: Antibody 4H1 vK protein

<400> SEQUENCE: 18

```
Asp Ile Val Met Thr Gln Ser His Lys Phe Met Ser Thr Ser Val Gly
 1               5                  10                  15

Asp Arg Val Ser Ile Ser Cys Lys Ala Ser Gln Asp Val Gly Ile Ser
             20                  25                  30

Val Ala Trp Tyr Gln Gln Lys Pro Gly Gln Ser Pro Lys Leu Leu Ile
         35                  40                  45

Tyr Trp Ala Ser Thr Arg His Thr Gly Val Pro Val Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Pro Pro
                 85                  90                  95

Thr Phe Gly Ala Gly Thr Lys Leu Glu Leu Lys
            100                 105
```

<210> SEQ ID NO 19
<211> LENGTH: 363
<212> TYPE: DNA
<213> ORGANISM: Artificial Sequence
<220> FEATURE:
<223> OTHER INFORMATION: Antibody 4H1 vH DNA

<400> SEQUENCE: 19

```
gatgtgcagc ttcaggagtc gggacctggc ctggtgaaac cttctcagtc tctgtccctc      60
acctgcactg tcactgacta ctcaatcacc agtgattatg cctggacctg gatccggcag     120
tttccgggaa acaaactgga gtggatgggc tacataacct acagaggtac cactcgctac     180
aacccatctc tcacaagtcg aatctctttc actcgagaca catccaagaa ccagctcttc     240
ctgcagttga attctgtgac tactgaggac acaggcacat attgctgtgc aagatctatg     300
attacgacgg ggtactatgc tatggactac tggggtcaag gaacctcagt caccgtctcc     360
tca                                                                   363
```

<210> SEQ ID NO 20
<211> LENGTH: 121
<212> TYPE: PRT
<213> ORGANISM: Artificial Sequence
<220> FEATURE:
<223> OTHER INFORMATION: Antibody 4H1 vH protein

<400> SEQUENCE: 20

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Ile Thr Ser Asp
            20                  25                  30

Tyr Ala Trp Thr Trp Ile Arg Gln Phe Pro Gly Asn Lys Leu Glu Trp
        35                  40                  45

Met Gly Tyr Ile Thr Tyr Arg Gly Thr Thr Arg Tyr Asn Pro Ser Leu
    50                  55                  60

Thr Ser Arg Ile Ser Phe Thr Arg Asp Thr Ser Lys Asn Gln Leu Phe
65                  70                  75                  80

Leu Gln Leu Asn Ser Val Thr Thr Glu Asp Thr Gly Thr Tyr Cys Cys
                85                  90                  95

Ala Arg Ser Met Ile Thr Thr Gly Tyr Tyr Ala Met Asp Tyr Trp Gly
            100                 105                 110

Gln Gly Thr Ser Val Thr Val Ser Ser
        115                 120

<210> SEQ ID NO 21
<211> LENGTH: 18
<212> TYPE: PRT
<213> ORGANISM: Artificial Sequence
<220> FEATURE:
<223> OTHER INFORMATION: Conserved PD-L1 peptide

<400> SEQUENCE: 21

Cys Phe Thr Val Thr Val Pro Lys Asp Leu Tyr Val Val Glu Tyr Gly
1               5                   10                  15

Ser Asn

<210> SEQ ID NO 22
<211> LENGTH: 18
<212> TYPE: PRT
<213> ORGANISM: Artificial Sequence
<220> FEATURE:
<223> OTHER INFORMATION: Conserved PD-L2 peptide

```
<400> SEQUENCE: 22

Cys Tyr Arg Ser Met Ile Ser Tyr Gly Gly Ala Asp Tyr Lys Arg Ile
1               5                   10                  15

Thr Val
```